(12) United States Patent
Ali et al.

(10) Patent No.: US 10,344,039 B2
(45) Date of Patent: Jul. 9, 2019

(54) MACROCYCLIC SPIROCARBAMATE DERIVATIVES AS FACTOR XIA INHIBITORS, PHARMACEUTICALLY ACCEPTABLE COMPOSITIONS AND THEIR USE

(71) Applicants: MERCK SHARP & DOHME CORP., Rahway, NJ (US); Amjad Ali, Freehold, NJ (US); Yeon-Hee Lim, Piscataway, NJ (US); Jiayi Xu, Edison, NJ (US); Wei Zhou, Scotch Plains, NJ (US)

(72) Inventors: Amjad Ali, Freehold, NJ (US); Yeon-Hee Lim, Piscataway, NJ (US); Jiayi Xu, Edison, NJ (US); Wei Zhou, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/771,136

(22) PCT Filed: Oct. 24, 2016

(86) PCT No.: PCT/US2016/058363
§ 371 (c)(1),
(2) Date: Apr. 26, 2018

(87) PCT Pub. No.: WO2017/074833
PCT Pub. Date: May 4, 2017

(65) Prior Publication Data
US 2018/0311250 A1    Nov. 1, 2018

Related U.S. Application Data

(60) Provisional application No. 62/248,268, filed on Oct. 29, 2015.

(51) Int. Cl.
*C07D 519/00* (2006.01)
*C07D 498/10* (2006.01)
*A61P 7/00* (2006.01)

(52) U.S. Cl.
CPC .............. *C07D 519/00* (2013.01); *A61P 7/00* (2018.01); *C07D 498/10* (2013.01)

(58) Field of Classification Search
CPC .................................................. C07D 519/00
See application file for complete search history.

(56) References Cited

U.S. PATENT DOCUMENTS

| | | | |
|---|---|---|---|
| 7,696,201 B2 | 4/2010 | Makings et al. | |
| 8,828,983 B2* | 9/2014 | Quan | C07D 487/08 514/183 |
| 2012/0015928 A1* | 1/2012 | Yao | C07D 207/06 514/210.02 |
| 2014/0221338 A1 | 8/2014 | Pinto et al. | |
| 2015/0152112 A1* | 6/2015 | Courtney | C07D 401/14 514/233.2 |
| 2015/0166550 A1* | 6/2015 | Yang | C07D 401/04 514/248 |

FOREIGN PATENT DOCUMENTS

| | | |
|---|---|---|
| WO | 2011100401 A1 | 8/2011 |
| WO | 2015123090 A1 | 8/2015 |
| WO | 2015123093 A1 | 8/2015 |
| WO | 2015164308 A1 | 10/2015 |
| WO | WO-2015164308 A1 * | 10/2015 ........... C07D 471/10 |

OTHER PUBLICATIONS

Cho et al. Bull. Korean Chem. Soc. 2013, 34, 1212-1220 (Year: 2013).*
International Search Report and Written Opinion for PCT/US2016/058363, dated Jan. 25, 2017, 8 pages.
Supplementary European Search Report for 13860557.4, dated Mar. 25, 2019; 7 pages.

* cited by examiner

*Primary Examiner* — Matthew P Coughlin
(74) *Attorney, Agent, or Firm* — Nicole M. Beeler; John C. Todaro

(57) ABSTRACT

The present invention provides a compound of Formula (I) and stereoisomers thereof, and pharmaceutically acceptable salts of said compounds and said stereoisomers, and pharmaceutical compositions thereof, and methods for using said compounds and compositions for treating or preventing thromboses, embolisms, hypercoagulability or fibrotic changes. The compounds are selective Factor XIa inhibitors or dual inhibitors of Factor XIa and plasma kallikrein.

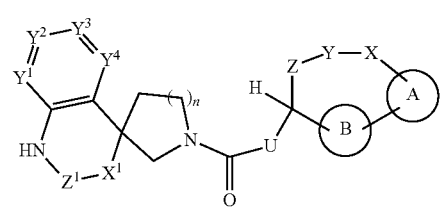

(I)

17 Claims, No Drawings

US 10,344,039 B2

MACROCYCLIC SPIROCARBAMATE DERIVATIVES AS FACTOR XIA INHIBITORS, PHARMACEUTICALLY ACCEPTABLE COMPOSITIONS AND THEIR USE

CROSS REFERENCE TO RELATED APPLICATIONS

This application is a U.S. National Phase application under 35 U.S.C. § 371 of PCT Application No. PCT/US2016/058363 filed Oct. 24, 2016, which claims priority from U.S. Ser. No. 62/248,268 filed Oct. 29, 2015.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, andother humoral and cellular pathways (for review, Coleman, R., "Contact ActivationPathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic 5 diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma kallikrein is a zymogen of a trypsin-like serine protease and is present in plasma. The gene structure is similar to that of factor XI. Overall, the amino acid sequence of plasma kallikrein has 58% homology to factor XI. Proteolyticactivation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease 15 inhibitors, including alpha 2 macroglobulin and Cl-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability andvasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on Cl-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma kallikrein, and treatment with a protein-based reversible plasma kallikrein inhibitor, Ecallantide (Kalbitor), has been approved by the FDA for the treatment of acute attacks of HAE (Schneider, L, et al., J. Allergy Clin. Immunol., 120: p.416 (2007)).

Additionally, the plasma kallikrein-kinin system is abnormally abundant in patients diagnosed with advanced diabetic macular edema (DME). Recent publications have shown that plasma kallikrein contributes to observed retinal vascular leakage and dysfunction in diabetic rodent models (A.

Clermont, et al., Diabetes, 60:1590 (2011)), and that treatment with a small molecule plasma kallikrein inhibitor ameliorated the observed retinal vascular permeability and other abnormalities related to retinal blood flow.

Factor XIa inhibitor compounds are described in WO2015123093, WO2015123091, WO2015123090, WO2015120777, WO2015120062, WO2015116885, WO2015116882, WO2015107724, WO2015063093, WO2015063093, WO2015054087, WO2015047973, WO2015044174, WO2015044173, WO2015044172, WO2015044170, WO2015044169, WO2015044167, WO2015044165, WO2015044163, WO2015011087, WO2014160668, WO2014160592, WO2014059214, WO2014059203, WO2014059202, WO2014022767, WO2014022766, WO2014014050, WO2013174937, WO2013022814, WO2013022814, WO2013022818, WO 2013055984, WO2013056034, WO2013056060, WO2013118805, WO2013093484, WO2002042273, WO2002037937, WO2002060894, WO2003015715, WO2004002405, US20040180855, WO2004080971, WO2004094372, US20050228000, US20050282805, WO2005123680, US20090036438, US20120088758, US20060074103, WO2006062972, WO2006076246, US20060154915, US20090062287, US20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula (I):

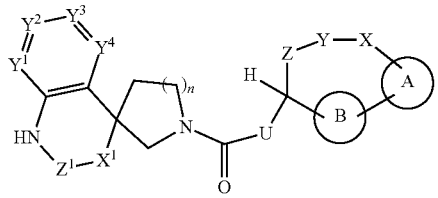

and stereoisomers thereof, and pharmaceutically acceptable salts of said compounds and said stereoisomers, wherein each of the variables is as defined herein. The compounds of Formula (I) are selective Factor XIa inhibitors or dual inhibitors of Factor XIa and plasma kallikrein, and as such may be useful in the treatment, inhibition or amelioration of one or more disease states that could benefit from inhibition of Factor XIa or plasma kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

For each of the following embodiments, any variable not explicitly defined in the embodiment is as defined in Formula (I). In each of the embodiments described herein, each variable is selected independently of the other unless otherwise noted. The compounds of Formulas (I), (IA), (II), (IIA), (III), and (IIIA), and the compounds shown in the Examples below, or stereoisomers thereof, or pharmaceutically acceptable salts of said compounds and/or said stereoisomers, may be collectively or individually referred to as a "compound(s) of the invention."

The present invention relates to compounds of Formula (I):

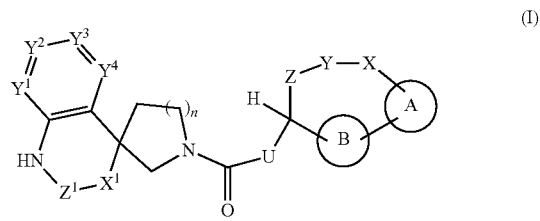

or a pharmaceutically acceptable salt thereof, wherein:
$Y^1$ is $CR^3$ or N;
$Y^2$ is $CR^3$ or N;
$Y^3$ is $CR^3$ or N;
$Y^4$ is $CR^3$ or N,
such that three of $Y^1$, $Y^2$, $Y^3$ and $Y^4$ are not simultaneously N, and all four of $Y^1$, $Y^2$, $Y^3$ and $Y^4$ are not simultaneously N;
each $R^3$ is independently hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl;
U is a bond or NH;
—$Z^1$—$X^1$— is —C(O)O—, —C(O)CH$_2$—, —C(O)NH—, —S(O)$_2$O—, —S(O)$_2$CH$_2$—, —S(O)$_2$NH—, —S(O)CH$_2$—, —S(O)NH—, —C(O)—, or —S(O)$_2$—;
n is 1, 2, or 3;
Ⓐ is aryl or heteroaryl, each of which is optionally substituted with one to three groups independently selected from halo, cyano, $R^6$, $OR^6$, $C(O)OR^6$, $NR^6R^7$, $NHC(O)O$ $(C_1-C_6)$alkyl, $NHC(O)OC_{3-6}$cycloalkyl, —$NHSO_2(C_1-C_6)$ alkyl, $CONR^7R^8$, or —$CH_2CONR^7R^8$;
Ⓑ is aryl or heteroaryl, which is optionally substituted with one to three groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$;
—Y—X— is selected from the group consisting of —C(O)—NR$^6$—, —CH(R$^5$)C(O)—NR$^6$—, —CH(C(O)OR$^7$)—NR$^6$—, —C(O)—O—, —NR$^6$—C(O)—, —CH(C(O)N(R$^6$R$^7$))—NR$^6$—, —CH(CR$^6$R$^7$OR$^8$)—NR$^6$—, —CH(CR$^6$R$^7$NR$^6$R$^7$)—NR$^6$—, —OC(O)—NR$^6$—, —NR$^6$—C(O)O—, —NR$^6$—C(O)NR$^6$—, and —S(O)$_2$—NR$^6$—;
$R^5$ is fluoro or $C_{1-6}$ alkyl;
Z is $C_{3-8}$ alkylene or $C_{3-8}$ alkenylene, wherein one of the carbon atoms in said alkylene and alkenylene, where chemically permitted, may be replaced with O, NR$^6$, C(O), C(O) NR$^6$, NR$^6$C(O), S, SO or SO$_2$;
each $R^6$ is independently hydrogen or $C_{1-6}$ alkyl, which is optionally substituted with one to three groups independently selected from the group consisting of halo, hydroxyl, $(C_1-C_3)$alkoxyl, C(O)OH, and C(O)O$(C_1-C_3)$alkyl;
each $R^7$ is independently hydrogen, $C_{1-6}$ alkyl, heteroaryl or heterocyclyl, wherein said alkyl group is optionally substituted with one to three groups independently selected from the group consisting of halo and hydroxy; and each $R^8$ is independently hydrogen or $C_{1-6}$ alkyl.

In another embodiment, the compounds of the invention have a structural Formula (IA):

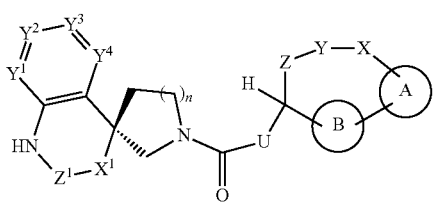

(IA)

or a pharmaceutically acceptable salt thereof, wherein each variable is as defined in Formula (I).

In another embodiment, in each of Formulas (I) and (IA): $Y^1$ is $CR^3$, wherein $R^3$ is hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl.

In an alternative of the immediately preceding embodiment, in each of Formulas (I) and (IA), $R^3$ is H.

In another embodiment, in each of Formulas (I) and (IA): $Y^1$ is N.

In another embodiment, in each of Formulas (I) and (IA): $Y^2$ is $CR^3$, wherein $R^3$ is hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl.

In an alternative of the immediately preceding embodiment, in each of Formulas (I) and (IA), $R^3$ is H.

In another embodiment, in each of Formulas (I) and (IA): $Y^2$ is N.

In another embodiment, in each of Formulas (I) and (IA): $Y^3$ is $CR^3$, wherein $R^3$ is hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl.

In an alternative of the immediately preceding embodiment, in each of Formulas (I) and (IA), $R^3$ is H.

In another embodiment, in each of Formulas (I) and (IA): $Y^3$ is N.

In another embodiment, in each of Formulas (I) and (IA): $Y^4$ is $CR^3$, wherein $R^3$ is hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl.

In an alternative of the immediately preceding embodiment, in each of Formulas (I) and (IA), $R^3$ is H.

In another embodiment, in each of Formulas (I) and (IA): $Y^4$ is N.

In another embodiment, in each of Formulas (I) and (IA): $Y^1$, $Y^2$, $Y^3$, and $Y^4$ are each $CR^3$, wherein each $R^3$ is independently hydrogen, $C_{1-3}$ alkyl, $C_3$-6 cycloalkyl, halo, cyano or hydroxy, wherein said $C_{1-3}$ alkyl and said $C_{3-6}$ cycloalkyl groups are optionally independently substituted with one to three groups independently selected from halo or hydroxyl.

In an alternative of the immediately preceding embodiment, in each of Formulas (I) and (IA), each $R^3$ is H.

In another embodiment, in each of Formulas (I) and (IA): —$Z^1$—$X^1$— is selected from the group consisting of: —C(O)O—, —C(O)CH$_2$—, —C(O)NH—, —C(O)—, and —S(O)$_2$—.

In another embodiment, in each of Formulas (I) and (IA): —$Z^1$—$X^1$— is selected from the group consisting of: —C(O)O—, —C(O)CH$_2$—, —C(O)NH—, and —C(O)—.

In another embodiment, in each of Formulas (I) and (IA): —$Z^1$—$X^1$— is selected from the group consisting of: —C(O)O—, and —C(O)—.

In another embodiment, in each of Formulas (I) and (IA): —$Z^1$—$X^1$— is —C(O)O—.

In another embodiment, the compounds of the invention have a structural Formula (II):

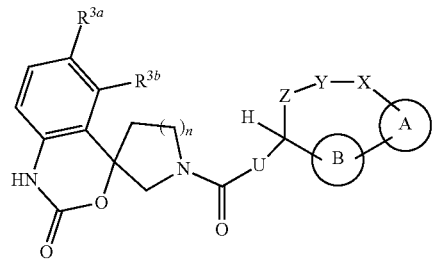

(II)

or a pharmaceutically acceptable salt thereof, wherein $R^{3a}$ is halo; $R^{3b}$ is selected from the group consisting of H and halo; and each remaining variable is as defined in Formula (I).

In another embodiment, the compounds of the invention have a structural Formula (IIA):

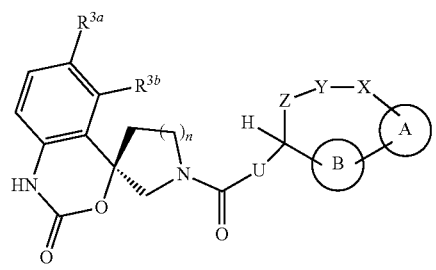

(IIA)

or a pharmaceutically acceptable salt thereof, wherein $R^{3a}$ is selected from the group consisting of fluoro and chloro; $R^{3b}$ is selected from the group consisting of H, chloro and fluoro; and each remaining variable is as defined in Formula (I).

In another embodiment, the compounds of the invention have a structural Formula (III):

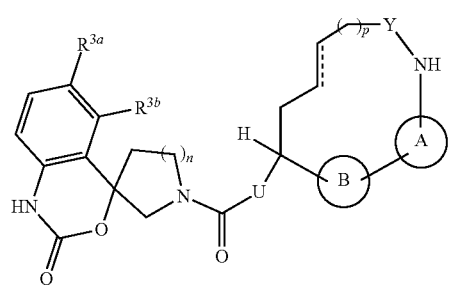

(III)

, or a pharmaceutically acceptable salt thereof, wherein the dotted line represents a single or double bond; $R^{3a}$ is halo; $R^{3b}$ is selected from the group consisting of H and halo; p is 0, 1 or 2; and each remaining variable is as defined in Formula (I).

In another embodiment, the compounds of the invention have a structural Formula (IIIA):

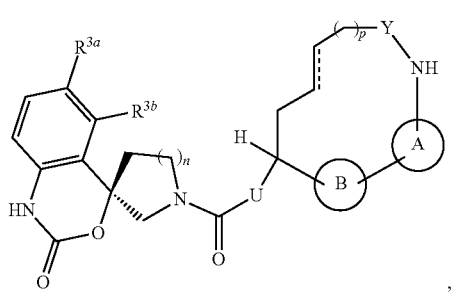

(IIIA)

or a pharmaceutically acceptable salt thereof, wherein the dotted line represents a single or double bond; $R^{3a}$ is halo; $R^{3b}$ is selected from the group consisting of H and halo; p is 0, 1 or 2; and each remaining variable is as defined in Formula (I).

In another embodiment, in each of Formulas (II), (IIA), (III), and (IIIA):
$R^{3a}$ is chloro and $R^{3b}$ is selected from the group consisting of H, chloro and fluoro.

In another embodiment, in each of Formulas (II), (IIA), (III), and (IIIA):
$R^{3a}$ is chloro and $R^{3b}$ is H.

In another embodiment, in each of Formulas (II), (IIA), (III), and (IIIA):
$R^{3a}$ is chloro and $R^{3b}$ is fluoro.

The following alternative embodiments of "n" are contemplated in combination with each of the embodiments and alternative embodiments described above.

In another embodiment, in each of Formulas (I), (IA), (II), (IIA), (III), and (IIIA):
n is 1 or 2.

In another embodiment, in each of Formulas (I), (IA), (II), (IIA), (III), and (IIIA):
n is 1.

In another embodiment, in each of Formulas (I), (IA), (II), (IIA), (III), and (IIIA):
n is 2.

The following alternative embodiments of the moiety —Y—X— are contemplated in combination with any of the embodiments described hereinabove.

In another embodiment, in each of Formulas (I), (IA), (II), (IIA), (III), and (IIIA):
—Y—X— is —C(O)—$NR^6$—, —CH($R^5$)C(O)—$NR^6$—, —CH(C(O)$OR^7$)—$NR^6$—, —CH(C(O)N($R^6R^7$))—$NR^6$—, —CH($CR^6R^7OR^8$)—$NR^6$—, —CH($CR^6R^7NR^6R^7$)—$NR^6$—, —OC(O)—$NR^6$—, —$NR^6$—C(O)$NR^6$—, or —S(O)$_2$—$NR^6$—.

In another embodiment, in each of Formulas (I), (IA), (II), (IIA), (III), and (IIIA):
—Y—X— is —C(O)—NH—, —CH($R^5$)C(O)—NH—, —CH(C(O)$OR^7$)—NH—, —CH(C(O)N($R^6R^7$))—NH—, —CH($CR^6R^7OR^8$)—NH—, —CH($CR^6R^7NR^6R^7$)—NH—, —OC(O)—NH—, —$NR^6$—C(O)NH—, or —S(O)$_2$—NH—.

In another embodiment, in each of Formulas (I), (IA), (II), (IIA), (III), and (IIIA):
—Y—X— is —C(O)—$NR^6$—, —CH($R^5$)C(O)—$NR^6$—, or —CH(C(O)$OR^7$)—$NR^6$—.

In another embodiment, in each of Formulas (I), (IA), (II), (IIA), (III), and (IIIA): —Y—X— is —C(O)—NH—, —CH($R^5$)C(O)—NH—, or —CH(C(O)$OR^7$)—NH—.

In another embodiment, in each of Formulas (I), (IA), (II), (IIA), (III), and (IIIA):
—Y—X— is —C(O)—NH—, —CH($R^5$)C(O)—NH—, or —CH(C(O)$OR^7$)—NH—, wherein $R^5$ is $CH_3$; $R^6$ is H; and $R^7$ is H or $C_{1-6}$alkyl.

In another embodiment, in each of Formulas (III) and (IIIA):
—Y—X— is —C(O)—$NR^6$—; p is 0 or 1; and the dotted line represents a single bond. In an alternative of this embodiment $R^6$ is H.

In another embodiment, in each of Formulas (III) and (IIIA):
—Y—X— is —C(O)—$NR^6$—; p is 1 or 2; and the dotted line represents a double bond. In an alternative of this embodiment $R^6$ is H.

In another embodiment, in each of Formulas (III) and (IIIA):
—Y—X— is —CH($R^5$)C(O)—$NR^6$—; and p is 0, 1 or 2. In an alternative of this embodiment, $R^5$ is $CH_3$; $R^6$ is H; and the dotted line represents a single bond.

In another embodiment, in each of Formulas (III) and (IIIA):
—Y—X— is —CH(C(O)$OR^7$)—NH—; and p is 0, 1, or 2. In an alternative of this embodiment, $R^7$ is H or $C_{1-6}$alkyl.

In another embodiment, in each of Formulas (III) and (IIIA):
—Y—X— is —CH(C(O)$OR^7$)—NH—; p is 1, or 2; and the dotted line represents a double bond.

In an alternative of this embodiment, $R^7$ is H or $C_{1-6}$alkyl.

The following alternative embodiments of U are contemplated in combination with any of the embodiments described hereinabove.

In one embodiment, in each of Formulas (I), (IA), (II), (IIA), (III), and (IIIA): U is a bond.

In one embodiment, in each of Formulas (I), (IA), (II), (IIA), (III), and (IIIA):
U is NH.

The following alternative embodiments of Ⓐ are contemplated in combination with any of the embodiments described hereinabove.

In one embodiment, in each of Formulas (I), (IA), (II), (IIA), (III), and (IIIA):
Ⓐ is

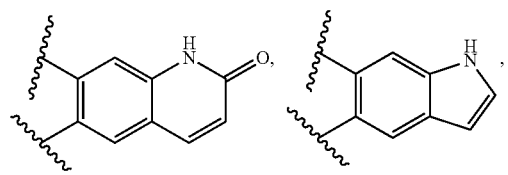

or phenyl, each of which is optionally substituted with one to three groups independently selected from the group consisting of halo, cyano, $R^6$, $OR^6$, C(O)$OR^6$, $NR^6R^7$, NHC(O)O($C_1$-$C_6$)alkyl, NHC(O)O$C_{3-6}$cycloalkyl, $NHSO_2$($C_1$-$C_6$)alkyl, $CONR^7R^8$, and $CH_2CONR^7R^8$.

In another embodiment, in each of Formulas (I), (IA), (II), (IIA), (III), and (IIIA):

(A) is unsubstituted phenyl.

In another embodiment, in each of Formulas (I), (IA), (II), (IIA), (III), and (IIIA):

(A) is phenyl which is substituted with one to three groups independently selected from the group consisting of chloro, fluoro, $NR^6R^7$, and $NHC(O)OR^6$.

In an alternative the immediately preceding embodiment, (A) is phenyl which is substituted with fluoro.

In another alternative of this embodiment, is phenyl which is substituted with $NH_2$ or $NHC(O)OR^6$, wherein $R^6$ is hydrogen or methyl.

In another embodiment, in each of Formulas (I), (IA), (II), (IIA), (III), and (IIIA):

(A) is

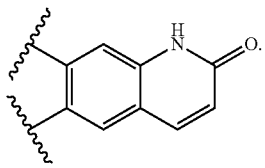 [SMILES: *c1cc2ccc(=O)[nH]c2cc1*]

In another embodiment, in each of Formulas (I), (IA), (II), (IIA), (III), and (IIIA):

(A) is

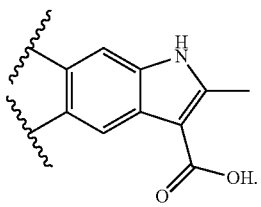 [SMILES: *c1cc2[nH]c(C)c(C(=O)O)c2cc1*]

The following alternative embodiments of (B) are contemplated in combination with any of the embodiments described hereinabove.

In another embodiment, in each of Formulas (I), (IA), (II), (IIA), (III), and (IIIA):

(B) is selected from the group consisting of phenyl, pyridinyl, oxazolyl, pyrazolyl, and imidazoyl, wherein each said phenyl, pyridinyl, and imidazoyl, is unsubtituted or substituted with one to three groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In another embodiment, in each of Formulas (I), (IA), (II), (IIA), (III), and (IIIA):

(B) is phenyl which is unsubtituted or substituted with one to three groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In another embodiment, in each of Formulas (I), (IA), (II), (IIA), (III), and (IIIA):

(B) is pyridinyl which is unsubtituted or substituted with one to three groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In another embodiment, in each of Formulas (I), (IA), (II), (IIA), (III), and (IIIA):

(B) is imidazoyl which is unsubtituted or substituted with one or two groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In another embodiment, in each of Formulas (I), (IA), (II), (IIA), (III), and (IIIA):

(B) is pyrazolyl which is unsubtituted or substituted with one or two groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In another embodiment, in each of Formulas (I), (IA), (II), (IIA), (III), and (IIIA): (B) is oxazolyl which is unsubstituted or substituted with one or two groups independently selected from the group consisting of halo, cyano, oxo, $R^6$, $OR^6$, $C(O)OR^6$, $C_{1-3}$ alkyl-$C(O)OR^6$, $C(O)NR^6R^7$ and $NR^6R^7$.

In an alternative of the immediately preceding embodiment, (B) is phenyl which is unsubstituted or substituted with fluoro or $NHC(O)OR^6$, wherein $R^6$ is hydrogen methyl, or $NH_2$.

Specific embodiments of the present invention include, but are not limited to the compounds identified in the Examples below, or stereoisomers thereof, or pharmaceutically acceptable salts of said Examples and said stereoisomers thereof.

Also included within the scope of the present invention is a pharmaceutical composition which is comprised of a compound of any one of Formulas (I), (IA), (II), (IIA), (III), or (IIIA), or according to any one of the Example compounds described below, or a stereoisomer thereof, or a pharmaceutically acceptable salt of said compound or said stereoisomer and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma kallikrein.

It will be understood that, as used herein, references to the compounds of the invention are meant to also include the pharmaceutically acceptable salts, and also salts that are not pharmaceutically acceptable when they are used as precursors to the free compounds or their pharmaceutically acceptable salts or in other synthetic manipulations.

As noted above, the compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of the invention simultaneously contain acidic and basic groups in the molecule the invention also includes, in addition to the salt forms mentioned, inner salts or betaines (zwitterions).

The present invention encompasses all stereoisomeric forms of the compounds of the invention. Unless a specific stereochemistry is indicated, the present invention is meant to comprehend all such isomeric forms of these compounds. Centers of asymmetry that are present in the compounds of the invention can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that enantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

Unless a specific enationmer or diastereomer is indicated, the invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of the invention or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof of the compounds of of the invention are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formulas (I), (IA), (II), (IIA), (III), and (IIIA) or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the term "alkyl" is intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or CH3 or a symbol that is an extended bond as the terminal group, e.g.

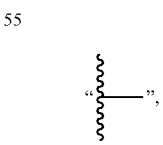

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

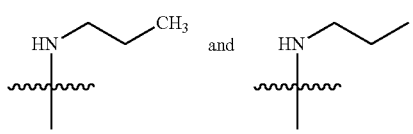

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline, and 3-oxo-3,4dihydro-2Nbenzo[b][1,4] thiazine. If the heteroaryl contains nitrogen atoms, it is understood that the corresponding N-oxides thereof are also encompassed by this definition. Where chemically permitted, each of the above-named heteroaryl groups may optionally be substituted with oxo. One further non-limiting example of an oxo-substituted heteroaryl group includes the moiety

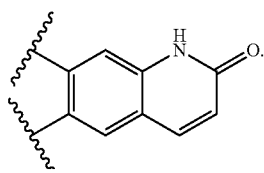 [SMILES: *c1cc2ccc(=O)[nH]c2cc1*]

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "celite".

Except where noted herein, structures containing substituent variables such as variable "R" below:

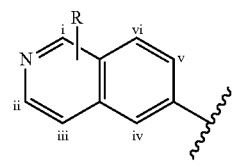

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compounds of Formula I, Formula Ib and Formula Ib, acting as prodrugs and solvates. Prodrugs, following administration to the patient, are converted in the body by normal metabolic or chemical processes, such as through hydrolysis in the blood, to the compound of the invention. Such prodrugs include those that demonstrate enhanced bioavailability, tissue specificity, and/or cellular delivery, to improve drug absorption of the compound of the invention. The effect of such prodrugs may result from modification of physicochemical properties such as lipophilicity, molecular weight, charge, and other physicochemical properties that determine the permeation properties of the drug.

The preparation of pharmaceutically acceptable salts from compounds of the invention capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the invention form stable alkali metal, alkaline earth metal or optionally substituted ammonium salts. If the compounds of the invention have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the invention and/or a pharmaceutically acceptable salt thereof and/or a stereoisomeric form of the compound of the invention or a pharmaceutically acceptable salt thereof, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably between 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the invention can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

GENERAL SCHEMES AND EXAMPLES

The following is a list of abbreviations used in the description of the Schemes and synthesis of the intermediates and examples shown below.
ACN=Acetonitrile
BOC=Di-tert-butyl dicarbonate
DEA=diethylamine
DMF=dimethylformamide
DCM=dichloromethane
DIPEA=diisopropylethylamine
EtOAc=ethyl acetate
EDC=N-(3-Dimethylaminopropyl)-N'-ethylcarbodiimide hydrochloride
DCE=1,2-dichloroethane
RP HPLC=Reverse Phase High Pressure Liquid Chromatography
Hex=hexanes
HOBt=Hydroxybenzotriazole
LDA=lithium diisopropylamide
$MgSO_4$=magnesium sulfate
pTSA=p-toluenesulfonic acid monohydrate
RBF=round-bottom flask
rt or RT=room temperature
THF=tetrahydrofuran
NMP=N-Methyl-2-pyrrolidone
$Pd(OAc)_2$=Palladium (II) acetate
SEM-Cl=2-(Trimethylsilyl)ethoxymethyl chloride
T3P=2,4,6-Tripropyl-1,3,5,2,4,6-trioxatriphosphorinane-2,4,6-trioxide
TFA=Trifluoroacetic acid
Zhan Catalyst 1B=1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride
HATU=2-(1H-7-Azabenzotriazol-1-yl)-1,1,3,3-tetramethyluronium hexafluorophosphate Methanaminium
Me=Methyl
Et=Ethyl
PE=Petroleum ether
PPT=precipitates
SFC=supercritical fluid chromatography Also, TLC is thin layer chromatography; UV is ultraviolet; W is watts; wt. % is percentage by weight; x g is times gravity; $\alpha_D$ is the specific rotation of polarized light at 589 nm; ° C. is degrees Celsius; % w/v is percentage in weight of the former agent relative to the volume of the latter agent.

LCMS Condition

System: Waters Acquity UPLC/MS, Electrospray positive ion mode; Column: Waters Acquity UPLC BEH C18, 2.1× 50 mm, 1.7 micron; Mobile Phase: A: $H_2O$/0.05% TFA, B: ACN/0.05% TFA; Gradient: 0-1.8 min, 5-99% B; Flow Rate: 0.8 mL/min; UV: 254 nm.

Preparation of Spirocarbamate Ring

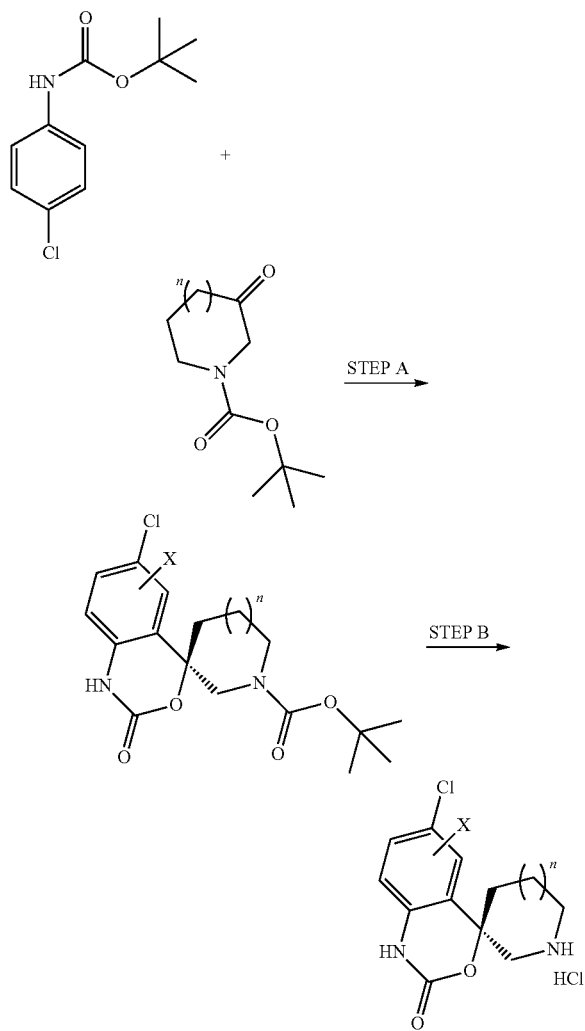

All spirocarbamate rings were prepared by using a procedure described in *J. Am. Chem. Soc.* 2008, 47, 3690-3699.

Step A: tert-Butyl (R)-6-chloro-2-oxo-1,2-dihydrospiro[benzo[d][1,3]oxazine-4,3'-piperidine]-1'-carboxylate To a stirred solution of tert-butyl (4-chlorophenyl)carbamate (3 g, 13.18 mmol) in $Et_2O$ (20 ml) was added tert-buthyllithium (18.60 ml, 31.6 mmol) (1.7 M in pentane) dropwise at −40° C. The reaction mixture was stirred below −15° C. for 3.5 hrs. After cooled down to −78° C., lanthanum trichloride-lithium chloride complex (24.16 ml, 14.49 mmol) (0.6M in THF) was added dropwise into the reaction mixture. After 5 min at −78° C., a solution of tert-butyl 3-oxopiperidine-1-carboxylate (3.15 g, 15.81 mmol) in THF (7 ml) was added rapidly into the reaction mixture. The reaction mixture was warmed to RT over 1 hr. The reaction mixture was stirred at RT for overnight. Potassium tert-butoxide (0.148 g, 1.318 mmol) was added into the reaction mixture and the reaction mixture was heated to 60° C. for 6 hrs. After cooled down to RT, the reaction mixture was diluted with EtOAc (200 mL). The organic layer was washed with 1N HCl, sat. aq. $NH_4Cl$ and aq. $NaHCO_3$ and brine. The organic layer was dried over $MgSO_4$, filtered and concentrated. The crude product was purified by flash silica gel column chromatography (EtOAc/Hex=1/1) to give tert-butyl 6-chloro-2-oxo-1,2-dihydrospiro[pyrido[2,3-d][1,3]oxazine-4,3'-pyrrolidine]-1'-carboxylate. LC/MS=297 [M-55]. The mixture of the two stereoisomers was purified by chiral SFC (OJ-H column, 10% methanol/$CO_2$, 100 bar) to afford isomer A (first peak, S configuration) and B (second peak, R configuration).

Step B: (R)-6-Chlorospiro[benzo[d][1,3]oxazine-4, 3'-piperidin]-2(1H)-one hydrochloride To a round bottom flask charged with tert-butyl 6-chloro-2-oxo-1,2-dihydrospiro[pyrido[2,3-d][1,3]oxazine-4,3'-pyrrolidine]-1'-carboxylate (705 mg, 1.998 mmol) added 4N HCl in 1,4-dioxane (4.9 ml, 19.98 mmol) and stirred at RT for 2 hrs. The reaction mixture was concentrated by a rotary evaporator. The crude product was dried in a vac. oven overnight and used for the next step without further purification. LC/MS=253 [M+1].

Intermediate 1

2-(5,5-Dimethyl-1,3,2-dioxaborinan-2-yl)-5-nitroaniline

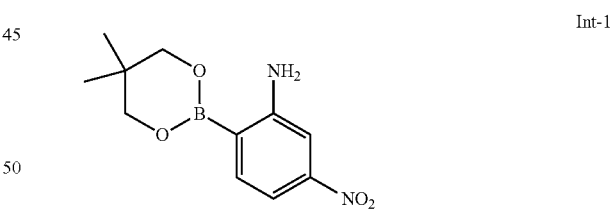

Int-1

To a round bottom flask containing 2-bromo-5-nitroaniline (5 g, 23.04 mmol), bis(neopentyl glycolato)diboron (6.51 g, 28.8 mmol), potassium accetate (6.78 g, 69.1 mmol), and 1,1'-bis(diphenylphosphino)ferrocene-Palladium (II) dichloride DCM complex (0.470 g, 0.576 mmol), was added DMSO (80 mL). The resulting suspension was degassed with $N_2$ for 30 min, and then reaction was warmed to 80° C. (under $N_2$). After 4 hours, the reaction was stopped and cooled to r.t. The reaction was poured slowly to vigorously stirred ice-cold water (150 mL) to give a suspension. After stirring for 10 min, the suspension was filtered to collect the solid. The solid was rinsed with water (3×50 mL), air dried and then dried under a vacuum to give the crude product. The crude product was purified by flash column chromatography on silica gel (0-100% EtOAc in hexane) to give the title compound. LC/MS=183 (M-C$_5$H$_8$+1).

Intermediate 2 tert-Butyl (3-amino-4-(4,4,5,5-tetramethyl-1,3,2-dioxaborolan-2-yl)phenyl)carbamate

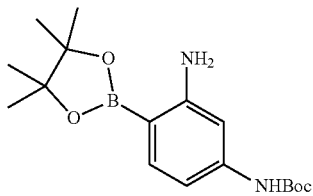

Int-2

Step A: tert-Butyl (4-bromo-3-nitrophenyl)carbamate

To a solution of 4-bromo-3-nitroaniline (20 g, 92 mmol) and di-tert-butyl dicarbonate (26.1 g, 120 mmol) in THF (250 mL) at 0° C. was added DMAP (5.63 g, 46.1 mmol) and TEA (51.4 mL, 369 mmol). The reaction mixture was stirred at 15° C. for 12 h. TLC showed the starting material consumed. The resulting mixture was concentrated. The residue was diluted with water (200 mL) and extracted with EtOAc (200 mL×4). The combined organic layers were dried over Na$_2$SO$_4$, filtered and concentrated. The residue was further purified by flash column chromatography on silica gel (Hex:EtOAc=10:1) to give the title compound. $^1$H NMR (CDCl$_3$, 400 MHz): δ 8.05 (d, J=2.0 Hz, 1H), 7.61 (d, J=8.8 Hz, 1H), 7.39 (d, J=6.9 Hz, 1H), 6.67 (br. s., 1H), 1.53 (s, 9H).

Step B: tert-Butyl (3-amino-4-bromophenyl)carbamate

To a round bottom flask was added tert-butyl (4-bromo-3-nitrophenyl)carbamate (10 g, 31.5 mmol), EtOH (200 mL), water (40 mL), ammonia hydrochloride (16.87 g, 315 mmol) and iron powders (17.61 g, 315 mmol). The reaction mixture was stirred at 80° C. for 2 h. TLC showed the starting material was consumed completely. The resulting mixture was filtered and concentrated. The residue was diluted with water (100 mL) and extracted with EtOAc (200 mL×3). The combined organic layers was dried over Na$_2$SO$_4$, filtered and concentrated to give the title compound which was used for next step without further purification. $^1$H NMR (CDCl$_3$, 400 MHz): δ 7.25 (d, J=8.4 Hz, 1H), 6.29-6.49 (m, 2H), 4.08 (br. s., 2H), 1.45-1.55 (m, 9H).

Step C: tert-Butyl (3-amino-4-(4,4,5,5-tetramethyl-1,3,2-dioxaborolan-2-yl)phenyl)carbamate To a mixture of tert-butyl (3-amino-4-bromophenyl)carbamate (7.2 g, 25.07 mmol), 4,4,4',4',5,5,5',5'-octamethyl-2,2'-bi(1,3,2-dioxaborolane) (6.37 g, 25.07 mmol) in 1,4-dioxane (250 mL) was added potassium acetate (7.38 g, 75 mmol) and PdCl$_2$(dppf) (0.917 g, 1.254 mmol). The reaction mixture was stirred at 100° C. for 12 h under N$_2$ protection. The resulting mixture was filtered and concentrated. The residue was purified by column chromatography (SiO$_2$, PE:EtOAc=5:1) to give the title compound. $^1$H NMR (CDCl$_3$, 400 MHz): δ 7.03 (t, J=8.1 Hz, 1H), 6.54 (d, J=7.9 Hz, 1H), 6.36 (dd, J=7.9, 1.3 Hz, 1H), 1.50 (s, 9H), 1.26 (br. s., 12H).

Intermediate 3

2-Bromo-1-(2-bromo-4-fluorophenyl)ethan-1-one

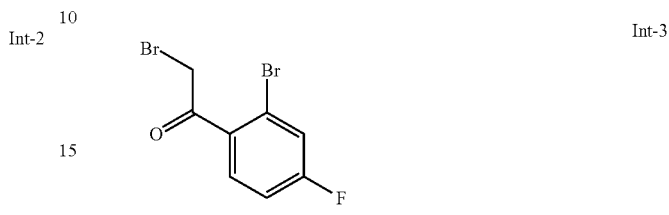

Int-3

To a stirred solution of 2'-bromo-4'-fluoroacetophenone (5.00 g, 23.04 mmol) and HBr (0.2 ml, 1.768 mmol) in diethyl ether (50 ml) at 0° C. was added bromine (1.2 ml, 23.29 mmol) dropwise. The resulting solution was stirred at rt overnight. It was washed with water (50 mL) and brine (2×50 mL). The combined aqueous layers were extracted with diethyl ether (100 mL), dried over sodium sulfate, filtered and concentrated under reduced pressure. The residue was purified by flash column chromatography on silica gel (0-20% ethyl acetate in hexane) to give the title compound. LC/MS=297 [M+1]

Intermediate 4

2,5-Dioxopyrrolidin-1-yl but-3-enoate

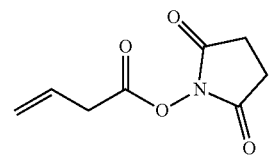

Int-4

To a stirred solution of but-3-enoic acid (2.00 g, 23.23 mmol) in DCM (40 mL) was added N-hydroxysuccinimide (2.91 g, 25.3 mmol), N,N'-dicyclohexylcarbodiimide (4.99 g, 24 mmol) at RT under nitrogen atmosphere. The resulting mixture was stirred at 0° C. to room temperature for 18 h. The reaction mixture was filtered (to remove urea derivative). The filtrate washed with sat. NaHCO$_3$ (75 ml), dried over Na$_2$SO$_4$, filtered, concentrated under reduced pressure to obtained the title compound $^1$H NMR (CDCl$_3$, 400 MHz): δ 5.91 (m, 1H), 5.32 (m, 2H), 3.38 (d, 2H), 2.84 (s, 4H).

Intermediate 5

(R)-2-Methylbut-3-enoic Acid

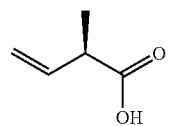

Int-5

Step A: (R)-4-Benzyl-3-(but-3-enoyl)oxazolidin-2-one

To a mixture of but-3-enoic acid (8 g, 93 mmol) and 4-methylmorpholine (11.24 mL, 102 mmol) in THF (80 mL) at 0° C. was added dropwise pivaloyl chloride (11.20 g, 93 mmol). The mixture was cooled to −78° C. and stirred for 2 h. In a separate flask, n-BuLi (40.9 mL, 102 mmol) (2.5M in hexane) was added dropwise to a solution of (R)-4-benzyloxazolidin-2-one (16.47 g, 93 mmol) in THF (170 mL) at −78° C. After further stirring for 35 min, this mixture was transferred via canula to the first mixed anhydride mixture. The combined reaction mixture was stirred at −78° C. for 2 hrs. TLC (SiO$_2$, PE: EtOAc=5:1) showed the reaction was complete. The cold bath was removed and the mixture was quenched with aqueous ammonium chloride (saturated, 50 mL) and extracted with EtOAc (3×150 mL). The combined organic fractions were washed with brine (150 mL), dried (Na$_2$SO$_4$), filtered and evaporated under reduced pressure. The crude product was purified by flash column chromatography on silica gel (0-15% EtOAc/PE) to give the title compound. LC/MS=246.2 [M+H].

Step B: (R)-4-Benzyl-3-((R)-2-methylbut-3-enoyl)oxazolidin-2-one

To a stirred solution of diisopropylamine (4.08 g, 40.4 mmol) in THF (80 mL) at −78° C. was added n-BuLi (16.15 mL, 40.4 mmol) (2.5M in hexane). After 10 min, HMPA (7.02 mL, 40.4 mmol) was added and the mixture was stirred for 30 min at −78° C. A solution of (R)-4-benzyl-3-(but-3-enoyl)oxazolidin-2-one (9 g, 36.7 mmol) in THF (70 mL) was added and stirred for 15 min. MeI (7.13 mL, 114 mmol) was then added and stirred at −78° C. for 20 min. The mixture was allowed to warm to −10° C. and stirred at this temperature for 90 min. TLC (SiO$_2$, PE: EtOAc=5:1) showed the reaction was nearly complete. The mixture was quenched with hydrochloric acid (1M, 50 mL) and extracted with EtOAc (3×60 mL). The combined organic fractions were washed with brine (60 mL), dried (Na$_2$SO$_4$), filtered and evaporated under reduced pressure. The residue was purified by flash column chromatography on silica gel (80 g, 0~15% EtOAc/PE gradient @ 60 mL/min) to give the title compound. LC/MS=260.2 [M+1].
$^1$H NMR (CDCl$_3$, 400 MHz): δ 7.27-7.37 (m, 3H), 7.21 (d, J=7.0 Hz, 2H), 5.98 (ddd, J=7.8, 10.0, 17.4 Hz, 1H), 5.10-5.25 (m, 2H), 4.65 (tt, J=3.4, 6.4 Hz, 1H), 4.16-4.22 (m, 2H), 3.28 (dd, J=2.9, 13.5 Hz, 1H), 2.78 (dd, J=9.8, 13.3 Hz, 1H), 1.34 (d, J=7.0 Hz, 3H).

Step C: (R)-2-Methylbut-3-enoic Acid

To a clear solution of (R)-4-benzyl-3-((R)-2-methylbut-3-enoyl)oxazolidin-2-one (1 g, 3.86 mmol) in THF (24 mL) at 0° C. was added dropwise H$_2$O$_2$ (1.576 mL, 15.43 mmol) (30% aq.), followed by LiOH (3.86 mL, 7.71 mmol) (2M aq.). The reaction was then stirred at 0° C. for 30 min. The reaction was quenched with Na$_2$SO$_3$ (4.2 mL, saturated, aq.) and NaHCO$_3$ (4.2 mL, saturated, aq.). The reaction was then concentrated to remove THF. The residue was diluted with water and washed with CHCl$_3$ (3×25 mL). The aqueous layer was acidified with concentrated HCl to pH 3 and extracted with EtOAc (3×30 mL). The combined organic fractions were washed with brine (30 mL), dried (Na$_2$SO$_4$), filtered and evaporated under reduced pressure to give the title compound.

$^1$H NMR (CDCl$_3$, 400 MHz): δ 5.94 (ddd, J=7.4, 10.1, 17.3 Hz, 1H), 5.11-5.24 (m, 2H), 3.19 (t, J=7.2 Hz, 1H), 1.31 (d, J=7.0 Hz, 3H).

Example 1

Methyl ((R,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate EX-1a Methyl ((S,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate EX-1b EX-1a and 1b

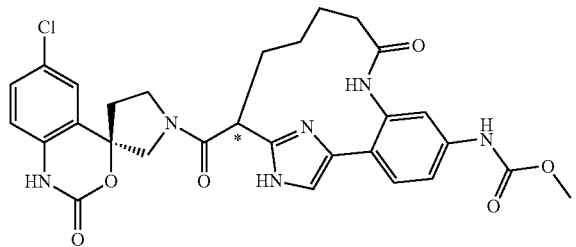

Synthetic Scheme for Example 1

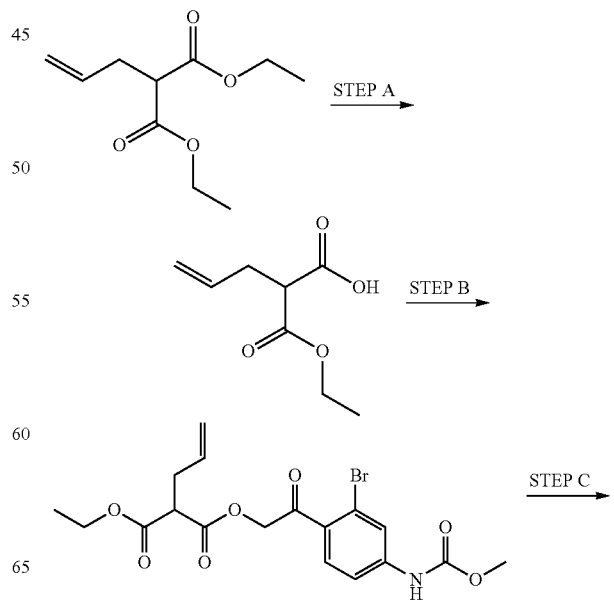

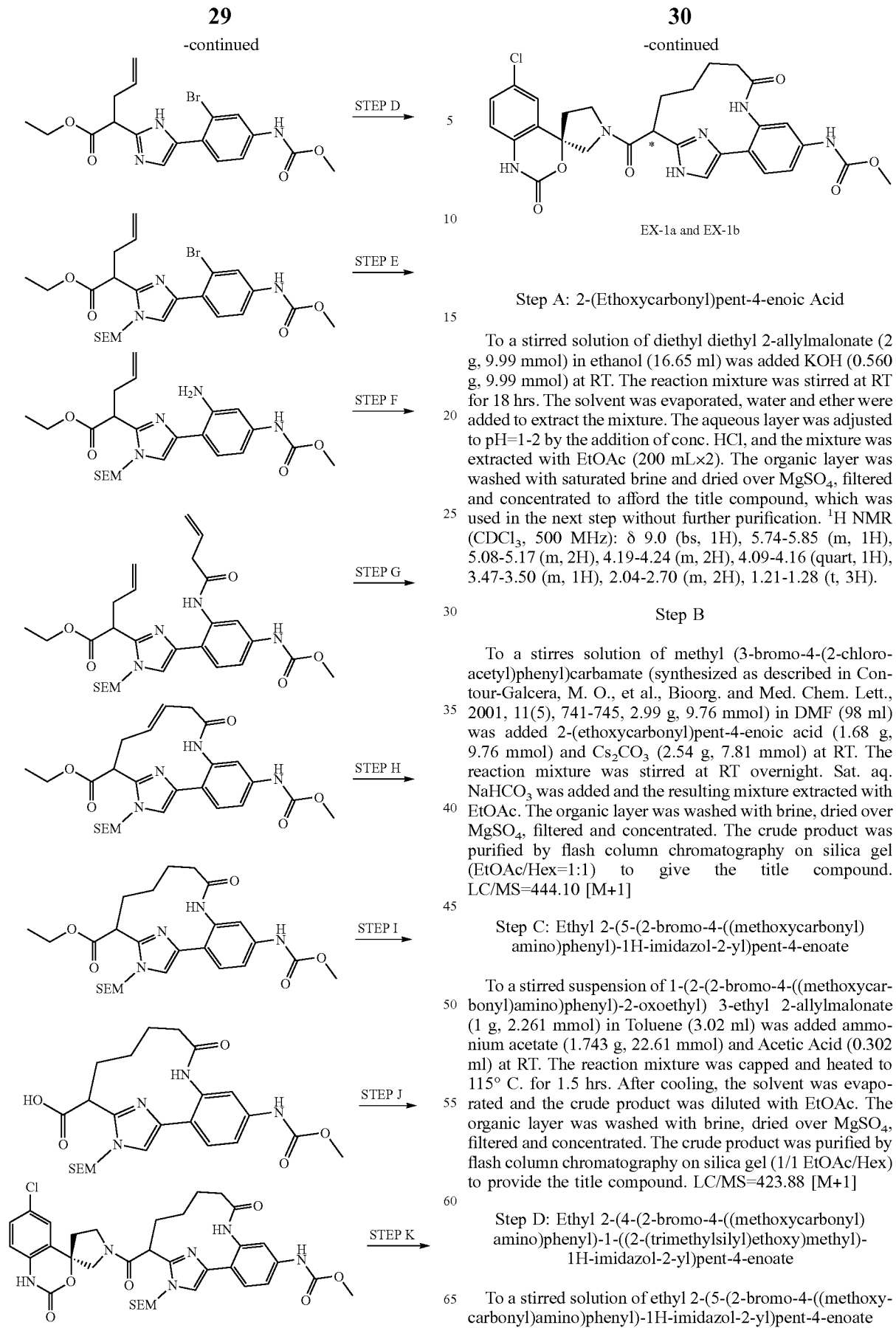

EX-1a and EX-1b

Step A: 2-(Ethoxycarbonyl)pent-4-enoic Acid

To a stirred solution of diethyl diethyl 2-allylmalonate (2 g, 9.99 mmol) in ethanol (16.65 ml) was added KOH (0.560 g, 9.99 mmol) at RT. The reaction mixture was stirred at RT for 18 hrs. The solvent was evaporated, water and ether were added to extract the mixture. The aqueous layer was adjusted to pH=1-2 by the addition of conc. HCl, and the mixture was extracted with EtOAc (200 mL×2). The organic layer was washed with saturated brine and dried over MgSO$_4$, filtered and concentrated to afford the title compound, which was used in the next step without further purification. $^1$H NMR (CDCl$_3$, 500 MHz): δ 9.0 (bs, 1H), 5.74-5.85 (m, 1H), 5.08-5.17 (m, 2H), 4.19-4.24 (m, 2H), 4.09-4.16 (quart, 1H), 3.47-3.50 (m, 1H), 2.04-2.70 (m, 2H), 1.21-1.28 (t, 3H).

Step B

To a stirres solution of methyl (3-bromo-4-(2-chloroacetyl)phenyl)carbamate (synthesized as described in Contour-Galcera, M. O., et al., Bioorg. and Med. Chem. Lett., 2001, 11(5), 741-745, 2.99 g, 9.76 mmol) in DMF (98 ml) was added 2-(ethoxycarbonyl)pent-4-enoic acid (1.68 g, 9.76 mmol) and Cs$_2$CO$_3$ (2.54 g, 7.81 mmol) at RT. The reaction mixture was stirred at RT overnight. Sat. aq. NaHCO$_3$ was added and the resulting mixture extracted with EtOAc. The organic layer was washed with brine, dried over MgSO$_4$, filtered and concentrated. The crude product was purified by flash column chromatography on silica gel (EtOAc/Hex=1:1) to give the title compound. LC/MS=444.10 [M+1]

Step C: Ethyl 2-(5-(2-bromo-4-((methoxycarbonyl)amino)phenyl)-1H-imidazol-2-yl)pent-4-enoate To a stirred suspension of 1-(2-(2-bromo-4-((methoxycarbonyl)amino)phenyl)-2-oxoethyl) 3-ethyl 2-allylmalonate (1 g, 2.261 mmol) in Toluene (3.02 ml) was added ammonium acetate (1.743 g, 22.61 mmol) and Acetic Acid (0.302 ml) at RT. The reaction mixture was capped and heated to 115° C. for 1.5 hrs. After cooling, the solvent was evaporated and the crude product was diluted with EtOAc. The organic layer was washed with brine, dried over MgSO$_4$, filtered and concentrated. The crude product was purified by flash column chromatography on silica gel (1/1 EtOAc/Hex) to provide the title compound. LC/MS=423.88 [M+1]

Step D: Ethyl 2-(4-(2-bromo-4-((methoxycarbonyl)amino)phenyl)-1-((2-(trimethylsilyl)ethoxy)methyl)-1H-imidazol-2-yl)pent-4-enoate To a stirred solution of ethyl 2-(5-(2-bromo-4-((methoxycarbonyl)amino)phenyl)-1H-imidazol-2-yl)pent-4-enoate (354 mg, 0.838 mmol) in DMF (838 μl) was added SEM-Cl (163 µl, 0.922 mmol) and DIPEA (190 µl, 1.090 mmol) at RT. The reaction mixture was stirred at RT overnight. Sat. NaHCO$_3$ was poured into the reaction mixture and the reaction mixture was diluted with EtOAc. The organic layer was washed with brine, dried over MgSO$_4$, filtered and concentrated. The crude product was purified by flash column chromatography on silica gel (1/1 EtOAc/Hex) to give the title compound. LC/MS=553.8 [M+1]

Step E: Ethyl 2-(4-(2-amino-4-((methoxycarbonyl)amino)phenyl)-1-((2-(trimethylsilyl)ethoxy)methyl)-1H-imidazol-2-yl)pent-4-enoate To a stirred solution of ethyl 2-(4-(2-bromo-4-((methoxycarbonyl)amino)phenyl)-1-((2-(trimethylsilyl)ethoxy)methyl)-1H-imidazol-2-yl)pent-4-enoate (302 mg, 0.547 mmol) in DMSO (1093 µl) was added L-PROLINE (25.2 mg, 0.219 mmol), cuprous iodide (20.82 mg, 0.109 mmol), K$_2$CO$_3$ (227 mg, 1.640 mmol) at RT. The microwave tube was evacuagted and back-filled with N$_2$ three times. Then 28% ammonium hydroxide (76 µl, 0.547 mmol) was added. The tube was capped and the reaction mixture was heated to 85° C. overnight. The reaction mixture was then cooled to RT, diluted with EtOAc. The organic layer was washed with water, brine and dried over sodium sulfate, filtered and concentrated. The crude product was purified by flash column chromatography on silica gel (30-60% EtOAc: Hexanes) to give the title compound. LC/MS=489 [M+1]

Step F: Ethyl 2-(4-(2-(but-3-enamido)-4-((methoxycarbonyl)amino)phenyl)-1-((2-(trimethylsilyl)ethoxy)methyl)-1H-imidazol-2-yl)pent-4-enoate To a stirred solution of ethyl 2-(4-(2-amino-4-((methoxycarbonyl)amino)phenyl)-1-((2-(trimethylsilyl)ethoxy)methyl)-1H-imidazol-2-yl)pent-4-enoate (154.3 mg, 0.316 mmol) in DMF (1579 µl) was added vinylacetic acid (31.9 µl, 0.379 mmol), HATU (144 mg, 0.379 mmol) and DIPEA (110 µl, 0.632 mmol) at RT. The reaction mixture was stirred at RT overnight. Aq. sat. NaHCO$_3$ was poured into the reaction and the reaction mixture was extracted with EtOAc. The organic layer was washed with brine and dried over MgSO$_4$, filtered and concentrated. The crude product was purified by flash column chromatography on silica gel (1/1 EtOAc/Hex) to give the title compound. LC/MS=557.0 [M+1]

Step G: Ethyl (1$^2$Z,6E)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate To a microwave tube containing ethyl 2-(4-(2-(but-3-enamido)-4-((methoxycarbonyl)amino)phenyl)-1-((2-(trimethylsilyl)ethoxy)methyl)-1H-imidazol-2-yl)pent-4-enoate (153.9 mg, 0.276 mmol) in DCE (6911 µl) was added Zhan Catalyst 1B (40.6 mg, 0.055 mmol) and pTSA (52.6 mg, 0.276 mmol) at RT. The reaction mixture was degassed (×3) and filled with N$_2$ and capped and heated to 75° C. for 4 hrs. The reaction solvent was evaporated and the crude product was purified by flash column chromatography on silica gel (1/1/EtOAc/Hex) to give the title compound. LC/MS=529 [M+1]

Step H: Ethyl (Z)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylate To a stirred solution of ethyl (1$^2$Z,6E)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate (61 mg, 0.115 mmol) in EtOAc (2885 µl) and MeOH (2885 µl) was added Pd—C(36.8 mg, 0.035 mmol) (10% activated) at RT. H$_2$ balloon was equipped to the reaction mixture and the reaction mixture was stirred at RT overnight. The reaction mixture was filtered through a pad of Celite and washed with EtOAc. The filtrate was evaporated and the crude product was isolated by flash column chromatography on silica gel (1/1EtOAc/Hex) to give the title compound. LC/MS=530.99 [M+1]

Step I: (Z)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylic Acid To a solution of ethyl (Z)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylate (59 mg, 0.111 mmol) in THF (1 mL) was added a solution of LiOH H$_2$O (5.13 mg, 0.122 mmol) in water (200 µL) and MeOH (200 µL) at RT. The reaction mixture was stirred at RT for 4 hrs. 1N HCl was added until pH=6.5. The solvent was evaporated and the crude product was dried under vac. oven overnight to afford the title compound. LC/MS=502.99 [M+1]

Step J: Methyl ((Z)-9-((R)-6-chloro-2-oxo-1,2-dihydrospiro[benzo[d][1,3]oxazine-4,3'-pyrrolidine]-1'-carbonyl)-4-oxo-1$^1$-((2-(trimethylsilyl)ethoxy)methyl)-1$^1$H-3-aza-1(4,2)-imidazola-2(1,2)-benzenacyclononaphane-24-yl)carbamate To a stirred solution of (Z)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylic acid (56.5 mg, 0.112 mmol) in DMF (1124 µl) was added (R)-6-chlorospiro[benzo[d][1,3]oxazine-4,3'-pyrrolidin]-2(1H)-one hydrochloride (40.2 mg, 0.169 mmol), HATU (64.1 mg, 0.169 mmol) and DIPEA (58.9 µl, 0.337 mmol) at RT. The reaction mixture was stirred at RT for 4 hrs. Saturated aq. NaHCO$_3$ was added into the reaction mixture and extracted with EtOAc. The organic layer was washed with brine, dried over MgSO$_4$, filtered and concentrated. The crude product was purified by flash column chromatography on silica gel (1/1=EtOAc/Hex to 100% EtOAc) to give the title compound. LC/MS=723.0 [M+1]

Step K: Methyl ((R,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate (EX-1a) and Methyl ((S,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate (EX-1b To a microwave tube containing methyl ((Z)-9-((R)-6-chloro-2-oxo-1,2-dihydrospiro[benzo[d][1,3]oxazine-4,3'-pyrrolidine]-1'-carbonyl)-4-oxo-1$^1$-((2-(trimethylsilyl)ethoxy)methyl)-1$^1$H-3-aza-1(4,2)-imidazola-2(1,2)-benzenacyclononaphane-24-yl)carbamate (77.8 mg, 0.108 mmol) was added HCl (538 µl, 2.151 mmol) (4N in dioxane) at RT. The tube was capped and heated to 50° C. overnight. After cooling down to RT, the solvent was evaporated. EtOAc (100 mL) and sat. NaHCO$_3$ were added. The aq layer was extracted with EtOAc and 10% MeOH/DCM. The organic layer was dried over MgSO₄, filtered and concentrated. The crude product was purified by flash column chromatography on silica gel (0-100% EtOAc in Hex and 10% MeOH in DCM) to afford the diastereomer mixtures. The two diastereomers were resolved by chiral SFC separation (OD-H column, 65% 2:1 MeOH:MeCN/CO₂, 100 bar, 220 nm) to provide Example 1a (first peak). LC/MS=593 [M+1] and Example 1b (second peak). LC/MS=593 [M+1]

Example 2

(R)-6-Chloro-1¹-((R,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-piperidin]-2(1H)-one (EX-2a) and (R)-6-Chloro-1'-((S,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-piperidin]-2(1H)-one EX-2b Synthetic Scheme for Example 2

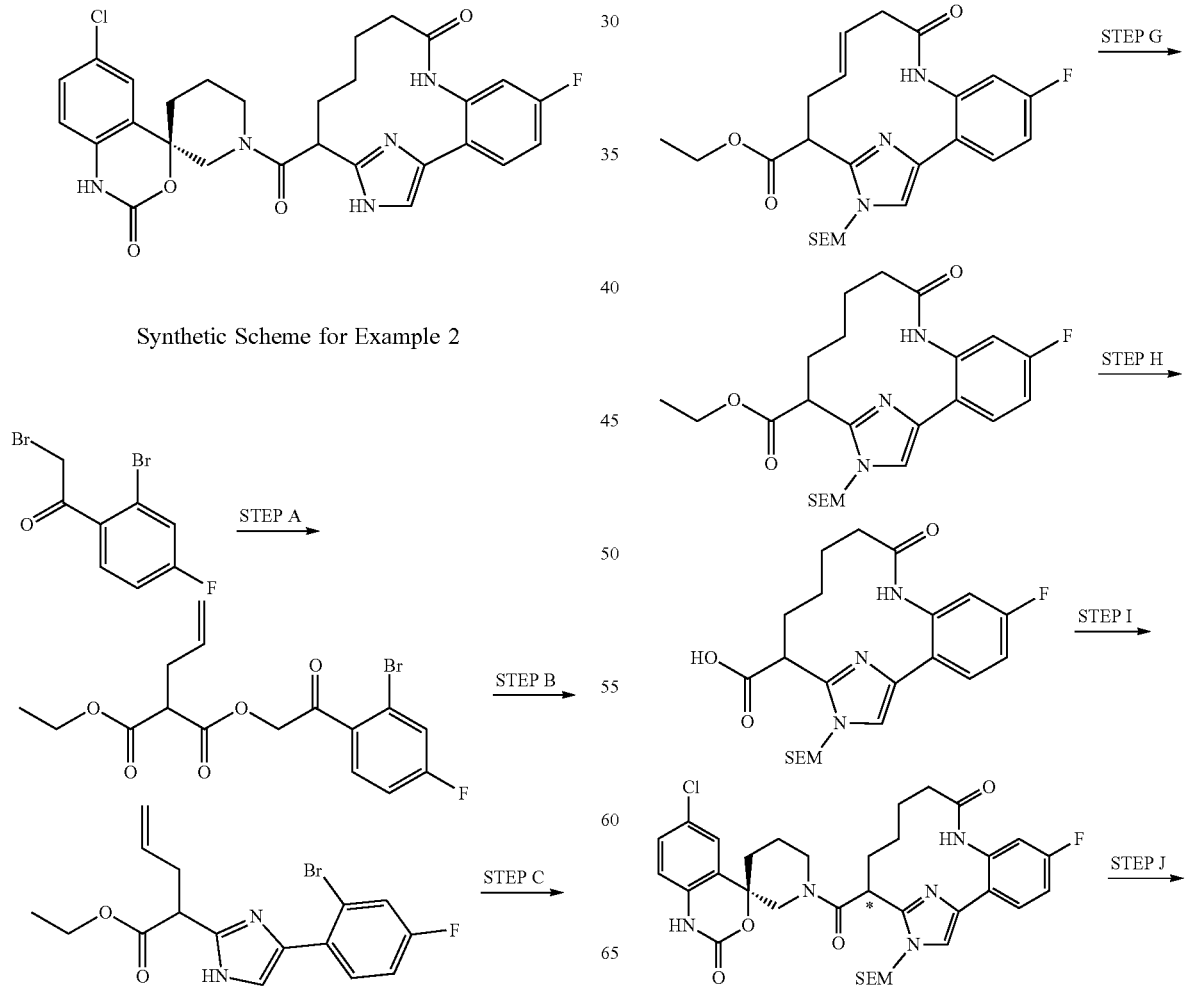

-continued

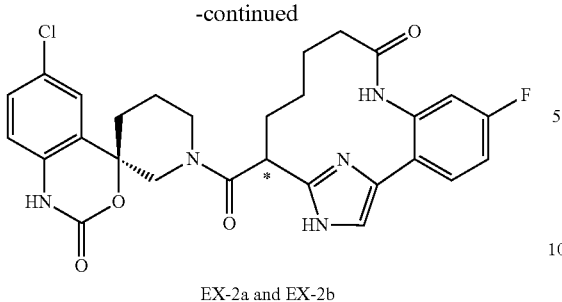

EX-2a and EX-2b

Step A: 1-(2-(2-Bromo-4-fluorophenyl)-2-oxoethyl) 3-ethyl 2-allylmalonate

To a stirred solution of 2-(ethoxycarbonyl)pent-4-enoic acid (4.0 g, 23.23 mmol) in anhydrous DMF (25 ml) at 0° C. was added 2-bromo-1-(2-bromo-4-fluorophenyl)ethanone (6.87 g, 23.23 mmol) and $Cs_2CO_3$ (7.57 g, 23.23 mmol) slowly in small portions. It was stirred for 10 min and allowed to warm to rt overnight. The mixture was filtered through a pad of Celite and the solid was rinsed with ethyl acetate. The filtrate was concentrated under reduced pressure. The residue was dissolved in diethyl ether (100 mL) and washed sequentially with water (3×100 mL) and brine (100 mL). The organic layer was seperated, dried over sodium sulfate, fitlered and concentrated in vacuo. The residue was purified by flash column chromatography on silica gel (0-50% ethyl acetate in hexane) to the title compound. MS (ES+) m/z: 387, 389 (M+1); $^1$H NMR (CDCl$_3$, 500 MHz,): δ 7.60 (dd, 1H), 7.41 (dd, 1H), 7.13-7.17 (m, 1H), 5.81 (m, 1H), 5.07-5.26 (m, 4H), 4.24 (q, 2H), 3.59 (t, 1H), 2.71 (t, 2H), 1.29-1.33 (t, 3H).

Step B: Ethyl 2-(4-(2-bromo-4-fluorophenyl)-1H-imidazol-2-yl)pent-4-enoate

A mixture of 1-(2-(2-bromo-4-fluorophenyl)-2-oxoethyl) 3-ethyl 2-allylmalonate (8.439 g, 21.80 mmol) and ammonium acetate (16.80 g, 218 mmol) in toluene (39.6 ml) and acetic acid (3.96 ml) were heated to reflux for 15 h. It was allowed to cool to rt and added 100 mL of ethyl acetate. The mixture was washed with 100 mL of water, saturated aqueous sodium bicarbonate and brine. The organic layer was separated, dried over sodium sulfate, filtered and concentrated under reduced pressure. The residue was purified by flash column chromatography on silica gel (0-100% ethyl acetate/ethanol in hexanes) to give the title compound as a solid. MS (ES) m/z: 367, 369 (M+H).

Step C: Ethyl 2-(4-(2-bromo-4-fluorophenyl)-1-((2-(trimethylsilyl)ethoxy)methyl)-1H-imidazol-2-yl) pent-4-enoate To a solution of ethyl 2-(4-(2-bromo-4-fluorophenyl)-1H-imidazol-2-yl)pent-4-enoate (1.60 g, 4.36 mmol) in anhydrous DMF (5 ml) was added SEM-Cl (0.8 ml, 4.51 mmol) and sodium hydride (0.192 g, 4.79 mmol). It was stirred for 20 min at rt and was quenched with saturated squeous ammonium chloride. The mixture was extracted with ethyl acetate. The organic layer was washed with water three times and brine once. It was separated and dried over sodium sulfate. The drier was removed by filtration. The filtrate was concentrated under reduced pressure. The residue was purified by flash column chromatography on silica gel (0-50% ethyl acetate in hexane) to give the title compound. MS (ES) m/z: 497, 499 (M+1).

Step D: Ethyl 2-(4-(2-amino-4-fluorophenyl)-1-((2-(trimethylsilyl)ethoxy)methyl)-1H-imidazol-2-yl) pent-4-enoate To a clean dry sealed tube loaded with a magnetic stirring bar, L-proline (0.160 g, 1.387 mmol) and potassium carbonate (0.958 g, 6.94 mmol) was added to a solution of ethyl 2-(4-(2-bromo-4-fluorophenyl)-1-((2-(trimethylsilyl) ethoxy)methyl)-1H-imidazol-2-yl)pent-4-enoate (1.15 g, 2.312 mmol) in DMSO (4.6 ml). A stream of nitrogen was bubbled through the mixture for 15 minutes. To the mixture was added cuprous iodide (0.132 g, 0.694 mmol) and ammonium hydroxide (28% aqueous, 0.35 ml, 2.52 mmol). It was sealed and heated in an oil-bath at 85° C. for 20 hrs. It was cooled to rt and diluted with ethyl acetate (100 mL). The mixture was washed with water (3×100 mL). The combined aqueous layers were extracted with ethyl acetate (100 mL). The combined organic layers were washed with brine (2×50 mL), dried over sodium sulfate, filtered and concentrated under reduced prssure. The residue was purified by flash column chromatography on silica gel (0-100% ethyl acetate in hexane) to give the title compound. MS (ES+) m/z: 434 (M+1).

Step E: Ethyl 2-(4-(2-(but-3-enamido)-4-fluorophenyl)-1-((2-(trimethylsilyl)ethoxy)methyl)-1H-imidazol-2-yl)pent-4-enoate To a solution of ethyl 2-(4-(2-amino-4-fluorophenyl)-1-((2-(trimethylsilyl)ethoxy)methyl)-1H-imidazol-2-yl)pent-4-enoate (484 mg, 1.116 mmol) and but-3-enoic acid (115 mg, 1.340 mmol) in DCM (4 ml) was added HATU (509 mg, 1.340 mmol) and DIEA (0.390 ml, 2.233 mmol) at rt. The mixture was stirred for 1 h. It was purified by flash column chromatography on silica gel (0-3% methanol in DCM) to afford the title compound. MS (ES) m/z: 502 (M+1).

Step F: Ethyl (1$^2$Z,6E)-2$^4$-fluoro-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate To a microwave tube was added ethyl 2-(4-(2-(but-3-enamido)-4-fluorophenyl)-1-((2-(trimethylsilyl)ethoxy) methyl)-1H-imidazol-2-yl)pent-4-enoate (313 mg, 0.624 mmol) and Zhan Catalyst 1B (45.8 mg, 0.062 mmol). It was sealed and purged with nitrogen three times. To the mixture was added degassed anhydrous toluene (20 mL). It was stirred at 50° C. under nitrogen for 8 h. Most solvent was removed under reduced pressure and the residue was purified by flash column chromatography on silica gel (0-70% ethyl acetate in hexane) to give the title compound. MS (ES) m/z: 474 (M+1).

Step G: Ethyl (Z)-2$^4$-fluoro-4-oxo-1$^1$-((2-(trimethylsilyl)ethoxy)methyl)-1$^1$H-3-aza-1(4,2)-imidazola-2 (1,2)-benzenacyclononaphane-9-carboxylate A mixture of palladium on carbon (10 wt %, 108 mg, 0.101 mmol) and ethyl (1$^2$Z,6E)-2$^4$-fluoro-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate (320 mg, 0.338 mmol) in EtOAc (2 mL) and MeOH (2 mL)

were stirred under H$_2$ (1 atm) overnight. It was filtered through a pad of Celite. The filtrated was concentrated under reduced pressure to give the title compound. MS (ES) m/z: 476 (M+1).

Step H: (Z)-2$^4$-Fluoro-4-oxo-1$^1$-((2-(trimethylsilyl)ethoxy)methyl)-1$^1$H-3-aza-1(4,2)-imidazola-2(1,2)-benzenacyclononaphane-9-carboxylic Acid To a solution of ethyl (Z)-2$^4$-fluoro-4-oxo-1$^1$-((2-(trimethylsilyl)ethoxy)methyl)-1$^1$H-3-aza-1(4,2)-imidazola-2(1,2)-benzenacyclononaphane-9-carboxylate (92 mg, 0.193 mmol) in THF (0.65 mL), MeOH (0.65 mL) and water (0.65 mL) was added aqueous LiOH (5 M, 0.08 mL, 0.400 mmol). It was stirred at rt for 2 h and was acidified with HCl (1 M, 2 mL) to pH 5. Most organic solvent was removed. The residue was diluted with ethyl acetate (20 mL), washed with brine, dried over sodium sulfate, filtered and concentrated under reduced pressure to give the title compound. MS (ES$^+$) m/z: 448 (M+H).

Step I: (R)-6-Chloro-1'-((R,Z)-2$^4$-fluoro-4-oxo-1$^1$-((2-(trimethylsilyl)ethoxy)methyl)-1$^1$H-3-aza-1(4,2)-imidazola-2(1,2)-benzenacyclononaphane-9-carbonyl)spiro[benzo[d][1,3]oxazine-4,3'-piperidin]-2(1H)-one A solution of (R)-6-chlorospiro[benzo[d][1,3]oxazine-4,3'-piperidin]-2(1H)-one (14.9 mg, 0.059 mmol), (Z)-2$^4$-Fluoro-4-oxo-1$^1$-((2-(trimethylsilyl)ethoxy)methyl)-1$^1$H-3-aza-1(4,2)-imidazola-2(1,2)-benzenacyclononaphane-9-carboxylic acid (22 mg, 0.049 mmol) and HATU (28.0 mg, 0.074 mmol) in DCM (0.5 mL) was added DIEA (0.026 mL, 0.147 mmol). The mixture was stirred at rt for 2 h. It was purified by flash column chromatography on silica gel (0-5% MeOH in DCM) to give the diastereomer A of the title compound (first peak) and the other diastereomer B (second peak). MS (ES$^+$) m/z: 682 (M+H) for both isomers.

Step J: (R)-6-Chloro-1'-((R,Z)-2$^4$-fluoro-4-oxo-1$^1$H-3-aza-1(4,2)-imidazola-2(1,2)-benzenacyclononaphane-9-carbonyl)spiro[benzo[d][1,3]oxazine-4,3'-piperidin]-2(1H)-one (EX-2a) and (R)-6-Chloro-1'-((R,Z)-2$^4$-fluoro-4-oxo-1$^1$H-3-aza-1(4,2)-imidazola-2(1,2)-benzenacyclononaphane-9-carbonyl)spiro[benzo[d][1,3]oxazine-4,3'-piperidin]-2(1H)-one (EX-2b)

The two diastereomers isolated from Step I (isomer A: 13 mg, 0.019 mmol, isomer B: 17 mg, 0.025 mmol) was treated separately with TFA (500 μl, 6.49 mmol) at 60° C. for 10 min. It was cooled to rt and concentrated under reduced pressure. The residue was dissolved in 2 mL DCM with 0.2 mL of TEA and purified by flash column chromatography on silica gel (0-6% MeOH in DCM) to give Example 2a from diastereomer A or Example 2b from diastereomer B. MS (ES$^+$) m/z: 552 (M+H) for both isomers.

By using procedures similar to those described above, the following compounds were synthesized and characterized.

| Example | Structure | LCMS [M + 1] | Hu FXIa Ki (nM) |
|---|---|---|---|
| 1a | methyl ((R,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate | 593 | 2.37 |
| 1b | methyl ((S,Z)-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate | 593 | 258 |

-continued

| Example | Structure | LCMS [M + 1] | Hu FXIa Ki (nM) |
|---|---|---|---|
| 2a | (R)-6-chloro-1'-((R,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-piperidin]-2(1H)-one | 552 | 268 |
| 2b | (R)-6-chloro-1'-((S,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-piperidin]-2(1H)-one | 552 | >5000 |
| 3a | methyl ((R,Z)-9-((R)-6-chloro-2-oxo-1,2-dihydrospiro[benzo[d][1,3]oxazine-4,3'-piperidine]-1'-carbonyl)-4-oxo-1¹H-3-aza-1(4,2)-imidazola-2(1,2)-benzenacyclononaphane-2⁴-yl)carbamate | 607 | 2.74 |
| 3b | methyl ((S,Z)-9-((R)-6-chloro-2-oxo-1,2-dihydrospiro[benzo[d][1,3]oxazine-4,3'-piperidine]-1'-carbonyl)-4-oxo-1¹H-3-aza-1(4,2)-imidazola-2(1,2)-benzenacyclononaphane-2⁴-yl)carbamate | 607 | 65 |

-continued

| Example | Structure | LCMS [M + 1] | Hu FXIa Ki (nM) |
|---------|-----------|--------------|-----------------|
| 4 (mixture of two diastereomers) | 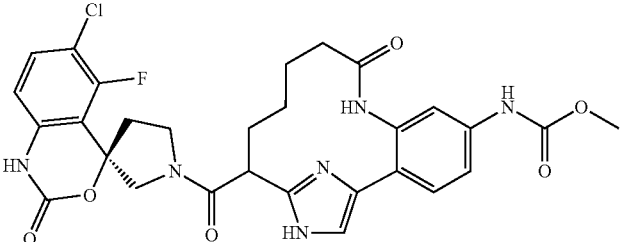 [SMILES: COC(=O)Nc1ccc2c(c1)NC(=O)CCCCC(C(=O)N1CC[C@@]3(C1)OC(=O)Nc1ccc(Cl)c(F)c13)c1nc-2c[nH]1]<br>methyl ((Z)-9-((R)-6-chloro-5-fluoro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate | 611 | 0.86 |
| 5a | 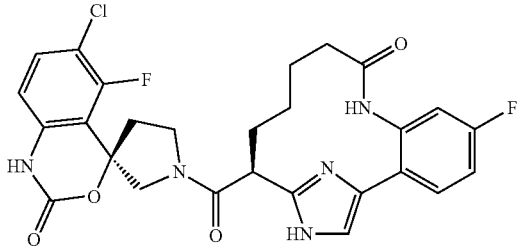 [SMILES: O=C1CCCC[C@H](C(=O)N2CC[C@@]3(C2)OC(=O)Nc2ccc(Cl)c(F)c23)c2nc(c[nH]2)-c2ccc(F)cc2N1]<br>(R)-6-chloro-1'-((S,Z)-2$^4$-fluoro-4-oxo-1$^1$H-3-aza-1(4,2)-imidazola-2(1,2)-benzenacyclononaphane-9-carbonyl)spiro[benzo[d][1,3]oxazine-4,3'-pyrrolidin]-2(1H)-one | 538 | >8750 |
| 5b | 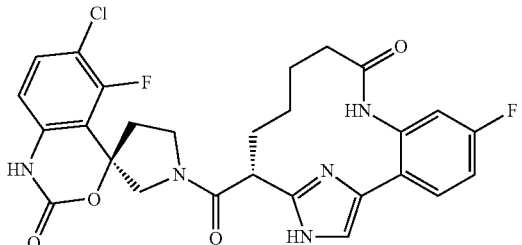<br>(R)-6-chloro-1'-((R,Z)-2$^4$-fluoro-4-oxo-11H-3-aza-1(4,2)-imidazola-2(1,2)-benzenacyclononaphane-9-carbonyl)spiro[benzo[d][1,3]oxazine-4,3'-pyrrolidin]-2(1H)-one | 538 | 180 |

Example 6

Methyl ((Z)-1$^5$-chloro-9-((R)-6-chloro-2-oxo-1,2-dihydrospiro[benzo[d][1,3]oxazine-4,3'-pyrrolidine]-1'-carbonyl)-4-oxo-1$^1$H-3-aza-1(4,2)-imidazola-2(1,2)-benzenacyclononaphane-2$^4$-yl)carbamate (EX-6)

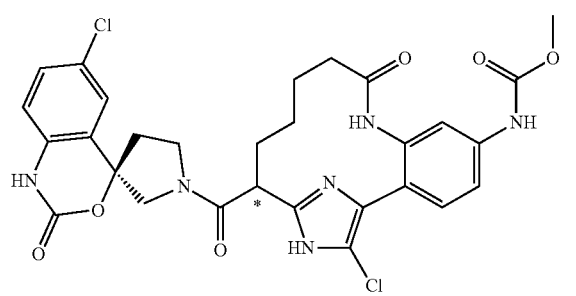

EX-6a and 6b

Synthetic Scheme for Example 6

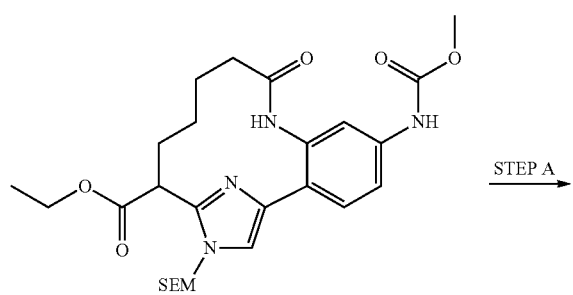

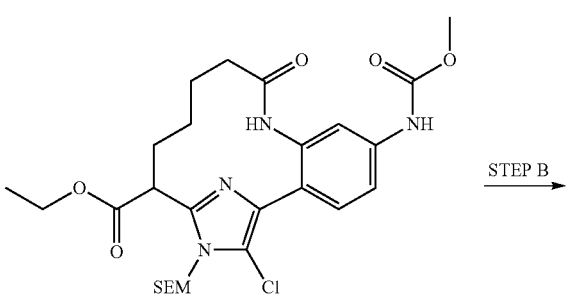

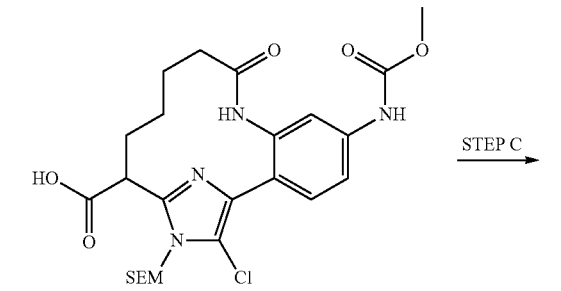

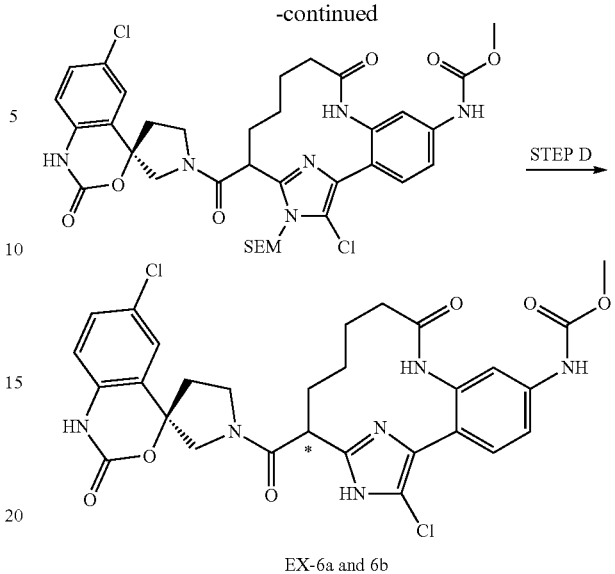

EX-6a and 6b

Step A: Ethyl (Z)-1$^5$-chloro-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylate Ethyl (Z)-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylate (71 mg, 0.134 mmol) was treated with 0.1 M NCS in MeCN/chloroform (1:1) (134 µl, 0.134 mmol) and the mixture was heated at 65° C. for 8 h. It was cooled to rt and purified directly by flash column chromatography on silica gel (0-100% ethyl acetate in hexane) to give the title compound. LC/MS (ES) m/z: 565 (M+1).

Step B: (Z)-1$^5$-Chloro-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylic Acid Ethyl (Z)-1$^5$-chloro-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylate (47 mg, 0.083 mmol) in THF (277 µl), MeOH (277 µl) and water (277 µl) was added aq, LiOH (5 M, 20 µl, 0.100 mmol). The reaction mixture was stirred at RT for 1 h and was acidified with (1 M, 0.1 mL) to pH 5. The solvents were removed. It was diluted with ethyl acetate (2×10 mL), washed with brine, dried over sodium sulfate, filtered and concentrated under reduced pressure to give the title compound, which was used in the next step without further purification. LC/MS (ES) m/z: 537 (M+1).

Step C: Methyl ((Z)-1$^5$-chloro-9-((R)-6-chloro-2-oxo-1,2-dihydrospiro[benzo[d][1,3]oxazine-4,3'-pyrrolidine]-1'-carbonyl)-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate A solution of (R)-6-chlorospiro[benzo[d][1,3]oxazine-4,3'-pyrrolidin]-2(1H)-one (25 mg, 0.105 mmol), (Z)-1$^5$-chloro-2$^4$-((methoxycarbonyl)amino)-4-oxo-1$^1$-((2-(trimethylsilyl)ethoxy)methyl)-1$^1$H-3-aza-1(4,2)-imidazola-2(1,2)-benzenacyclononaphane-9-carboxylic acid (47 mg, 0.088 mmol) and HATU (49.9 mg, 0.131 mmol) in DCM (1 mL)

was added DIEA (0.046 mL, 0.263 mmol). The mixture was stirred at rt for 30 min. It was purified by flash column chromatography on silica gel (0-5% MeOH in DCM) to give the title compound as a solid. LC/MS (ES+) m/z: 757.5 (M+1).

Step D: (R)-6-chloro-1'-((R,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-pyrrolidin]-2(1H)-one (EX-6a) and (R)-6-chloro-1'-((S,Z)-2⁴-fluoro-4-oxo-1¹H-3-aza-1(4,2)-imidazola-2(1,2)-benzenacyclononaphane-9-carbonyl)spiro[benzo[d][1,3]oxazine-4,3'-pyrrolidin]-2(1H)-one (EX-6b)

Methyl ((Z)-1⁵-chloro-9-((R)-6-chloro-2-oxo-1,2-dihydrospiro[benzo[d][1,3]oxazine-4,3'-pyrrolidine]-1'-carbonyl)-4-oxo-1¹-((2-(trimethylsilyl)ethoxy)methyl)-1¹H-3-aza-1(4,2)-imidazola-2(1,2)-benzenacyclononaphane-2⁴-yl)carbamate (50 mg, 0.066 mmol) was treated with TFA (2 mL, 26.0 mmol) at 60° C. for 10 min. It was cooled to rt and concentrated under reduced pressure. It was dissolved in 3 mL of DCM with 0.1 mL of TEA and purified by flash column chromatography on silica gel (0-10% MeOH in DCM) to give a diastereomer mixture. Two diastereomers were separated by SFC (OD-H, 2×25 cm, 40% ethanol (0.1% DEA)/CO₂, 100 bar, 50 mL/min) to give Example 6a (first peak). LC/MS (ES+) m/z: 627 (M+H) and Example 6b (second peak). LC/MS (ES+) m/z: 627 (M+1).

By using procedures similar to those described above, the following compounds were synthesized and characterized.

| Example | Structure | LCMS [M + 1] | Hu FXIa Ki (nM) |
|---|---|---|---|
| 6a | methyl ((R,Z)-1⁵-chloro-9-((R)-6-chloro-2-oxo-1,2-dihydrospiro[benzo[d][1,3]oxazine-4,3'-pyrrolidine]-1'-carbonyl)-4-oxo-1¹H-3-aza-1(4,2)-imidazola-2(1,2)-benzenacyclononaphane-2⁴-yl)carbamate | 627 | 0.37 |
| 6b | methyl ((S,Z)-1⁵-chloro-9-((R)-6-chloro-2-oxo-1,2-dihydrospiro[benzo[d][1,3]oxazine-4,3'-pyrrolidine]-1'-carbonyl)-4-oxo-1¹H-3-aza-1(4,2)-imidazola-2(1,2)-benzenacyclononaphane-2⁴-yl)carbamate | 627 | 16 |
| 7a | methyl ((R,Z)-1⁵-chloro-9-((R)-6-chloro-2-oxo-1,2-dihydrospiro[benzo[d][1,3]oxazine-4,3'-piperidine]-1'-carbonyl)-4-oxo-11H-3-aza-1(4,2)-imidazola-2(1,2)-benzenacyclononaphane-2⁴-yl)carbamate | 641 | 0.42 |

| Example | Structure | LCMS [M + 1] | Hu FXIa Ki (nM) |
|---|---|---|---|
| 7b | methyl ((S,Z)-1⁵-chloro-9-((R)-6-chloro-2-oxo-1,2-dihydrospiro[benzo[d][1,3]oxazine-4,3'-piperidine]-1'-carbonyl)-4-oxo-1¹H-3-aza-1(4,2)-imidazola-2(1,2)-benzenacyclononaphane-2⁴-yl)carbamate | 642 | 1828 |
| 8 (mixture of two diastereomers) | methyl ((Z)-1⁵-chloro-9-((R)-6-chloro-5-fluoro-2-oxo-1,2-dihydrospiro[benzo[d][1,3]oxazine-4,3'-piperidine]-1'-carbonyl)-4-oxo-1¹H-3-aza-1(4,2)-imidazola-2(1,2)-benzenacyclononaphane-2⁴-yl)carbamate | 661 | 0.25 |
| 9 (mixture of two diastereomers) | methyl ((Z)-1⁵-chloro-9-((R)-6-chloro-5-fluoro-2-oxo-1,2-dihydrospiro[benzo[d][1,3]oxazine-4,3'-pyrrolidine]-1'-carbonyl)-4-oxo-1¹H-3-aza-1(4,2)-imidazola-2(1,2)-benzenacyclononaphane-2⁴-yl)carbamate | 645 | 0.34 |

Example 10

Methyl ((5R,Z)-1⁵-chloro-9-((R)-6-chloro-5-fluoro-2-oxo-1,2-dihydrospiro[benzo[d][1,3]oxazine-4,3'-piperidine]-1'-carbonyl)-5-methyl-4-oxo-1¹H-3-aza-1(4,2)-imidazola-2(1,2)-benzenacyclononaphane-2⁴-yl)carbamate (EX-10)

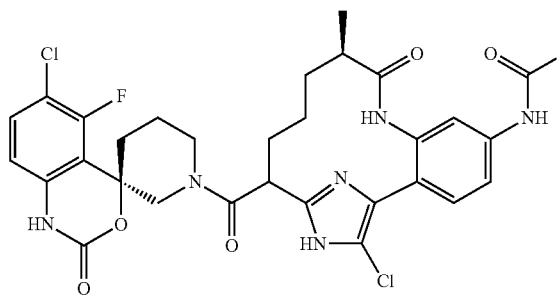

EX-10

Synthetic Scheme for Example 10

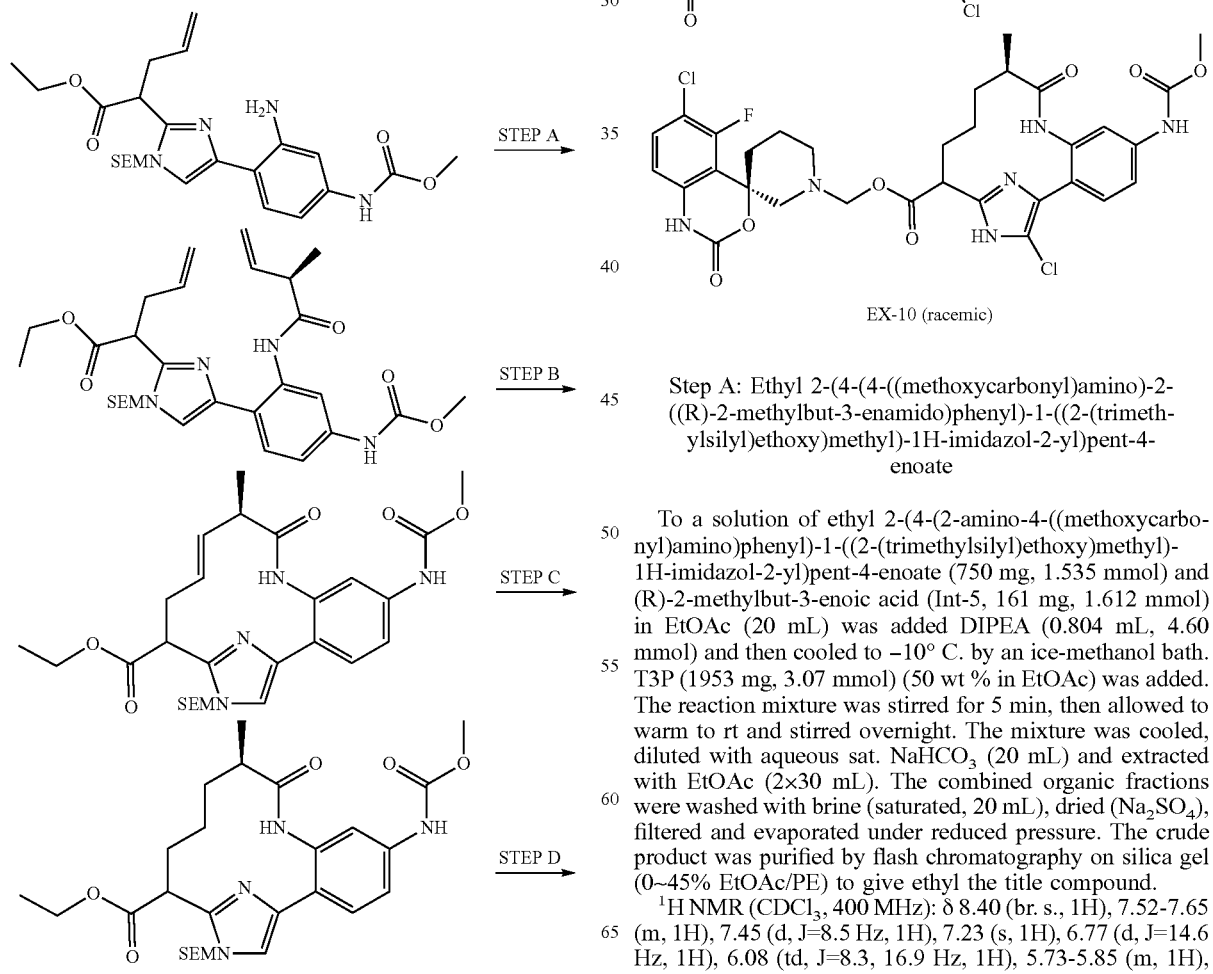

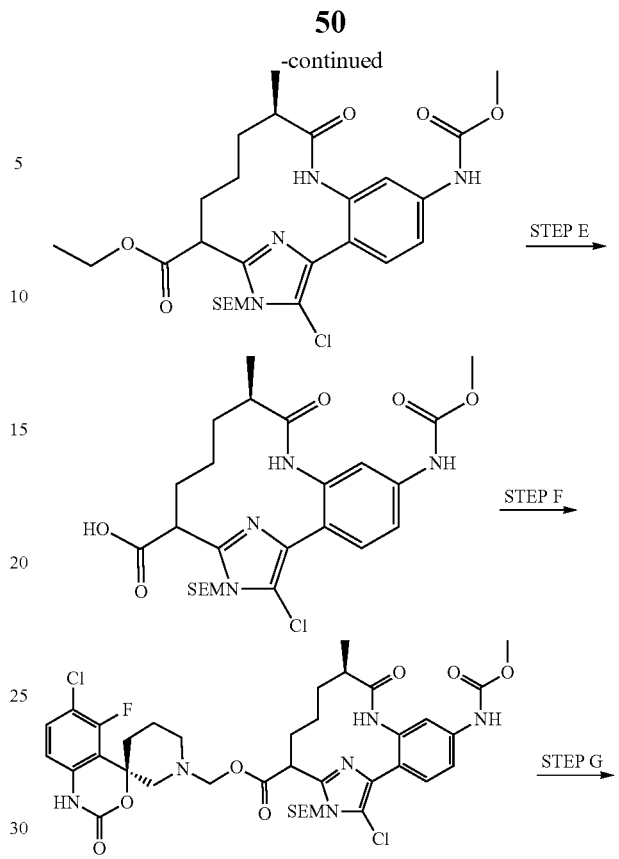

Step A: Ethyl 2-(4-(4-((methoxycarbonyl)amino)-2-((R)-2-methylbut-3-enamido)phenyl)-1-((2-(trimethylsilyl)ethoxy)methyl)-1H-imidazol-2-yl)pent-4-enoate To a solution of ethyl 2-(4-(2-amino-4-((methoxycarbonyl)amino)phenyl)-1-((2-(trimethylsilyl)ethoxy)methyl)-1H-imidazol-2-yl)pent-4-enoate (750 mg, 1.535 mmol) and (R)-2-methylbut-3-enoic acid (Int-5, 161 mg, 1.612 mmol) in EtOAc (20 mL) was added DIPEA (0.804 mL, 4.60 mmol) and then cooled to −10° C. by an ice-methanol bath. T3P (1953 mg, 3.07 mmol) (50 wt % in EtOAc) was added. The reaction mixture was stirred for 5 min, then allowed to warm to rt and stirred overnight. The mixture was cooled, diluted with aqueous sat. NaHCO₃ (20 mL) and extracted with EtOAc (2×30 mL). The combined organic fractions were washed with brine (saturated, 20 mL), dried (Na₂SO₄), filtered and evaporated under reduced pressure. The crude product was purified by flash chromatography on silica gel (0~45% EtOAc/PE) to give ethyl the title compound.

¹H NMR (CDCl₃, 400 MHz): δ 8.40 (br. s., 1H), 7.52-7.65 (m, 1H), 7.45 (d, J=8.5 Hz, 1H), 7.23 (s, 1H), 6.77 (d, J=14.6 Hz, 1H), 6.08 (td, J=8.3, 16.9 Hz, 1H), 5.73-5.85 (m, 1H), 5.46 (dd, J=4.5, 11.0 Hz, 1H), 5.21-5.31 (m, 2H), 5.09-5.20

(m, 3H), 5.05 (d, J=10.0 Hz, 1H), 4.14-4.21 (m, 2H), 3.99-4.06 (m, 1H), 3.77 (s, 3H), 3.51-3.57 (m, 2H), 3.19-3.27 (m, 1H), 2.94-3.04 (m, 1H), 2.85-2.93 (m, 1H), 1.39 (d, J=7.0 Hz, 3H), 1.20-1.25 (m, 3H), 0.94 (dd, J=6.3, 9.0 Hz, 2H), 0.01 (s, 9H).

Step B: Ethyl (1$^2$Z,5R,6E)-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate 2-(4-(4-((methoxycarbonyl)amino)-2-((R)-2-methylbut-3-enamido)phenyl)-1-((2-(trimethylsilyl)ethoxy)methyl)-1H-imidazol-2-yl)pent-4-enoate (200 mg, 0.350 mmol) in 1,2-dichloroethane (32 mL) was degassed by bubbling nitrogen for 15 min. The solution was split into 2 microwave tubes and Zhan Catalyst-1B (51 mg, 0.07 mmol) was added to each tube. They were sealed and heated at 120° C. under nitrogen for 1 h under microwave. The reaction mixture was cooled, pooled and concentrated under reduced pressure. The residue was diluted with EtOAc (50 mL) and washed with aqueous sat. NaHCO$_3$ (30 mL), brine (30 mL). The organic layer was separated, dried (Na$_2$SO$_4$), filtered and concentrated. The crude product was purified by flash chromatography on silica gel (0~35% EtOAc/PE) to give the title compound. LC/MS (ESI) m/z 543.3 (M+1).

Step C: Ethyl (5R,Z)-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphane-9-carboxylate A mixture of ethyl (1$^2$Z,5R,6E)-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphan-6-ene-9-carboxylate (105 mg, 0.193 mmol) and Pd—C(61.8 mg, 0.058 mmol) in MeOH (30 mL) was stirred under 15 psi of H$_2$ at 28° C. for 4 h. The mixture was filtered and the solvent was evaporated. The crude product was purified by flash chromatography on silica gel (0~50% EtOAc/PE) to give the title compound. LC/MS (ESI) m/z 545.1 (M+1).

$^1$H NMR: (CD$_3$OD, 400 MHz): δ 7.68-7.74 (m, 1H), 7.44-7.55 (m, 1H), 7.36-7.43 (m, 1H), 7.31 (s, 1H), 5.27-5.48 (m, 2H), 3.98-4.31 (m, 3H), 3.75 (s, 3H), 3.49-3.61 (m, 2H), 2.78 (t, J=6.8 Hz, 1H), 2.43-2.54 (m, 1H), 2.24-2.37 (m, 1H), 1.99-2.11 (m, 1H), 1.86 (d, J=6.5 Hz, 1H), 1.60-1.76 (m, 1H), 1.42-1.53 (m, 1H), 1.13-1.39 (m, 8H), 0.92 (dt, J=4.8, 8.0 Hz, 2H), 0.06-−0.01 (m, 9H).

Step D: Ethyl (5R,Z)-15-chloro-24-((methoxycarbonyl)amino)-5-methyl-4-oxo-11-((2-(trimethylsilyl)ethoxy)methyl)-11H-3-aza-1(4,2)-imidazola-2(1,2)-benzenacyclononaphane-9-carboxylate To a solution of ethyl (5R,Z)-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphane-9-carboxylate (96 mg, 0.176 mmol) in DCM (5 mL) was added 1,3-dichloro-5,5-dimethylimidazolidine-2,4-dione (36.5 mg, 0.185 mmol) at 0° C. and the reaction mixture was stirred at 0° C. for 20 min. The mixture was filtered and the solvent was evaporated. The crude product was purified by flash chromatography on silica gel (0-30% EtOAc/PE) to give the title compound. LC/MS (ESI) m/z 579.2 (M+1).

$^1$H NMR: (CD$_3$OD, 400 MHz): δ 7.79-7.84 (m, 2H), 7.71-7.78 (m, 2H), 7.45 (s, 1H), 7.20-7.32 (m, 5H), 4.12-4.30 (m, 3H), 3.80 (s, 4H), 3.47 (dd, J=7.7, 13.7 Hz, 1H), 3.21-3.30 (m, 1H), 1.21 (t, J=7.2 Hz, 3H).

Step E: (5R,Z)-1$^5$-Chloro-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphane-9-carboxylic Acid To a solution of ethyl (5R,Z)-15-chloro-24-((methoxycarbonyl)amino)-5-methyl-4-oxo-11-((2-(trimethylsilyl)ethoxy)methyl)-11H-3-aza-1(4,2)-imidazola-2(1,2)-benzenacyclononaphane-9-carboxylate (82 mg, 0.142 mmol) in THF (2 mL), MeOH (2 mL) and water (2 mL) was added 5 M aq. LiOH.H$_2$O (0.113 mL, 0.566 mmol) and the reaction mixture was stirred at RT for 2 hrs. The resulting mixture was acidified by HCl (1 N) to pH 6, and extracted with EtOAc (20 mL×2). The combined organic layers were washed with water (10 mL), brine (10 mL), dried over Na$_2$SO$_4$, filtered and concentrated to give the title compound, which was used in the next step without further purification. LC/MS (ESI) m/z 551.0 (M+1).

Step F: Methyl ((5R,Z)-1$^5$-chloro-9-((R)-6-chloro-5-fluoro-2-oxo-1,2-dihydrospiro[benzo[d][1,3]oxazine-4,3'-piperidine]-1'-carbonyl)-5-methyl-4-oxo-1'-((2-(trimethylsilyl)ethoxy)methyl)-1$^1$H-3-aza-1(4,2)-imidazola-2(1,2)-benzenacyclononaphane-2$^4$-yl)carbamate To a stirred solution of (5R,Z)-1$^5$-chloro-2$^4$-((methoxycarbonyl)amino)-5-methyl-4-oxo-1$^1$-((2-(trimethylsilyl)ethoxy)methyl)-1$^1$H-3-aza-1(4,2)-imidazola-2(1,2)-benzenacyclononaphane-9-carboxylic acid (80 mg, 0.134 mmol) in DCM (5 mL) was added HATU (61.4 mg, 0.161 mmol) at 25° C. The mixture was stirred for 10 min, then a solution of (R)-6-chloro-5-fluorospiro[benzo[d][1,3]oxazine-4,3'-piperidin]-2(1H)-onehydrochloride (41.3 mg, 0.134 mmol) and DIPEA (0.094 mL, 0.538 mmol) in DCM (5.00 mL) was added. The reaction mixture was stirred at RT for 4 hrs. The mixture was diluted with DCM (50 mL), washed with water (30 mL), brine (30 mL), dried (Na$_2$SO$_4$), filtered and concentrated. The crude product was purified by prep-TLC (SiO$_2$, DCM: MeOH=10:1) to give the title compound. LC/MS (ESI) m/z 803.1 (M+1).

Step G: Methyl ((5R,Z)-1$^5$-chloro-9-((R)-6-chloro-5-fluoro-2-oxo-1,2-dihydrospiro[benzo[d][1,3]oxazine-4,3'-piperidine]-1'-carbonyl)-5-methyl-4-oxo-1$^1$H-3-aza-1(4,2)-imidazola-2(1,2)-benzenacyclononaphane-2$^4$-yl)carbamate (EX-10)

To a stirred solution of methyl ((5R,Z)-1$^5$-chloro-9-((R)-6-chloro-5-fluoro-2-oxo-1,2-dihydrospiro[benzo[d][1,3]oxazine-4,3'-piperidine]-1'-carbonyl)-5-methyl-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate (62 mg, 0.077 mmol) in DCM (1.5 mL) was added TFA (1.5 mL) at 25° C. The reaction mixture was stirred at 25° C. for 4 hrs. LCMS showed the starting material was consumed completely. The reaction mixture was concentrated and the residue was purified by prep-HPLC to give the title compound. MS (ESI) m/z 673.0 (M+1).

$^1$H NMR: (CD$_3$OD, 400 MHz): δ 7.46-7.59 (m, 2H), 7.33-7.45 (m, 2H), 6.66-6.79 (m, 1H), 4.63 (d, J=12.1 Hz, 1H), 4.50 (d, J=14.5 Hz, 1H), 4.34-4.44 (m, 1H), 4.08-4.25 (m, 1H), 3.89 (d, J=14.5 Hz, 1H), 3.73 (s, 3H), 3.19 (q, J=7.0 Hz, 1H), 3.10 (d, J=13.7 Hz, 1H), 2.77 (t, J=11.9 Hz, 1H), 2.46-2.65 (m, 2H), 2.26 (d, J=5.9 Hz, 1H), 2.17 (d, J=13.3 Hz, 1H), 1.88-2.11 (m, 3H), 1.49-1.58 (m, 3H), 1.29 (t, J=7.2 Hz, 3H), 1.13 (d, J=6.7 Hz, 3H), 0.84 (br. s., 1H).

By using procedures similar to those described above, the following compounds were synthesized and characterized.

| Example | Structure | LCMS [M + 1] | Hu FXIa Ki (nM) |
|---|---|---|---|
| 10 (mixture of two diastereomers) | methyl ((5R,Z)-1$^5$-chloro-9-((R)-6-chloro-5-fluoro-2-oxo-1,2-dihydrospiro[benzo[d][1,3]oxazine-4,3'-piperidine]-1'-carbonyl)-5-methyl-4-oxo-1$^1$H-3-aza-1(4,2)-imidazola-2(1,2)-benzenacyclononaphane-2$^4$-yl)carbamate | 673 | 0.67 |
| 11 (mixture of two diastereomers) | methyl ((5R,Z)-1$^5$-chloro-9-((R)-6-chloro-5-fluoro-2-oxo-1,2-dihydrospiro[benzo[d][1,3]oxazine-4,3'-pyrrolidine'-1'-carbonyl)-5-methyl-4-oxo-1$^1$H-3-aza-1(4,2)-imidazola-2(1,2)-benzenacyclononaphane-2$^4$-yl)carbamate | 659 | 0.74 |

Example 12

Methyl ((Z)-9-((R)-6-chloro-5-fluoro-2-oxo-1,2-dihydrospiro[benzo[d][1,3]oxazine-4,3'-piperidine]-1'-carbonyl)-1$^5$-methyl-4-oxo-1$^1$H-3-aza-1(4,2)-imidazola-2(1,2)-benzenacyclononaphane-2$^4$-yl) carbamate (EX-12)

EX-12a and 12B

Synthetic Scheme for Example 12

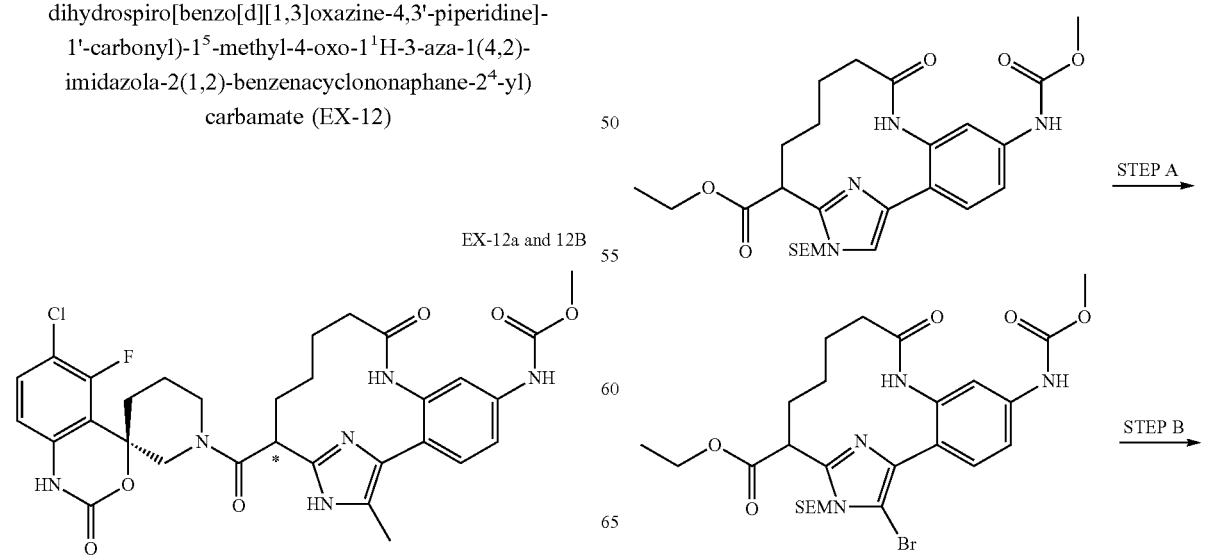

STEP A

STEP B

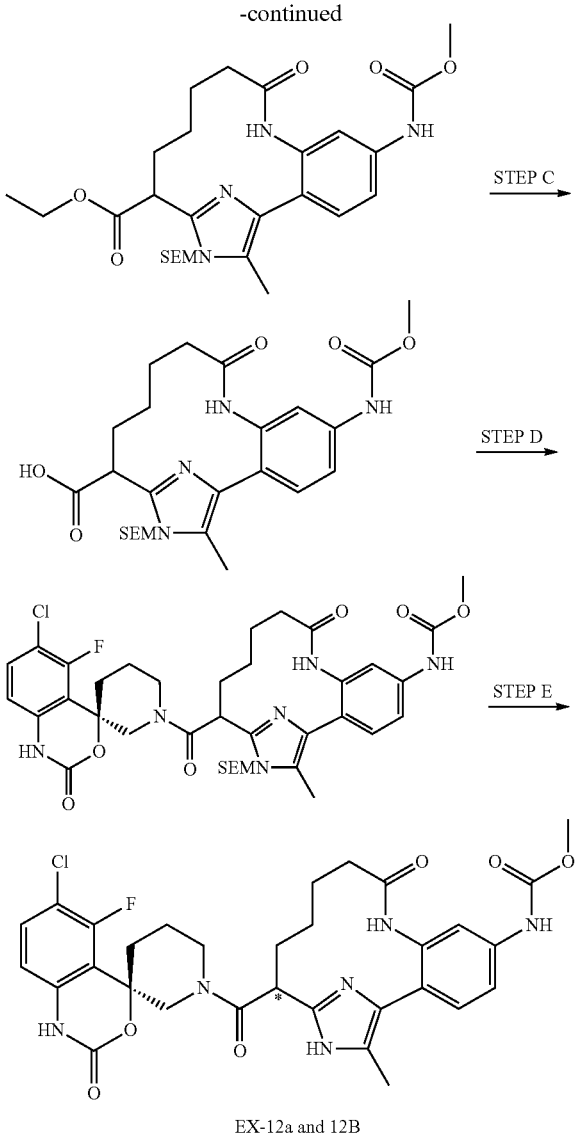

EX-12a and 12B

Step A: Ethyl (Z)-1⁵-bromo-2⁴-((methoxycarbonyl)amino)-4-oxo-1¹-((2-(trimethylsilyl)ethoxy)methyl)-1¹H-3-aza-1(4,2)-imidazola-2(1,2)-benzenacyclononaphane-9-carboxylate To a cooled solution of ethyl (Z)-2⁴-((methoxycarbonyl)amino)-4-oxo-1¹-((2-(trimethylsilyl)ethoxy)methyl)-1¹H-3-aza-1(4,2)-imidazola-2(1,2)-benzenacyclononaphane-9-carboxylate (350 mg, 0.660 mmol) in CHCl₃ (10 mL) was added NBS (129 mg, 0.725 mmol) and the mixture was stirred at 0° C. under N₂ protection for 30 min. Solvent was removed and the residue was purified by prep-HPLC (C18, 5 um, 42-72% acetonitrile in water (containing 0.1% TFA, v/v) to give the title compound. LC/MS (ESI) m/z 611.2 (M+H).

Step B: Ethyl (Z)-2⁴-((methoxycarbonyl)amino)-1⁵-methyl-4-oxo-1¹-((2-(trimethylsilyl)ethoxy)methyl)-1¹H-3-aza-1(4,2)-imidazola-2(1,2)-benzenacyclononaphane-9-carboxylate To a solution of ethyl (Z)-1⁵-bromo-2⁴-((methoxycarbonyl)amino)-4-oxo-1¹-((2-(trimethylsilyl)ethoxy)methyl)-1¹H-3-aza-1(4,2)-imidazola-2 (1,2)-benzenacyclononaphane-9-carboxylate (130 mg, 0.213 mmol) in dioxane (2 mL) was added cesium carbonate (208 mg, 0.640 mmol) 1,1'-bis(diphenylphosphino)ferrocene-palladium dichloride dichloromethane complex (17.42 mg, 0.021 mmol) and trimethylboroxine (134 mg, 1.066 mmol). The resulting mixture under N₂ was stirred at 90° C. for 16 h under microwave irradiation. After cooling to RT, the mixture was filtered through a thin pad of Celite and the filtrate was concentrated. The residue was purified by prep-TLC (SiO₂, PE: EtOAc=2:1) to give the title compound. LC/MS (ESI) m/z 545.2 (M+1).

Step C: (Z)-2⁴-((Methoxycarbonyl)amino)-1⁵-methyl-4-oxo-1¹-((2-(trimethylsilyl)ethoxy)methyl)-1¹H-3-aza-1(4,2)-imidazola-2(1,2)-benzenacyclononaphane-9-carboxylic Acid To a solution of ethyl (Z)-2⁴-((methoxycarbonyl)amino)-1⁵-methyl-4-oxo-1¹-((2-(trimethylsilyl)ethoxy)methyl)-1¹H-3-aza-1(4,2)-imidazola-2(1,2)-benzenacyclononaphane-9-carboxylate (45 mg, 0.083 mmol) in MeOH (0.18 mL), THF (0.18 mL) and water (0.18 mL) was added lithium hydroxide (2.156 mg, 0.090 mmol) and the reaction mixture was stirred at 20° C. for 2 h. The mixture was diluted with water (3 mL) and then adjusted to pH 4-5 with 1N HCl and extracted with EtOAc (5 mL×3). The combined organic layers were dried over Na₂SO₄ and concentrated to give the title compound, which was used in next step without further purification. LC/MS (ESI) m/z 517.3 (M+H).

Step D: Methyl ((Z)-9-((R)-6-chloro-5-fluoro-2-oxo-1,2-dihydrospiro[benzo[d][1,3]oxazine-4,3'-piperidine]-1'-carbonyl)-1⁵-methyl-4-oxo-1¹-((2-(trimethylsilyl)ethoxy)methyl)-1¹H-3-aza-1(4,2)-imidazola-2(1,2)-benzenacyclononaphane-24-yl)carbamate To a solution of (Z)-2⁴-((methoxycarbonyl)amino)-1⁵-methyl-4-oxo-1¹-((2-(trimethylsilyl)ethoxy)methyl)-1¹H-3-aza-1(4,2)-imidazola-2(1,2)-benzenacyclononaphane-9-carboxylic acid (35 mg, 0.068 mmol) in DCM (1.5 mL) was added (R)-6-chloro-5-fluorospiro[benzo[d][1,3]oxazine-4,3'-piperidin]-2(1H)-one (24.57 mg, 0.091 mmol), DIPEA (0.035 mL, 0.203 mmol) and HATU (38.6 mg, 0.102 mmol). The mixture was stirred at 25° C. for 2 hrs. LCMS showed the reactants were consumed. The mixture was diluted with DCM (5 mL) and washed with water (5 mL×3). The organic layer was separated, dried over Na₂SO₄, filtered and concentrated to give the title compound, which was used in next step without further purification. MS (ESI) m/z 769.3 (M+1).

Step E: Methyl ((Z)-9-((R)-6-chloro-5-fluoro-2-oxo-1,2-dihydrospiro[benzo[d][1,3]oxazine-4,3'-piperidine]-1'-carbonyl)-1⁵-methyl-4-oxo-1¹H-3-aza-1(4,2)-imidazola-2(1,2)-benzenacyclononaphane-2⁴-yl)carbamate (EX-12)

A mixture of methyl ((Z)-9-((R)-6-chloro-5-fluoro-2-oxo-1,2-dihydrospiro[benzo[d][1,3]oxazine-4,3'-piperidine]-1'-carbonyl)-1⁵-methyl-4-oxo-1¹-((2-(trimethylsilyl)ethoxy)methyl)-1¹H-3-aza-1(4,2)-imidazola-2(1,2)-benzenacyclononaphane-24-yl)carbamate (20 mg, 0.026 mmol) in TFA (0.5 mL) was stirred at 60° C. for 10 min. The reaction mixture was cooled and concentrated. The residue was purified by prep-HPLC (, Gradient: 16-46% acetonitrile in water (containing 0.1% TFA, v/v)) to give the title compound. LC/MS (ESI) m/z 639.3 (M+1).

¹H NMR: (CD₃OD, 400 MHz): δ 7.32-7.62 (m, 4H), 6.60-6.79 (m, 1H), 4.56-4.76 (m, 1H), 4.30-4.53 (m, 1H), 3.94-4.26 (m, 1H), 3.74 (d, J=3.5 Hz, 3H), 3.33 (s, 2H), 3.09-3.26 (m, 1H), 2.82-2.99 (m, 1H), 2.38-2.69 (m, 2H), 2.30-2.38 (m, 3H), 2.14-2.47 (m, 2H), 1.88-2.12 (m, 3H), 1.51-1.76 (m, 3H), 1.28 (brs, 3H).

The two diastereomers were resolved by SFC (Column: OD), Mobile phase:base-50% EtOH, Flow rate:70 mL/min Wavelength: 220 nm) to give EX-12a (faster-eluting isomer) EX-12b (slow-eluting isomer B).

EX-12a $^1$H NMR: (CD$_3$OD, 400 MHz): δ 7.33-7.58 (m, 4H), 6.61-6.79 (m, 1H), 4.55-4.72 (m, 1H), 4.31-4.53 (m, 1H), 4.01-4.26 (m, 1H), 3.74 (d, J=2.7 Hz, 3H), 3.33-3.48 (m, 1H), 3.14 (d, J=14.1 Hz, 1H), 2.81-3.00 (m, 2H), 2.37-2.69 (m, 2H), 2.30-2.35 (m, 3H), 2.13-2.25 (m, 2H), 1.80-2.08 (m, 3H), 1.52-1.68 (m, 2H), 1.36 (s, 1H), 1.27 (br. s., 3H). LC/MS (ESI) m/z 639.2 (M+H).

EX-12b $^1$H NMR: (CD$_3$OD, 400 MHz): δ 7.23-7.80 (m, 4H), 6.70-6.81 (m, 1H), 4.93 (d, J=13.7 Hz, 2H), 4.43-4.77 (m, 1H), 4.23 (d, J=13.7 Hz, 1H), 3.68-3.75 (m, 3H), 3.06 (d, J=13.7 Hz, 1H), 2.78 (t, J=12.5 Hz, 2H), 2.29 (s, 3H), 2.11-2.25 (m, 4H), 1.88-2.10 (m, 2H), 1.63-1.81 (m, 1H), 1.11-1.53 (m, 5H). LC/MS (ESI) m/z 639.2 (M+H).

By using procedures similar to those described above, the following compounds were synthesized and characterized.

| Example | Structure | LCMS [M + 1] | Hu FXIa Ki (nM) |
|---|---|---|---|
| 12 (mixture of two diastereomers) | methyl ((Z)-9-((R)-6-chloro-5-fluoro-2-oxo-1,2-dihydrospiro[benzo[d][1,3]oxazine-4,3'-piperidine]-1'-carbonyl)-1$^5$-methyl-4-oxo-1$^1$H-3-aza-1(4,2)-imidazola-2(1,2)-benzenacyclononaphane-2$^4$-yl)carbamate | 639 | 2.70 |
| 12a | methyl ((S,Z)-9-((R)-6-chloro-5-fluoro-2-oxo-1,2-dihydrospiro[benzo[d][1,3]oxazine-4,3'-piperidine]-1'-carbonyl)-1$^5$-methyl-4-oxo-1$^1$H-3-aza-1(4,2)-imidazola-2(1,2)-benzenacyclononaphan-2$^4$-yl)carbamate | 639 | 471 |
| 12b | methyl ((R,Z)-9-((R)-6-chloro-5-fluoro-2-oxo-1,2-dihydrospiro[benzo[d][1,3]oxazine-4,3'-piperidine]-1'-carbonyl)-1$^5$-methyl-4-oxo-1$^1$H-3-aza-1(4,2)-imidazola-2(1,2)-benzenacyclononaphane-2$^4$-yl)carbamate | 639 | 0.93 |

| Example | Structure | LCMS [M + 1] | Hu FXIa Ki (nM) |
|---|---|---|---|
| 13a | 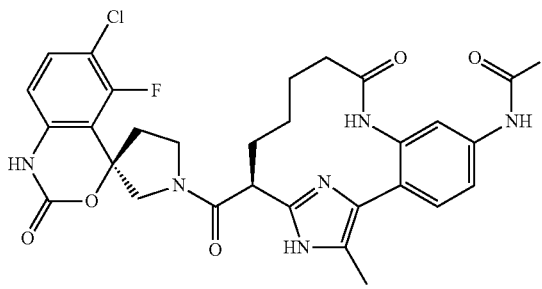<br>methyl ((S,Z)-9-((R)-6-chloro-5-fluoro-2-oxo-1,2-dihydrospiro[benzo[d][1,3]oxazine-4,3'-pyrrolidine]-1'-carbonyl)-1⁵-methyl-4-oxo-1¹H-3-aza-1(4,2)-imidazola-2(1,2)-benzenacyclononaphane-2⁴-yl)carbamate | 625 | 195 |
| 13b | 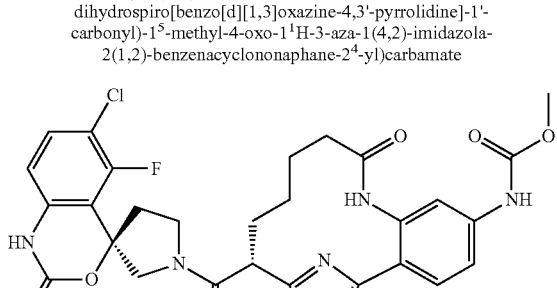<br>methyl ((R,Z)-9-((R)-6-chloro-5-fluoro-2-oxo-1,2-dihydrospiro[benzo[d][1,3]oxazine-4,3'-pyrrolidine]-1'-carbonyl)-1⁵-methyl-4-oxo-1¹H-3-aza-1(4,2)-imidazola-2(1,2)-benzenacyclononaphane-2⁴-yl)carbamate | 625 | 0.6 |

Example 14

Methyl ((5R,9R)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2⁴-yl)carbamate (EX-14a) and Methyl ((5R,9S)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2⁴-ylcarbamate (EX-14b)

Synthetic Scheme for Example 14

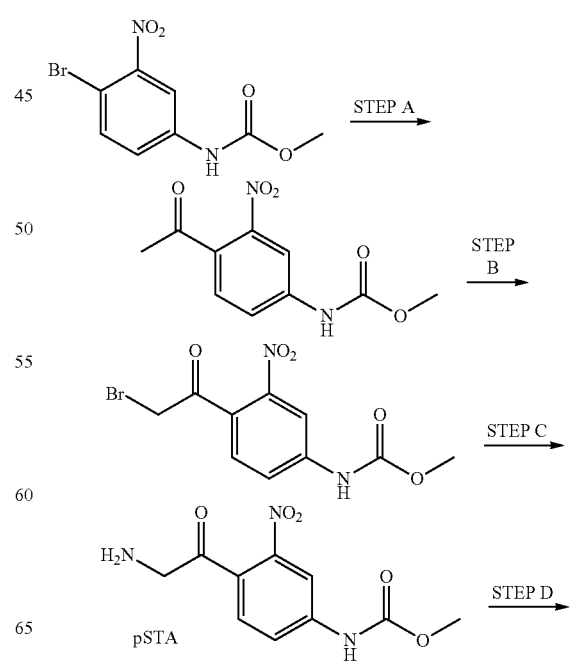

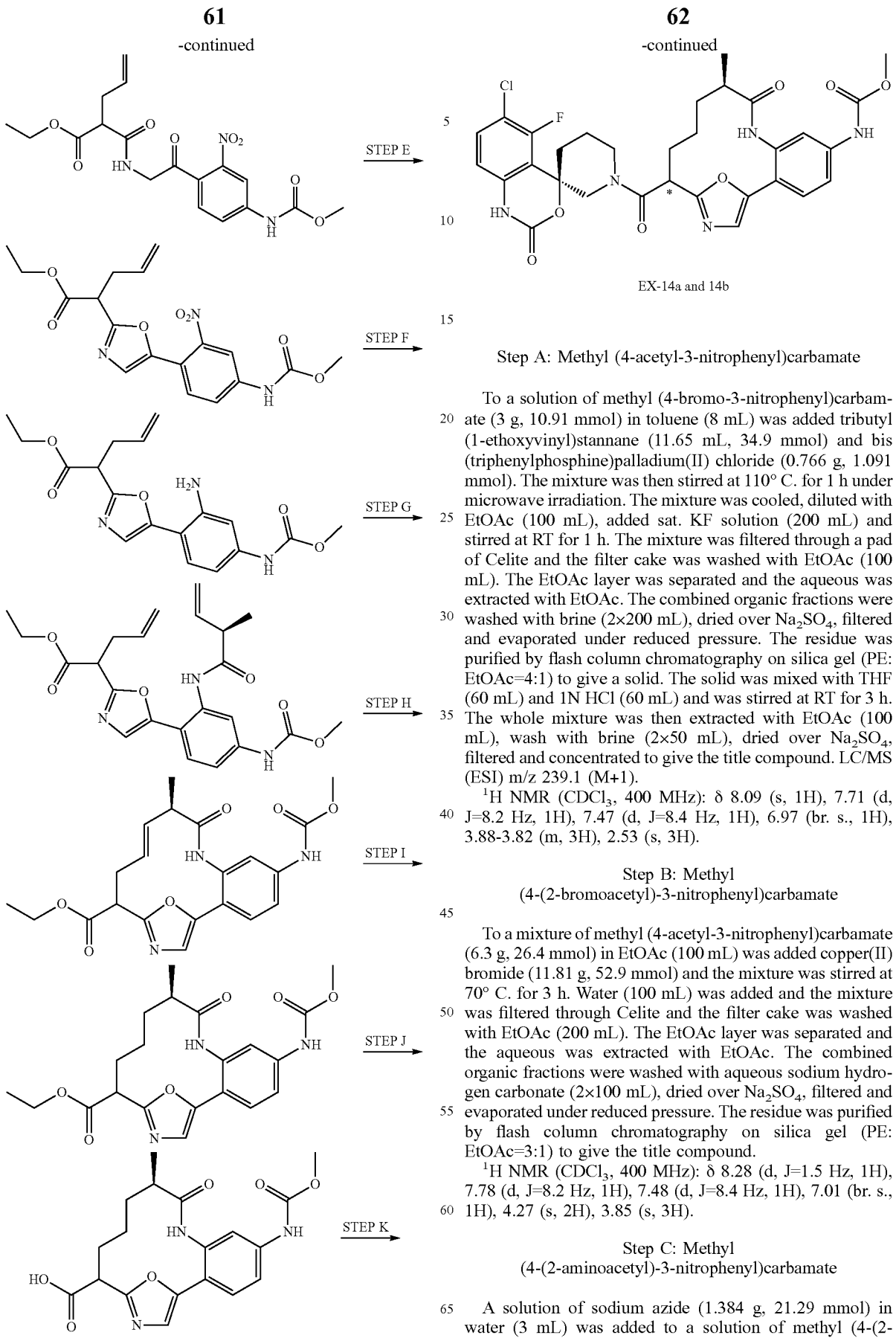

EX-14a and 14b

Step A: Methyl (4-acetyl-3-nitrophenyl)carbamate

To a solution of methyl (4-bromo-3-nitrophenyl)carbamate (3 g, 10.91 mmol) in toluene (8 mL) was added tributyl (1-ethoxyvinyl)stannane (11.65 mL, 34.9 mmol) and bis(triphenylphosphine)palladium(II) chloride (0.766 g, 1.091 mmol). The mixture was then stirred at 110° C. for 1 h under microwave irradiation. The mixture was cooled, diluted with EtOAc (100 mL), added sat. KF solution (200 mL) and stirred at RT for 1 h. The mixture was filtered through a pad of Celite and the filter cake was washed with EtOAc (100 mL). The EtOAc layer was separated and the aqueous was extracted with EtOAc. The combined organic fractions were washed with brine (2×200 mL), dried over $Na_2SO_4$, filtered and evaporated under reduced pressure. The residue was purified by flash column chromatography on silica gel (PE:EtOAc=4:1) to give a solid. The solid was mixed with THF (60 mL) and 1N HCl (60 mL) and was stirred at RT for 3 h. The whole mixture was then extracted with EtOAc (100 mL), wash with brine (2×50 mL), dried over $Na_2SO_4$, filtered and concentrated to give the title compound. LC/MS (ESI) m/z 239.1 (M+1).

$^1$H NMR (CDCl$_3$, 400 MHz): δ 8.09 (s, 1H), 7.71 (d, J=8.2 Hz, 1H), 7.47 (d, J=8.4 Hz, 1H), 6.97 (br. s., 1H), 3.88-3.82 (m, 3H), 2.53 (s, 3H).

Step B: Methyl (4-(2-bromoacetyl)-3-nitrophenyl)carbamate

To a mixture of methyl (4-acetyl-3-nitrophenyl)carbamate (6.3 g, 26.4 mmol) in EtOAc (100 mL) was added copper(II) bromide (11.81 g, 52.9 mmol) and the mixture was stirred at 70° C. for 3 h. Water (100 mL) was added and the mixture was filtered through Celite and the filter cake was washed with EtOAc (200 mL). The EtOAc layer was separated and the aqueous was extracted with EtOAc. The combined organic fractions were washed with aqueous sodium hydrogen carbonate (2×100 mL), dried over $Na_2SO_4$, filtered and evaporated under reduced pressure. The residue was purified by flash column chromatography on silica gel (PE:EtOAc=3:1) to give the title compound.

$^1$H NMR (CDCl$_3$, 400 MHz): δ 8.28 (d, J=1.5 Hz, 1H), 7.78 (d, J=8.2 Hz, 1H), 7.48 (d, J=8.4 Hz, 1H), 7.01 (br. s., 1H), 4.27 (s, 2H), 3.85 (s, 3H).

Step C: Methyl (4-(2-aminoacetyl)-3-nitrophenyl)carbamate

A solution of sodium azide (1.384 g, 21.29 mmol) in water (3 mL) was added to a solution of methyl (4-(2-bromoacetyl)-3-nitrophenyl)carbamate (4.5 g, 14.19 mmol)

in THF (15 mL) at 0° C. The reaction mixture was stirred at 20° C. for 16 h. TLC (PE: EtOAc=1:1) showed starting material was consumed. The reaction mixture was then added dropwise to a stirred mixture of 4-methylbenzenesulfonic acid (3.91 g, 22.71 mmol), triphenylphosphine (5.96 g, 22.71 mmol) in THF (10 mL) and the mixture was stirred at 20° C. for 12 h. The suspension was concentrated. The residue was purified by flash column chromatography on silica gel (MeOH: DCM=1:10) to give the title compound. LC/MS (ESI) m/z 254.1 (M+1). $^1$H NMR (CH$_3$OD, 400 MHz): δ 8.23 (d, J=1.5 Hz, 1H), 7.80 (d, J=8.6 Hz, 1H), 7.70 (br. s., 1H), 7.21 (d, J=7.9 Hz, 3H), 4.41 (s, 2H), 3.77 (s, 3H).

Step D: Ethyl 2-((2-(4-((methoxycarbonyl)amino)-2-nitrophenyl)-2-oxoethyl)carbamoyl)pent-4-enoate To a stirred mixture of 2-(ethoxycarbonyl)pent-4-enoic acid (1.821 g, 10.58 mmol), HATU (8.04 g, 21.16 mmol), DIPEA (3.69 mL, 21.16 mmol) in DMF (50 mL) was added methyl (4-(2-aminoacetyl)-3-nitrophenyl)carbamate (3 g, 7.05 mmol) and the mixture was stirred at 25° C. for 2 h. Water (50 mL) was added and the mixture was extracted with EtOAc (2×100 mL). The combined organic fractions were washed with brine (4×100 mL), dried over Na$_2$SO$_4$, filtered and evaporated under reduced pressure. The residue was purified by flash column chromatography on silica gel (PE: EtOAc=3:1) to give the title compound. LC/MS (ESI) m/z 408.1 (M+1).
$^1$H NMR (CD$_3$OD, 400 MHz): δ 8.32 (s, 1H), 7.74 (d, J=8.4 Hz, 1H), 7.57 (d, J=8.4 Hz, 1H), 5.63-5.76 (m, 1H), 4.95-5.12 (m, 2H), 4.32-4.46 (m, 2H), 3.79 (s, 3H), 3.40 (t, J=7.5 Hz, 1H), 2.38-2.64 (m, 2H), 1.24 (s, 3H).

Step E: Ethyl 2-(5-(4-((methoxycarbonyl)amino)-2-nitrophenyl)oxazol-2-yl)pent-4-enoate A mixture of ethyl 2-((2-(4-((methoxycarbonyl)amino)-2-nitrophenyl)-2-oxoethyl)carbamoyl)pent-4-enoate (50 mg, 0.123 mmol) in phosphoryl trichloride (1.8 mL, 0.123 mmol) was stirred at 110° C. for 4 h. The reaction mixture was concentrated and the residue was used for next step without further purification. LC/MS (ESI) m/z 390.1 (M+H).

Step F: Ethyl 2-(5-(2-amino-4-((methoxycarbonyl)amino)phenyl)oxazol-2-yl)pent-4-enoate To a mixture of ethyl 2-(5-(4-((methoxycarbonyl)amino)-2-nitrophenyl)oxazol-2-yl)pent-4-enoate (680 mg, 1.746 mmol) in EtOH (25 mL)/water (5 mL) was added iron powder (488 mg, 8.73 mmol), ammonia hydrochloride (934 mg, 17.46 mmol) and the mixture was stirred at 80° C. for 2 h. The mixture was cooled and filtered through a pad of Celite. The filter cake was washed with EtOH (30 mL). The combined filtrates were concentrated. The residue was diluted with water (20 mL) and extracted with EtOAc (3×20 mL). The combined organic fractions were washed with brine (20 mL), dried over Na$_2$SO$_4$, filtered and evaporated under reduced pressure to give the title compound, which was used in the next step without further purification. LC/MS (ESI) m/z 359.9 (M+1).

Step G: Ethyl 2-(5-(4-((methoxycarbonyl)amino)-2-((R)-2-methylbut-3-enamido)phenyl)oxazol-2-yl)pent-4-enoate To a solution of (R)-2-methylbut-3-enoic acid (190 mg, 1.898 mmol) and ethyl 2-(5-(2-amino-4-((methoxycarbonyl)amino)phenyl)oxazol-2-yl)pent-4-enoate (620 mg, 1.725 mmol) in DMF (10 mL) was added 2,4,6-tripropyl-1,3,5,2,4,6-trioxatriphosphinane 2,4,6-trioxide (1317 mg, 2.070 mmol) (50% in EtOAc) at 0° C. After 30 min, DIPEA (780 mg, 6.04 mmol) was added and the mixture was stirred at 20° C. for 16 hrs. The reaction mixture was diluted with water and extracted with EtOAc (3×20 mL). The combined organic phases were washed with water (20 mL), brine (30 mL), dried over Na$_2$SO$_4$, filtered and concentrated. The residue was purified by flash column chromatography on silica gel (PE:EtOAc=5:1) to give the title compound. LC/MS (ESI) m/z 442.1 (M+1)

Step H: Ethyl (5R,E)-2$^4$-((methoxycarbonyl)amino)-5-methyl-4-oxo-3-aza-1(5,2)-oxazola-2(1,2)-benzenacyclononaphan-6-ene-9-carboxylate A mixture of pTSA (118 mg, 0.623 mmol), ethyl2-(5-(4-((methoxycarbonyl)amino)-2-((R)-2-methylbut-3-enamido)phenyl)oxazol-2-yl)pent-4-enoate (250 mg, 0.566 mmol) in DCM (20 mL) was stirred at 40° C. for 1 h. Then Grubbs Catalyst $2^{nd}$ Generation (144 mg, 0.170 mmol) in DCM (3 mL) was added to the above mixture and the mixture was stirred at 40° C. for 18 hrs. The mixture was diluted with aqueous sodium bicarbonate (10 mL) and extracted with DCM (2×50 mL). The combined organic fractions were washed with brine (2×50 mL), dried over Na$_2$SO$_4$, filtered and evaporated under reduced pressure. The residue was purified by prep-TLC on silica gel, eluting with PE: EtOAc=1:1 to give the title compound. LC/MS (ESI) m/z 414.2 (M+H)
$^1$H NMR (CDCl$_3$, 400 MHz): δ 8.05-8.16 (m, 1H), 7.61 (br. s., 1H), 7.35-7.43 (m, 1H), 7.18-7.25 (m, 1H), 7.07-7.13 (m, 1H), 5.94-6.20 (m, 1H), 5.22-5.68 (m, 1H), 4.22-4.36 (m, 2H), 3.77 (s, 4H), 3.16-3.33 (m, 1H), 2.14-3.02 (m, 2H), 1.23-1.39 (m, 6H).

Step I: Ethyl (5R)-2$^4$-((methoxycarbonyl)amino)-5-methyl-4-oxo-3-aza-1(5,2)-oxazola-2(1,2)-benzenacyclononaphane-9-carboxylate A mixture of ethyl (5R,E)-2$^4$-((methoxycarbonyl)amino)-5-methyl-4-oxo-3-aza-1(5,2)-oxazola-2(1,2)-benzenacyclononaphan-6-ene-9-carboxylate (50 mg, 0.121 mmol), Pd—C(10%, 10 mg, 9.40 μmol) in MeOH (5 mL) was stirred at 30° C. for 2 hrs. The mixture was filtered through Celite and the filter cake was washed with MeOH (10 mL). The combined filtrates were concentrated and the residue was dried under vacuum to give the title compound, which was used in the next step without further purification. LC/MS (ESI) m/z 416.2 (M+1).

Step J: (5R)-2$^4$-((Methoxycarbonyl)amino)-5-methyl-4-oxo-3-aza-1(5,2)-oxazola-2(1,2)-benzenacyclononaphane-9-carboxylic Acid To a stirred mixture of ethyl (5R)-2$^4$-((methoxycarbonyl)amino)-5-methyl-4-oxo-3-aza-1(5,2)-oxazola-2(1,2)-benzenacyclononaphane-9-carboxylate (10 mg, 0.024 mmol) in THF (1 mL), water (1 mL) and MeOH (1 mL) was added LiOH H$_2$O (2.0 mg, 0.048 mmol) at 25° C. and the mixture was stirred at 25° C. for 3 hrs. The reaction mixture was concentrated, diluted with water (3 mL) and adjusted to pH 3 with 1 N HCl, some solid separated out from mixture. The mixture was extracted with EtOAc (3×50 mL). The combined organic fractions were dried over Na$_2$SO$_4$, filtered and evaporated under reduced pressure to give the title compound, which was used in the next step without further purification. LC/MS (ESI) m/z 388.2 (M+1)

Step K: Methyl ((5R,9R)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2$^4$-yl) carbamate (EX-14a) and Methyl ((5R,9S)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2$^4$-yl)carbamate (EX-14b)

To a mixture of (5R)-2$^4$-((methoxycarbonyl)amino)-5-methyl-4-oxo-3-aza-1(5,2)-oxazola-2(1,2)-benzenacyclononaphane-9-carboxylic acid (20 mg, 0.039 mmol) in DMF (2 mL) was added (R)-6-chloro-5-fluorospiro[benzo[d][1,3]oxazine-4,3'-piperidin]-2(1H)-one (15.72 mg, 0.058 mmol), HATU (44.2 mg, 0.116 mmol), DIPEA (0.020 mL, 0.116 mmol) at 25° C. and the mixture was stirred at 25° C. for 3 h. The mixture was diluted with water (5 mL) and extracted with EtOAc (2×10 mL). The combined organic fractions were washed with brine (2×10 mL), dried over Na$_2$SO$_4$, filtered and evaporated under reduced pressure. The residue was purified by prep-HPLC to give EX-14a (fast-eluting) as a solid and EX-14b (slow-eluting) as a solid.

EX-14a $^1$H NMR (CD$_3$OD, 400 MHz): δ 7.51-7.59 (m, 1H), 7.38-7.47 (m, 3H), 7.21-7.28 (m, 1H), 6.73 (t, J=7.4 Hz, 1H), 4.52-4.76 (m, 1H), 4.20-4.46 (m, 1H), 3.83-4.15 (m, 2H), 3.74 (d, J=3.1 Hz, 4H), 3.08-3.24 (m, 1H), 2.70-2.92 (m, 2H), 2.39-2.57 (m, 1H), 2.26 (d, J=13.0 Hz, 2H), 1.72 (d, J=13.5 Hz, 2H), 1.37 (t, J=6.4 Hz, 2H), 1.22-1.31 (m, 2H), 1.15 (d, J=6.0 Hz, 3H). MS (ESI) m/z 640.2 (M+H)

EX-14b $^1$H NMR (CD$_3$OD, 400 MHz): δ 7.55-7.65 (m, 1H), 7.39-7.50 (m, 3H), 7.23-7.31 (m, 1H), 6.70-6.80 (m, 1H), 4.60-4.72 (m, 1H), 4.42 (d, J=9.0 Hz, 1H), 4.22-4.35 (m, 1H), 3.88-4.05 (m, 1H), 3.75 (s, 3H), 3.10-3.25 (m, 1H), 2.78-3.00 (m, 2H), 2.42-2.62 (m, 2H), 2.19-2.35 (m, 2H), 2.02 (d, J=9.0 Hz, 2H), 1.81 (d, J=15.9 Hz, 1H), 1.46-1.60 (m, 2H), 1.22-1.27 (m, 3H). MS (ESI) m/z 640.2 (M+H)

By using procedures similar to those described above, the following compounds were synthesized and characterized by LCMS.

| Example | Structure | LCMS [M + 1] | Hu FXIa Ki (nM) |
|---|---|---|---|
| 14a | methyl ((5R,9R)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2$^4$-yl)carbamate | 640.2 | 13.4 |
| 14b | methyl ((5R,9S)-9-((R)-6-chloro-5-fluoro-2-oxo-1,2-dihydrospiro[benzo[d][1,3]oxazine-4,3'-piperidine]-1'-carbonyl)-5-methyl-4-oxo-3-aza-1(5,2)-oxazola-2(1,2)-benzenacyclononaphane-2$^4$-yl)carbamate | 640.2 | 217 |

Example 15
Methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-2⁴-yl)carbamate (EX-15)
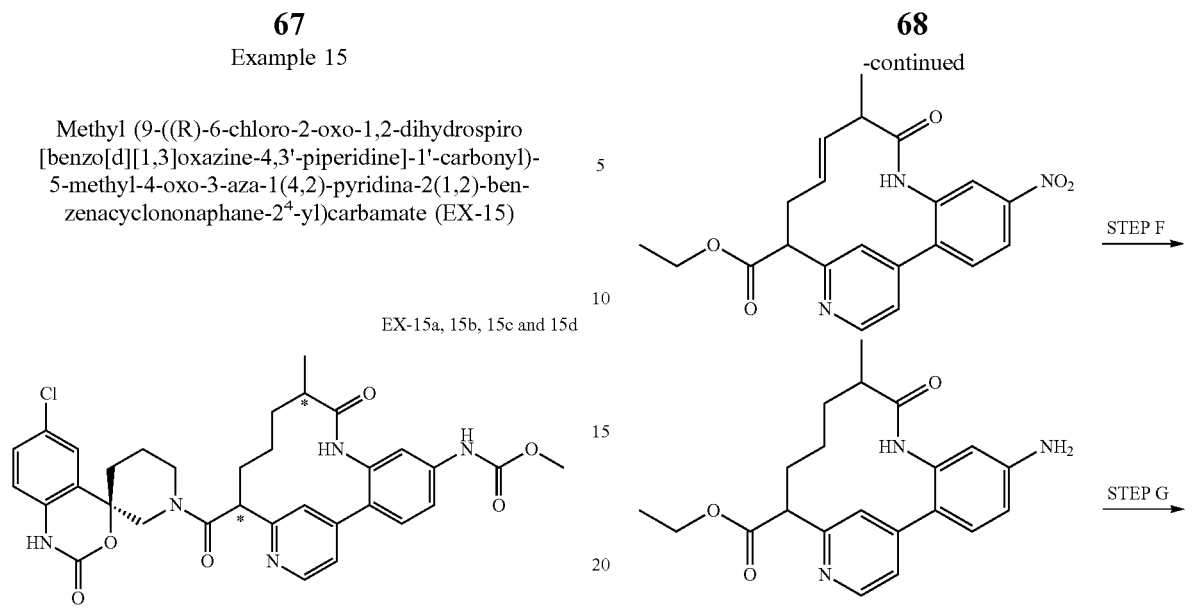
Synthetic Scheme for Example 15
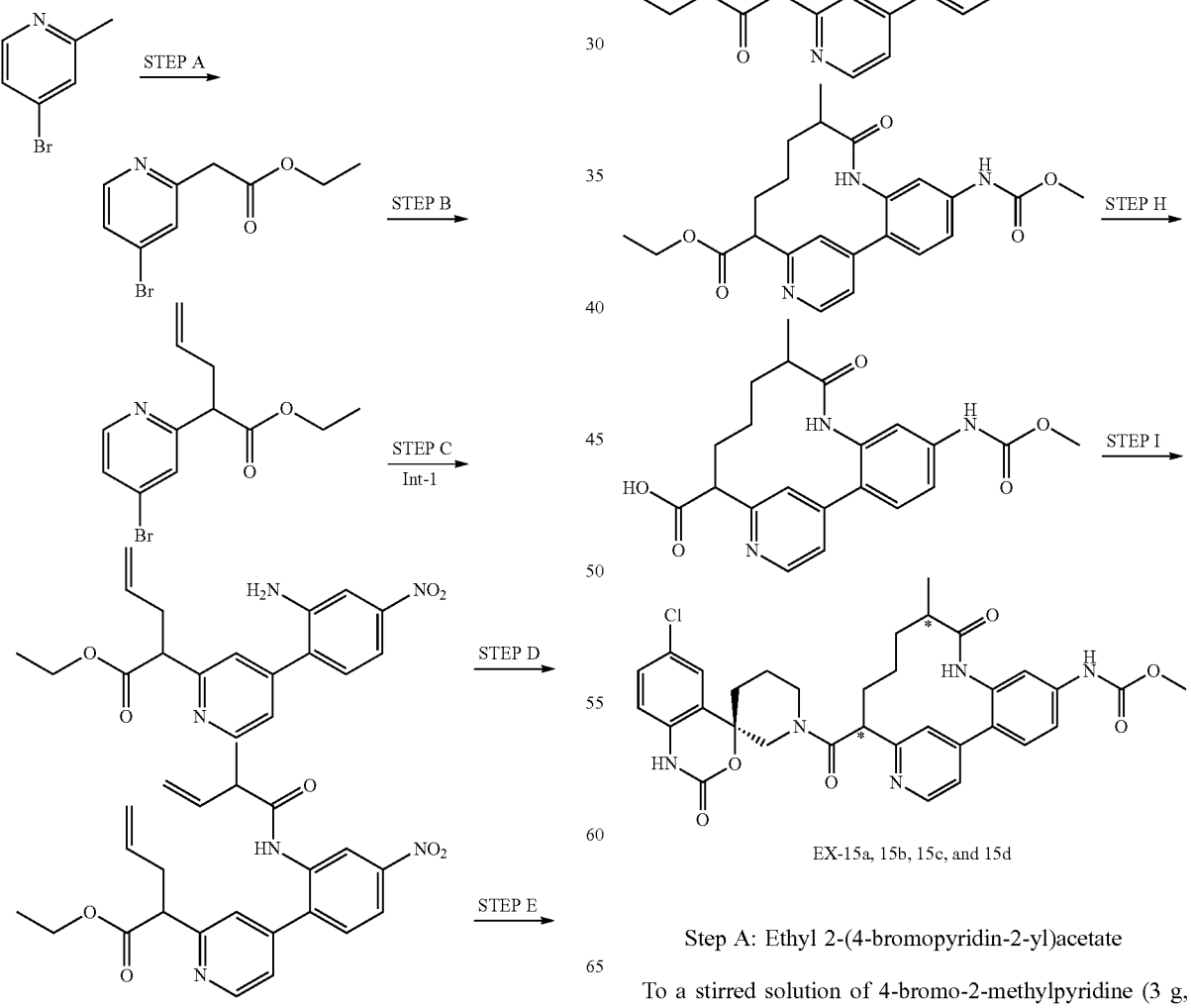
Step A: Ethyl 2-(4-bromopyridin-2-yl)acetate
To a stirred solution of 4-bromo-2-methylpyridine (3 g, 17.44 mmol) and diethyl carbonate (2.75 ml, 22.67 mmol) in THF (30 ml) was added LDA (4 mL) (2M in THF/hept/ethylbenzene) at −78° C. The solution was stirred for 1 h prior to the addition of another portion of LDA (4.00 mL). Stirring was continued at −70° C. for one more hour and then the reaction was quenched by the addition of water. The resulting mixture was extracted with ethyl acetate and the combined extracts were washed with brine and dried ($Na_2SO_4$). The solvent was evaporated and the residue was purified by flash column chromatography on silica gel (0-100% EtOAc in Hex) to give the title compound. LC/MS=245.75 [M+1]

Step B: Ethyl 2-(4-bromopyridin-2-yl)pent-4-enoate

To a solution of ethyl 2-(4-bromopyridin-2-yl)acetate (1.72 g, 7.05 mmol) in THF (23.49 ml) was added dropwise LDA (4.05 ml, 8.10 mmol, 2M solution in THF) and the resulting mixture was stirred for 40 min at −78° C. Allyl bromide (0.610 ml, 7.05 mmol) was added dropwise, and the stirring was continued at −78° C. for 2 h and checked by LCMS (little desired product). The reaction mixture was slowly warmed to RT and stirred at RT for 1 hr (the reaction complete). The reaction was quenched by adding a saturated aqueous solution of $NH_4Cl$ (20 mL). The aqueous layer was extracted with $Et_2O$ (2×20 mL), the organic phases were combined, washed with HCl (1 M, 20 mL), brine (20 mL), dried over $MgSO_4$, filtered and concentrated under vacuum. The crude product was purified by flash column chromatography on silica gel (1/1 EtOAc/Hex) to give the title compound. LC/MS=285.77 [M+1]

Step C: Ethyl 2-(4-(2-amino-4-nitrophenyl)pyridin-2-yl)pent-4-enoate

To a RBF was added 2-(5,5-dimethyl-1,3,2-dioxaborinan-2-yl)-5-nitroaniline (Int-1, 2.53 g, 10.14 mmol), ethyl 2-(4-bromopyridin-2-yl)pent-4-enoate (1.44 g, 5.07 mmol), 1,1'-bis(diphenylphosphino)ferrocene-Palladium (II) dichloride DCM Complex (0.414 g, 0.507 mmol) and $K_3PO_4$ (2.151 g, 10.14 mmol). The RBF was equipped with a reflux condensor then the appraratus was purged with $N_2$ for several minutes. Next, degassed DMSO (26 ml) was added followed by degassed water (570 μL). The reaction mixture was heated to 90° C. for 5 h under $N_2$ stream. After cooling to RT, water was poured into the reaction and the reaction mixture was extracted with EtOAc. The organic solvent was washed with brine, dried over $MgSO_4$, filtered and concentrated. The crude product was purified by flash column chromatography on silica gel (EtOAc/Hex=1/1) to provide the title compound. LC/MS=341.8 [M+1]

Step D: ethyl 2-(4-(2-(2-methylbut-3-enamido)-4-nitrophenyl)pyridin-2-yl)pent-4-enoate To a stirred solution of ethyl 2-(4-(2-amino-4-nitrophenyl)pyridin-2-yl)pent-4-enoate (1.6 g, 4.69 mmol) in ethyl acetate (18.03 ml) was added 2-methyl-3-butenoic acid (0.700 ml, 6.09 mmol), T3P (5.58 ml, 9.37 mmol) and DIPEA (2.456 ml, 14.06 mmol) at RT. The reaction mixture was stirred at RT overnight. The reaction mixture was diluted with EtOAc and the organi layer was washed with sat. $NaHCO_3$, dired over $MgSO_4$, filtered and concentrated. The crude product was purified by flash column chromatography on silica gel (EtOAc/Hex=1/1) to give the title compound. LC/MS=423.91 [M+1]

Step E: Ethyl (E)-5-methyl-$2^4$-nitro-4-oxo-3-aza-1(4,2)-pyridina-2(1,2)-benzenacyclononaphan-6-ene-9-carboxylate To a RBF was added ethyl 2-(4-(2-(2-methylbut-3-enamido)-4-nitrophenyl)pyridin-2-yl)pent-4-enoate (1.44 g, 3.40 mmol), pTSA (0.712 g, 3.74 mmol) and DCE (283 ml). The flask was equipped with a reflux condensor and the clear yellow solution was degassed with $N_2$ for 30 min. The reaction was then warmed to reflux for 1 h. Then a solution of Zhan Catalyst 1B (0.449 g, 0.612 mmol) in DCM (0.5 mL) was added dropwise to the reaction mixture. After 4 hrs at reflux, the reaction was cooled to RT, washed with saturated $Na_2CO_3$, brine, dried over $MgSO_4$, filtered, and concentrated to give brown solid. The crude product was then purified by flash column chromatography on silica gel (0-100% EtOAc in Hex) to give the title compound. LC/MS=396.13 [M+1]

Step F: Ethyl $2^4$-amino-5-methyl-4-oxo-3-aza-1(4,2)-pyridina-2(1,2)-benzenacyclononaphane-9-carboxylate To a Parr-Shaker tube containing ethyl (E)-5-methyl-$2^4$-nitro-4-oxo-3-aza-1(4,2)-pyridina-2(1,2)-benzenacyclononaphan-6-ene-9-carboxylate (333.9 mg, 0.844 mmol) was added MeOH (42 mL) and ethyl acetate (5 mL), and Pd—C(270 mg, 0.253 mmol) (10% activated). The reaction tube was connected to hydrogenation Parr-Shaker under 10 atm $H_2$ pressure for overnight. The reaction mixture was filltered through a short pad of Celite and the filtrate was evaporated. The crude product was purified by flash column chromatography on silica gel (10% MeOH/DCM) to provide the title compound. LC/MS=367.92 [M+1]

Step G: Ethyl $2^4$-((methoxycarbonyl)amino)-5-methyl-4-oxo-3-aza-1(4,2)-pyridina-2(1,2)-benzenacyclononaphane-9-carboxylate To a stirred solution of ethyl $2^4$-amino-5-methyl-4-oxo-3-aza-1(4,2)-pyridina-2(1,2)-benzenacyclononaphane-9-carboxylate (310 mg, 0.844 mmol) in THF (8437 μl) was added $Na_2CO_3$ (94 mg, 0.886 mmol) and methyl carbonochloridate (65.2 μl, 0.844 mmol) at 0° C. The reaction mixture was warmed to RT and stirred at RT for 16 hrs. Water was added and extracted with EtOAc. The organic layer was washed with brine, dried over $MgSO_4$, filtered and concentrated. The crude product was purified by flash column chromatography on silica gel (EtOAc/Hex=1/1 to 100% EtOAc) to give the title compound. LC/MS=426.17 [M+1]

Step H: $2^4$-((Methoxycarbonyl)amino)-5-methyl-4-oxo-3-aza-1(4,2)-pyridina-2(1,2)-benzenacyclononaphane-9-carboxylic Acid To a solution of ethyl $2^4$-((methoxycarbonyl)amino)-5-methyl-4-oxo-3-aza-1(4,2)-pyridina-2(1,2)-benzenacyclononaphane-9-carboxylate] in THF (4 mL) was added a solution of LiOH $H_2O$ (24.66 mg, 0.588 mmol) in water (1.5 mL) and MeOH (1 mL) at RT. The reaction mixture was stirred at RT for overnight. LCMS showed the reaction was complete. 1N HCl was added until pH=6.5. The solvent was evaporated and the crude product was dried in a vac. oven overnight to afford the title compound. LC/MS=398.1 [M+1]

Step I: Methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-2⁴-yl)carbamate (EX-15)

To a stirred solution of (R)-6-chlorospiro[benzo[d][1,3]oxazine-4,3'-piperidin]-2(1H)-one hydrochloride (204 mg, 0.707 mmol) in DMF (5888 μl) was added 2⁴-((methoxycarbonyl)amino)-5-methyl-4-oxo-3-aza-1(4,2)-pyridina-2(1,2)-benzenacyclononaphane-9-carboxylic acid (234 mg, 0.589 mmol), HATU (269 mg, 0.707 mmol) and DIPEA (411 μl, 2.355 mmol) at RT. The reaction mixture wa stirred at RT for 3 hrs. Sat. NaHCO₃ was added and the reaction mixture was diluted with EtOAc. The organic layer was washed with brine, dried over MgSO₄, filtered and concentrated. The crude product was purified by flash column chromatography on silica gel (1/1EtOAc/Hex to 10% MeOH in DCM) to afford the title compound. LC/MS=632.08 [M+1]. Four diastereomers were resolved by chiral SFC separation (IC-H column, 50% 2:1 MeOH:MeCN/CO₂, 100 bar, 35° C., 220 nm) to afford Example 15a (first peak), Example 15b (second peak), Example 15c (third peak), and Example 15d (fourth peak). LC/MS=632.1 [M+1] for all four isomers By using procedures similar to those described above, the following compounds were synthesized and characterized.

| Example | Structure | LCMS [M + 1] | Hu FXIa Ki (nM) |
|---|---|---|---|
| 15a | methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-2⁴-yl)carbamate (isomer a) | 632.08 | 31.1 |
| 15b | methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-2⁴-yl)carbamate (isomer b) | 632.08 | 749 |
| 15c | methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-2⁴-yl)carbamate (isomer c) | 632.08 | 1762 |

| Example | Structure | LCMS [M + 1] | Hu FXIa Ki (nM) |
|---|---|---|---|
| 15d | 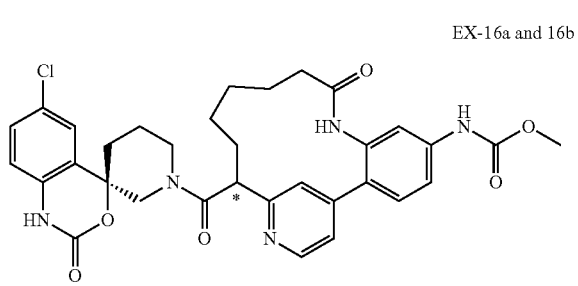 [SMILES: COC(=O)Nc1ccc2c(c1)NC(=O)CCCCCC(C(=O)N1CCC[C@@]3(C1)OC(=O)Nc1ccc(Cl)cc13)c1cc-2ccn1] methyl (9-((R)-6-chloro-2-oxo-1,2-dihydrospiro[benzo[d][1,3]oxazine-4,3'-piperidine]-1'-carbonyl)-5-methyl-4-oxo-3-aza-1(4,2)-pyridina-2(1,2)-benzenacyclononaphane-$2^4$-yl)carbamate (isomer d) | 632.08 | >5000 |

Example 16

Methyl (10-((R)-6-chloro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-$2^4$-yl)carbamate (EX-16)

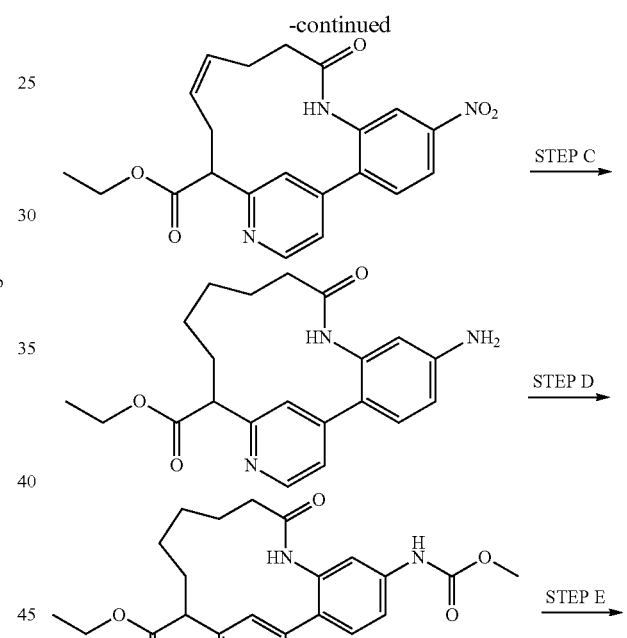

EX-16a and 16b

Synthetic Scheme for Example 16

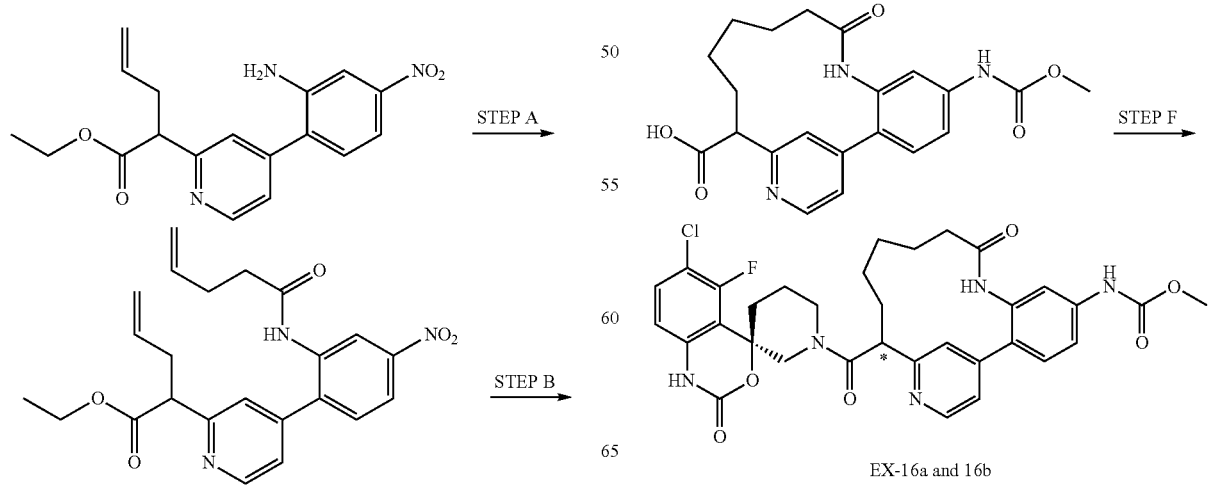

EX-16a and 16b

Step A: Ethyl 2-(4-(4-nitro-2-(pent-4-enamido)phenyl)pyridin-2-yl)pent-4-enoate To a solution of ethyl 2-(4-(2-amino-4-nitrophenyl)pyridin-2-yl)pent-4-enoate (2.37 g, 6.94 mmol) and TEA (2.0 ml, 14.35 mmol) in DCM (20 ml) at −10° C. was added 4-pentenoyl chloride (0.988 g, 8.33 mmol). It was stirred for 15 min and was purified by flash column chromatography on silica gel (0-70% ethyl acetate in hexane) to give the title compound. LC/MS (ES) m/z: 424 (M+1).

Step B: Ethyl (Z)-2⁴-nitro-4-oxo-3-aza-1(4,2)-pyridina-2(1,2)-benzenacyclodecaphan-7-ene-10-carboxylate and Ethyl (E)-2⁴-nitro-4-oxo-3-aza-1(4,2)-pyridina-2(1,2)-benzenacyclodecaphan-7-ene-10-carboxylate A solution of ethyl 2-(4-(4-nitro-2-(pent-4-enamido)phenyl)pyridin-2-yl)pent-4-enoate (2.63 g, 6.21 mmol) and Zhan Catalyst 1B (1.4 g, 1.908 mmol) in DCE (400 ml) was degassed by bubbling nitrogen for 15 min. To the solution was added Ts-O H (1.300 g, 6.83 mmol). The solids were slowly dissolved by stirring at 80° C. for 30 min. It was cooled by an ice-bath and transferred to two sealed tubes by a cannula under nitrogen. The tubes were sealed and heated at 120° C. for 30 min. They were allowed to cooled to RT and the reaction mixtures were combined in to a separatory funnel. It was washed with saturated aqueous sodium bicarbonate. The organic layer was dried over sodium sulfate, filtered and concentrated under reduced pressure. The residue was purified by flash column chromatography on silica gel (0-100% ethyl aceate in hexane) to give the Z-isomer and the E-isomer of the title compound.

Z-isomer: MS (ES) m/z: 396 (M+H); $^1$H NMR (500 MHz, CHCl$_3$-d): δ 8.85 (s, 1H), 8.75 (d, 1H), 8.10 (dd, 1H), 7.46 (d, 1H), 7.20 (m, 2H), 5.61 (m, 1H), 5.28 (m, 1H), 4.22 (m, 2H), 3.99 (m, 1H), 2.77 (m, 2H), 2.42 (m, 4H), 1.23 (t, 3H).

E-isomer: MS (ES) m/z: 396 (M+H); $^1$H NMR (500 MHz, CHCl$_3$-d): δ 8.83 (s, 1H), 8.73 (d, 1H), 8.12 (d, 1H), 7.50 (d, 1H), 7.40 (m, 1H), 7.22 (d, 1H), 5.41 (m, 1H), 4.20 (m, 2H), 4.18 (m, 2H), 2.98 (m, 1H), 2.80-2.60 (m, 2H), 2.50-2.15 (m, 2H), 2.12 (m, 1H), 1.23 (t, 3H).

Step C: Ethyl 2⁴-amino-4-oxo-3-aza-1(4,2)-pyridina-2(1,2)-benzenacyclodecaphane-10-carboxylate To a 250 mL par-shaker was added the Z-isomer from Step B (1.15 g, 2.91 mmol), Pd—C(0.619 g, 10 wt %, 0.291 mmol) and EtOH (30 mL). It was purged with nitrogen three times and hydrogen three times and shaken under hydrogen (20 psi) overnight. It was filtered through a pad of Celite and the filtrate was concentrated under reduced pressure. The residue was purified by flash column chromatography on silica gel (0-10% MeOH in DCM) to give the title compound. LC/MS (ES) m/z: 368 (M+1).

Step D: Ethyl 2⁴-((methoxycarbonyl)amino)-4-oxo-3-aza-1(4,2)-pyridina-2(1,2)-benzenacyclodecaphane-10-carboxylate To a mixture of ethyl 2⁴-amino-4-oxo-3-aza-1(4,2)-pyridina-2(1,2)-benzenacyclodecaphane-10-carboxylate (200 mg, 0.54 mmol) and sodium carbonate (115 mg, 0.544 mmol) in THF (2 ml) was added methyl chloroformate (0.50 ml, 0.65 mmol) at 0° C. It was stirred for 15 min and was allowed to stir at RT for another 1 h. It was diluted with ethyl acetate (10 mL) and washed with brine (10 mL). The organic layer was dried over sodium sulfate, filtered and concentrated under reduced pressure. The residue was purified by flash column chromatography on silica gel (0-10% methanol in DCM) to give the title compound as a solid. LC/MS (ES) m/z: 426 (M+1).

Step E: 2⁴-((Methoxycarbonyl)amino)-4-oxo-3-aza-1(4,2)-pyridina-2(1,2)-benzenacyclodecaphane-10-carboxylic Acid A suspension of ethyl 2⁴-((methoxycarbonyl)amino)-4-oxo-3-aza-1(4,2)-pyridina-2(1,2)-benzenacyclodecaphane-10-carboxylate (117 mg, 0.275 mmol) in THF (1.5 mL) and MeOH (1.5 mL), water (1.5 mL) was added aq. LiOH (5 M, 0.1 mL, 0.500 mmol). The mixture was stirred at 60° C. for 1 h. It was cooled to RT and acidified with 4 M HCl to pH 5. The mixture was diluted with water. Precipitates crashed out. It was aged for 1 h and the solids were collected by filtration to give the title compound. LC/MS (ES⁺) m/z: 398 (M+1).

Step F: Methyl (10-((R)-6-chloro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-2⁴-yl)carbamate (EX-16)

To a solution of (R)-6-chloro-2-oxo-1,2-dihydrospiro[benzo[d][1,3]oxazine-4,3'-piperidin]-1'-ium chloride (29.7 mg, 0.103 mmol) and 2⁴-((methoxycarbonyl)amino)-4-oxo-3-aza-1(4,2)-pyridina-2(1,2)-benzenacyclodecaphane-10-carboxylic acid (34 mg, 0.086 mmol) in DMF (1 ml) was added DIEA (0.045 ml, 0.257 mmol). The mixture was stirred for 5 min and HATU (42.3 mg, 0.111 mmol) was added. The mixture was stirred at rt overnight. It was purified by flash column chromatography on silica gel (0-10% methanol in DCM) to give mixture of two diastereomer as a solid. A sample of this mixture was separated by SFC (ChiralCel OD, 2×25 cm, 100 bar, 60% MeOH (0.2% DEA)/CO₂, 60 mL/min, 35° C.) to give EX-16a (slower isomer). MS (ES⁺) m/z: 632 (M+H) and EX-16b (faster isomer). MS (ES⁺) m/z: 632 (M+H).

Example 20

(4R)-1'-((Z)-2⁴-amino-4-oxo-3-aza-1(4,2)-pyridina-2(1,2)-benzenacyclodecaphan-7-ene-10-carbonyl)-6-chloro-5-fluorospiro[benzo[d][1,3]oxazine-4,3'-piperidin]-2(1H)-one (EX-20)

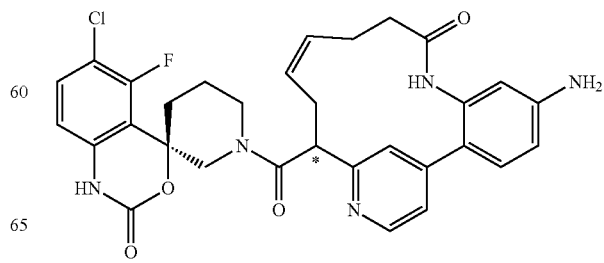

EX-20a and 20b

Synthetic Scheme for Example 20

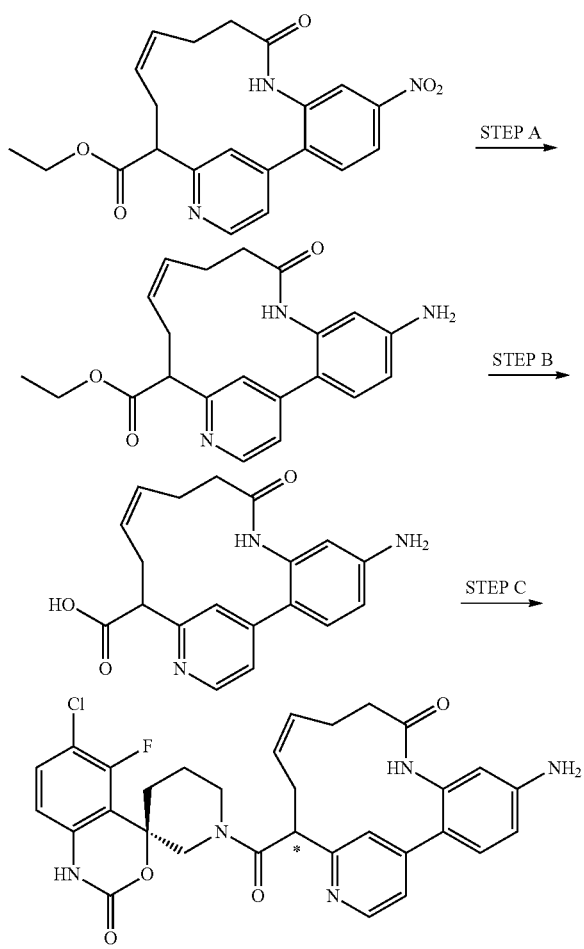

EX-20a and 20b

Step A: Ethyl (Z)-2⁴-amino-4-oxo-3-aza-1(4,2)-pyridina-2(1,2)-benzenacyclodecaphan-7-ene-10-carboxylate To a solution of ethyl (Z)-2⁴-nitro-4-oxo-3-aza-1(4,2)-pyridina-2(1,2)-benzenacyclodecaphan-7-ene-10-carboxylate (100 mg, 0.253 mmol) in 2-propanol (3 ml) was added iron powder (42.4 mg, 0.759 mmol) and saturated aqueous ammonium chloride (3 ml, 0.253 mmol). The mixture was stirred at 80° C. for 2 h and was allowed to cool to rt. To the mixture was added 20 mL of ethyl acetate and it was filtered through a pad of Celite. The filtrate was washed with brine (10 mL). The organic layer was dried over sodium sulfate, filtered and concentrated under reduced pressure. The residue was purified by flash column chromatography on silica gel (0-5% methanol in DCM) to give the title compound as a solid. MS (ES$^+$) m/z: 366 (M+1).

Step B: (Z)-2⁴-amino-4-oxo-3-aza-1(4,2)-pyridina-2(1,2)-benzenacyclodecaphan-7-ene-10-carboxylic Acid To a suspension of the product form ethyl (Z)-2⁴-amino-4-oxo-3-aza-1(4,2)-pyridina-2(1,2)-benzenacyclodecaphan-7-ene-10-carboxylate (56 mg, 0.153 mmol) in THF (1.5 mL), water (1.500 mL) and MeOH (1.5 mL) was added aq. LiOH (5M, 0.1 mL, 0.500 mmol). It was heated at 60° C. for 1 h and cooled to rt. The mixture was neutralized with 4 M HCl to pH 5. It was concentrated under reduced pressure overnight to give the title compound, which was used without purification.

Step C: (R)-1'-((R,Z)-2⁴-amino-4-oxo-3-aza-1(4,2)-pyridina-2(1,2)-benzenacyclodecaphan-7-ene-10-carbonyl)-6-chloro-5-fluorospiro[benzo[d][1,3]oxazine-4,3'-piperidin]-2(1H)-one (EX-20a) and (R)-1'-((S,Z)-2⁴-amino-4-oxo-3-aza-1(4,2)-pyridina-2(1,2)-benzenacyclodecaphan-7-ene-10-carbonyl)-6-chloro-5-fluorospiro[benzo[d][1,3]oxazine-4,3'-piperidin]-2(1H)-one (EX-20b)

To a solution of (R)-6-chloro-5-fluoro-2-oxo-1,2-dihydrospiro[benzo[d][1,3]oxazine-4,3'-piperidin]-1'-ium chloride (61.2 mg, 0.199 mmol) and product form Step 2 (56 mg, 0.166 mmol) in DMF (1 ml) was added DIEA (0.087 ml, 0.498 mmol). The mixture was stirred for 5 min and added HATU (82 mg, 0.216 mmol). The solution was stirred at rt for 1 h and purified directly by flash column chromatography on silica gel (0-10% MeOH in DCM) to give a mixture of two diastereomers. A sample of the mixture was separated by SFC (OD-H, 2×15 cm, 40% methanol (0.1% DEA)/CO$_2$, 100 bar, 50 mL/min, 35° C.) to give EX-20a as a solid. MS (ES) m/z: 590 (M+1) and slower-eluting EX-20b as a solid. MS (ES) m/z: 590 (M+1).

By using procedures similar to those described above, the following compounds were synthesized and characterized.

| Example | LCMS Structure | [M + 1] | Hu FXIa Ki (nM) |
|---|---|---|---|
| 16a | methyl ((S)-10-((R)-6-chloro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-2⁴-yl)carbamate | 632 | >875 |

-continued

| Example | LCMS Structure | [M + 1] | Hu FXIa Ki (nM) |
|---|---|---|---|
| 16b | methyl ((R)-10-((R)-6-chloro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-2⁴-yl)carbamate | 632 | 284 |
| 17a | methyl ((R)-9-((R)-6-chloro-2-oxo-1,2-dihydrospiro[benzo[d][1,3]oxazine-4,3'-pyrrolidine]-1'-carbonyl)-4-oxo-3-aza-1(4,2)-pyridina-2(1,2)-benzenacyclononaphane-2⁴-yl)carbamate | 604 | 9.2 |
| 17b | methyl ((S)-9-((R)-6-chloro-2-oxo-1,2-dihydrospiro[benzo[d][1,3]oxazine-4,3'-pyrrolidine]-1'-carbonyl)-4-oxo-3-aza-1(4,2)-pyridina-2(1,2)-benzenacyclononaphane-2⁴-yl)carbamate | 604 | >8750 |
| 18a | methyl ((R)-10-((R)-6-chloro-5-fluoro-2-oxo-1,2-dihydrospiro[benzo[d][1,3]oxazine-4,3'-pyrrolidine]-1'-carbonyl)-4-oxo-3-aza-1(4,2)-pyridina-2(1,2)-benzenacyclodecaphane-2⁴-yl)carbamate | 636 | 8.6 |

| Example | LCMS Structure | [M + 1] | Hu FXIa Ki (nM) |
|---|---|---|---|
| 18b | methyl ((S)-10-((R)-6-chloro-5-fluoro-2-oxo-1,2-dihydrospiro[benzo[d][1,3]oxazine-4,3'-pyrrolidine]-1'-carbonyl)-4-oxo-3-aza-1(4,2)-pyridina-2(1,2)-benzenacyclodecaphane-$2^4$-yl)carbamate | 636 | 198 |
| 19a | methyl ((R)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-$2^4$-yl)carbamate | 650 | 49 |
| 19b | methyl ((S)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphane-$2^4$-yl)carbamate | 650 | >875 |
| 20a | (R)-1'-((R,Z)-$2^4$-amino-4-oxo-3-aza-1(4,2)-pyridina-2(1,2)-benzenacyclodecaphan-7-ene-10-carbonyl)-6-chloro-5-fluorospiro[benzo[d][1,3]oxazine-4,3'-piperidin]-2(1H)-one | 590 | 211 |

-continued

| Example | LCMS Structure | [M + 1] | Hu FXIa Ki (nM) |
|---|---|---|---|
| 20b | (R)-1'-((S,Z)-2⁴-amino-4-oxo-3-aza-1(4,2)-pyridina-2(1,2)-benzenacyclodecaphan-7-ene-10-carbonyl)-6-chloro-5-fluorospiro[benzo[d][1,3]oxazine-4,3'-piperidin]-2(1H)-one | 590 | >875 |
| 21a | methyl ((R,E)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphanen-2⁴-yl)carbamate | 648 | 59.4 |
| 21b | methyl ((S,E)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphanen-2⁴-yl)carbamate | 648 | >875 |
| 22a | methyl ((R,Z)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphanen-2⁴-yl)carbamate | 648 | 2.88 |

| Example | LCMS Structure | [M + 1] | Hu FXIa Ki (nM) |
|---|---|---|---|
| 22b | 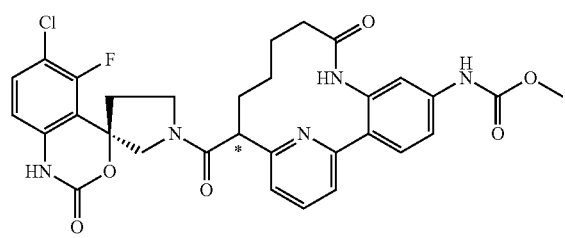 methyl ((S,Z)-10-((R)-6-chloro-5-fluoro-2-oxo-1,2-dihydrospiro[benzo[d][1,3]oxazine-4,3'-piperidine]-1'-carbonyl)-4-oxo-3-aza-1(4,2)-pyridina-2(1,2)-benzenacyclodecaphanen-2⁴-yl)carbamate | 648 | >875 |
Example 23
Methyl (9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,6)-pyridina-2(1,2)-benzenacyclononaphane-2⁴-yl)carbamate (EX-23)
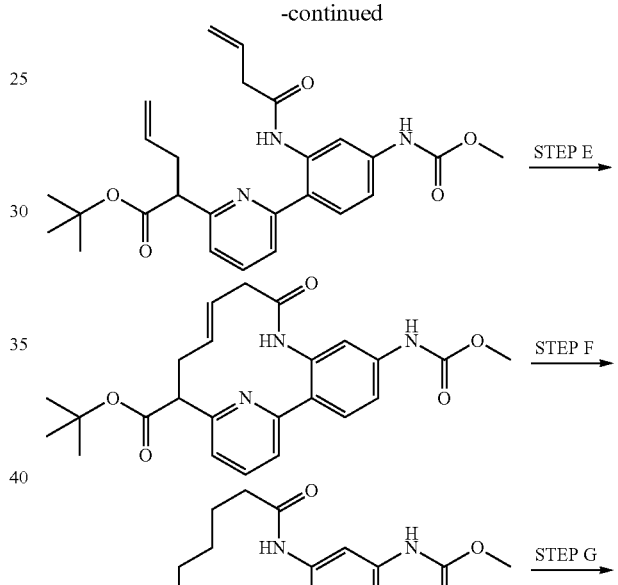
Synthetic Scheme for Example 23
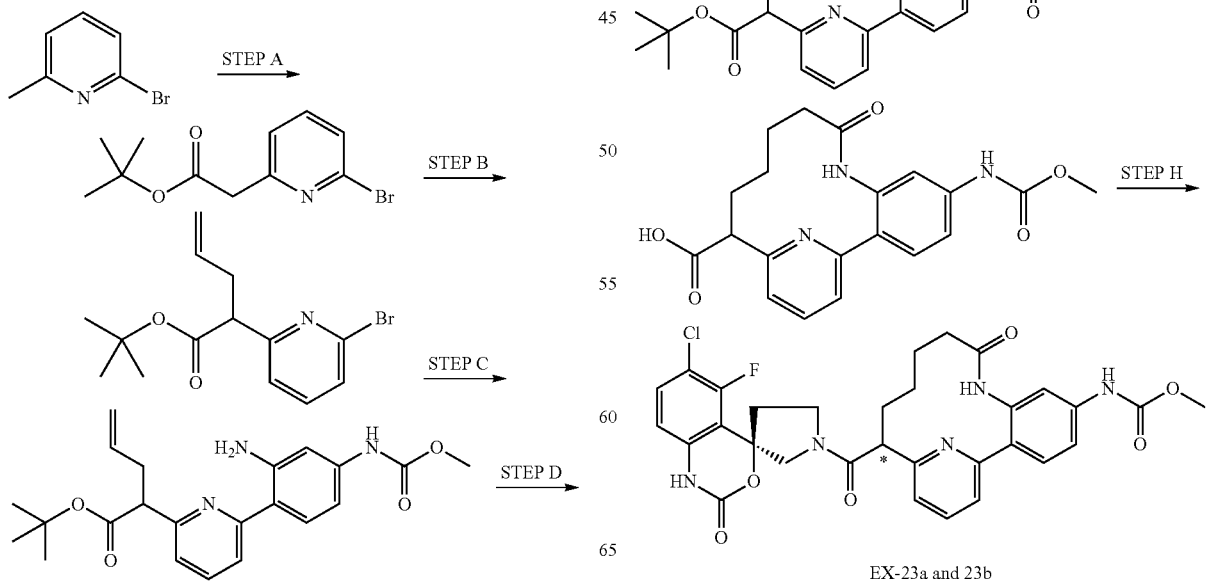

Step A: tert-Butyl 2-(6-bromopyridin-2-yl)acetate

To a solution of diisopropylamine (25.9 g, 256 mmol) in THF (300 mL) at −78° C. was added dropwise n-BuLi (102 mL, 256 mmol) (2.5 M solution in hexane) over a period of 15 min and the resulting mixture was stirred at −78° C. for an additional 30 min. To the above LDA solution was added 2-bromo-6-methylpyridine (40 g, 233 mmol) in THF (100 mL) dropwise and the reaction mixture was stirred for −78° C. 1 h. Then di-tert-butyl dicarbonate (55.8 g, 256 mmol) was added and the reaction mixture was stirred at −78° C. for 4 hrs. The resulting mixture was diluted with water (50 mL) and extracted with EtOAc (2×100 mL). The combined organic layers were washed with water (50 mL), brine (30 mL), dried over $Na_2SO_4$, filtered and concentrated. The residue was purified by flash column chromatography on silica gel (0-5% EtOAc/PE gradient) to give the title compound.

$^1$H NMR ($CDCl_3$, 400 MHz): δ 7.43-7.53 (m, 1H), 7.35 (d, J=7.8 Hz, 1H), 7.23 (d, J=7.8 Hz, 1H), 3.84 (dd, J=6.7, 13.3 Hz, 2H), 1.39-1.44 (m, 9H).

Step B: tert-Butyl 2-(6-bromopyridin-2-yl)pent-4-enoate

To a solution of LDA (38.6 mL, 77 mmol, 2M in THF) in THF (100 mL) was added a solution of tert-butyl 2-(6-bromopyridin-2-yl)acetate (20 g, 73.5 mmol) in THF (20 mL) at −78° C. under $N_2$ protection and the mixture was stirred at −78° C. for 1 h. Then a solution of 3-bromoprop-1-ene (6.67 mL, 77 mmol) in THF (10 mL) was added dropwise for 15 min and the mixture was stirred at −78° C. for 2 hrs. The mixture was cooled, quenched with aqueous $NaHCO_3$ (saturated, 60 mL) and extracted with EtOAc (2×100 mL). The combined organic fractions were washed with brine (50 mL), dried over $Na_2SO_4$, filtered and concentrated, the residue was purified by flash column chromatography on silica gel (0~10% EtOAc/PE) to give the title compound.

$^1$H NMR: ($CD_3OD$, 400 MHz): δ 7.62-7.69 (m, 1H), 7.48 (d, J=7.5 Hz, 1H), 7.36 (d, J=7.5 Hz, 1H), 5.78 (d, J=7.0 Hz, 1H), 4.96-5.10 (m, 2H), 3.78 (t, J=7.5 Hz, 1H), 2.77 (d, J=6.5 Hz, 1H), 2.61 (d, J=7.0 Hz, 1H), 1.43 (s, 9H).

Step C: tert-Butyl 2-(6-(2-amino-4-((methoxycarbonyl)amino)phenyl)pyridin-2-yl)pent-4-enoate A mixture of tert-butyl 2-(6-bromopyridin-2-yl)pent-4-enoate (1.924 g, 6.16 mmol), methyl (3-amino-4-(4,4,5,5-tetramethyl-1,3,2-dioxaborolan-2-yl)phenyl)carbamate (1.5 g, 5.13 mmol), $K_3PO_4$ (2.180 g, 10.27 mmol), $PdCl_2(dppf)$ (0.188 g, 0.257 mmol) in dioxane (15 mL) and water (3 mL) was sealed in a 30 mL vial and stirred at 100° C. for 40 min under $N_2$ protection. The reaction mixture was cooled, diluted with water (35 mL) and extracted with EtOAc (3×50 mL). The combined organic fractions were washed with water (30 mL), brine (30 mL), dried over $Na_2SO_4$, filtered and the solvent was evaporated. The residue was purified by flash column chromatography on silica gel (0-30% EtOAc/PE) to give the title compound. LC/MS (ESI) m/z 398.1 (M+1).

1H NMR (400 MHz, $CD_3OD$): 7.74 (t, J=7.8 Hz, 1H), 7.56 (d, J=8.2 Hz, 1H), 7.47 (d, J=8.6 Hz, 1H), 7.12 (d, J=7.8 Hz, 1H), 6.99 (s, 1H), 6.74-6.81 (m, 1H), 5.78 (d, J=6.7 Hz, 1H), 4.92-5.09 (m, 2H), 3.78 (t, J=7.6 Hz, 1H), 3.71 (s, 3H), 2.80 (d, J=7.0 Hz, 1H), 2.60 (d, J=7.0 Hz, 1H), 1.38 (s, 9H).

Step D: tert-Butyl 2-(6-(2-(but-3-enamido)-4-((methoxycarbonyl)amino)phenyl)pyridin-2-yl)pent-4-enoate To a stirred solution of tert-butyl 2-(6-(2-amino-4-((methoxycarbonyl)amino) phenyl)pyridine-2-yl) pent-4-enoate (810 mg, 2.038 mmol) in DMF (15 mL) was added but-3-enoic acid (175 mg, 2.038 mmol), HATU (930 mg, 2.445 mmol) and DIPEA (1.424 mL, 8.15 mmol) at 25° C. The reaction mixture was stirred at 25° C. for 16 h. The reaction mixture was diluted with EtOAc and sat. $NaHCO_3$ (30 mL). The organic layer was separated, washed with brine (30 mL), dried over $Na_2SO_4$, filtered and concentrated. The residue was purified by prep-HPLC to give the title compound. LC/MS (ESI) m/z 466.1 (M+1).

$^1$H NMR: ($CD_3OD$, 400 MHz): δ 8.33 (s, 1H), 7.87 (t, J=7.8 Hz, 1H), 7.57-7.71 (m, 2H), 7.44 (d, J=8.0 Hz, 1H), 7.32 (d, J=7.6 Hz, 1H), 5.98 (d, J=6.8 Hz, 1H), 5.80 (d, J=6.8 Hz, 1H), 4.94-5.29 (m, 4H), 3.90 (t, J=7.6 Hz, 1H), 3.72 (s, 3H), 3.29 (d, J=6.1 Hz, 2H), 2.85 (d, J=7.0 Hz, 1H), 2.55-2.70 (m, 1H), 1.38 (s, 9H).

Step E: tert-Butyl (E)-2$^4$-((methoxycarbonyl)amino)-4-oxo-3-aza-1(2,6)-pyridina-2(1,2)-benzenacyclononaphan-6-ene-9-carboxylate A mixture of tert-butyl 2-(6-(2-(but-3-enamido)-4-((methoxycarbonyl)amino)phenyl)pyridin-2-yl)pent-4-enoate (153 mg, 0.329 mmol) and Zhan Catalyst-1B (72.3 mg, 0.099 mmol) in 1,2-dichloroethane (15 mL) was degassed by bubbling nitrogen for 15 min and the reaction mixture was stirred at 120° C. under nitrogen for 16 hrs. The mixture was cooled to RT and concentrated. The residue was diluted with EtOAc (20 mL), washed with aqueous $NaHCO_3$ (20 mL), brine (10 mL). The organic layer was separated, dried over $Na_2SO_4$, filtered and evaporated. The residue was purified by flash column chromatography on silica gel (0-50% EtOAc/PE) to give the title compound. LC/MS (ESI) m/z 438.1 (M+1).

Step F: tert-Butyl 2$^4$-((methoxycarbonyl)amino)-4-oxo-3-aza-1(2,6)-pyridina-2(1,2)-benzenacyclononaphane-9-carboxylate A mixture of tert-butyl (E)-2$^4$-((methoxycarbonyl)amino)-4-oxo-3-aza-1(2,6)-pyridina-2(1,2)-benzenacyclononaphan-6-ene-9-carboxylate (85 mg, 0.194 mmol) and Pd—C (41.4 mg, 0.039 mmol) (10%) in MeOH (30 mL) was stirred under 15 psi of $H_2$ at 28° C. for 4 hrs. LCMS showed most of the reactant was consumed. The mixture was filtered through a short pad of Celite and the filter cake was washed with MeOH (60 mL). The combined filtrates were evaporated to give the title compound, which was used in the next step without further purification. LC/MS (ESI) m/z 440.1 (M+1).

Step G: 2$^4$-((Methoxycarbonyl)amino)-4-oxo-3-aza-1(2,6)-pyridina-2(1,2)-benzenacyclononaphane-9-carboxylic Acid A mixture of tert-butyl 2$^4$-((methoxycarbonyl)amino)-4-oxo-3-aza-1(2,6)-pyridina-2(1,2)-benzenacyclononaphane-9-carboxylate (67 mg, 0.152 mmol) in HCl/dioxane (4M, 15 mL) was stirred at 25° C. for 16 hrs. The reaction mixture was concentrated to give the title compound, which was used in the next step without further purification. LC/MS (ESI) m/z 384.1 (M+1).

Step H: Methyl (9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,6)-pyridina-2(1,2)-benzenacyclononaphane-2$^4$-yl)carbamate (EX-23)

To a stirred solution of 2$^4$-((methoxycarbonyl)amino)-4-oxo-3-aza-1(2,6)-pyridina-2(1,2)-benzenacyclononaphane-9-carboxylic acid (46 mg, 0.120 mmol) in DMF (3 mL) was added HATU (54.7 mg, 0.144 mmol) at 25° C. The mixture was stirred for 10 min. Then a mixture of (R)-6-chloro-5-fluorospiro[benzo[d][1,3]oxazine-4,3'-pyrrolidin]-2(1H)-one hydrochloride (35.2 mg, 0.120 mmol) and DIPEA (0.084 mL, 0.480 mmol) in DMF (3 mL) was added. The reaction mixture was stirred at 25° C. for 12 hrs. The reaction mixture was diluted with EtOAc (30 mL) and sat. NaHCO$_3$ (aq) (30 mL). The organic layer was separated, washed with brine (20 mL), dried over Na$_2$SO$_4$, filtered and concentrated. The residue was purified by prep-HPLC the title compound (EX-23). MS (ESI) m/z 622.1 (M+H).

1H NMR (400 MHz, CD$_3$OD): 8.07-8.25 (m, 1H), 7.84-7.98 (m, 1H), 7.61-7.81 (m, 2H), 7.38-7.55 (m, 2H), 7.15-7.35 (m, 1H), 6.58-6.76 (m, 1H), 3.77-4.47 (m, 5H), 3.72 (d, J=6.7 Hz, 4H), 2.59-2.80 (m, 2H), 2.36-2.56 (m, 2H), 2.22-2.34 (m, 2H), 2.08-2.20 (m, 1H), 1.89-2.05 (m, 1H), 1.13-1.34 (m, 1H). Two diastereomers were resolved by SFC (Column: OD (5 um), Mobile phase: Base-IPA in CO$_2$, Flow rate: 60 mL/min Wave length: 220 nm $t_{R1}$=3.754 min, $t_{R2}$=6.602) to give Example 23a (first peak) as an oil and Example 23b (second peak) as an oil.

EX-23a $^1$H NMR: (CD$_3$OD, 400 MHz): δ 8.12 (s, 1H), 7.97-8.08 (m, 1H), 7.61-7.78 (m, 2H), 7.36-7.47 (m, 3H), 7.30 (t, J=8.2 Hz, 1H), 6.72 (d, J=8.6 Hz, 1H), 6.58 (d, J=8.6 Hz, 1H), 4.23-4.41 (m, 1H), 4.14 (dd, J=13.1, 20.0 Hz, 1H), 3.85-4.00 (m, 2H), 3.67-3.80 (m, 4H), 3.54 (t, J=8.7 Hz, 1H), 2.58-2.74 (m, 2H), 2.39-2.57 (m, 2H), 2.04-2.24 (m, 3H), 1.86-2.02 (m, 1H), 1.58-1.73 (m, 1H), 1.47 (br. s., 1H), 0.96-1.19 (m, 1H). MS (ESI) m/z 622.2 (M+H).

EX-23b $^1$H NMR: (CD$_3$OD, 400 MHz): δ 8.19 (s, 1H), 8.08 (br. s., 1H), 7.95 (t, J=7.7 Hz, 1H), 7.65-7.80 (m, 2H), 7.38-7.50 (m, 2H), 7.21-7.35 (m, 1H), 6.72 (d, J=8.6 Hz, 1H), 6.63 (d, J=8.6 Hz, 1H), 4.26-4.48 (m, 1H), 4.08-4.24 (m, 1H), 3.90-4.03 (m, 2H), 3.68-3.82 (m, 4H), 3.62 (d, J=12.1 Hz, 1H), 3.32-3.40 (m, 1H), 3.15-3.23 (m, 1H), 2.64-2.78 (m, 2H), 2.34-2.55 (m, 1H), 2.09-2.32 (m, 3H), 1.99 (br. s., 1H), 1.49-1.71 (m, 1H), 1.07-1.38 (m, 2H). MS (ESI) m/z 622.2 (M+H).

By using procedures similar to those described above, the following compounds were synthesized and characterized

| Example | Structure | LCMS [M + 1] | Hu FXIa Ki (nM) |
|---|---|---|---|
| 23a | methyl ((S)-9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,6)-pyridina-2(1,2)-benzenacyclononaphane-2$^4$-yl)carbamate | 622 | >875 |
| 23b | methyl ((R)-9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,6)-pyridina-2(1,2)-benzenacyclononaphane-2$^4$-yl)carbamate | 622 | 44.2 |

| Example | Structure | LCMS [M + 1] | Hu FXIa Ki (nM) |
|---|---|---|---|
| 24 | 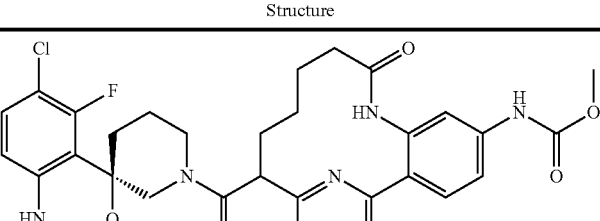 methyl (9-((R)-6-chloro-5-fluoro-2-oxo-1,2-dihydrospiro[benzo[d][1,3]oxazine-4,3'-piperidine]-1'-carbonyl)-4-oxo-3-aza-1(2,6)-pyridina-2(1,2)-benzenacyclononaphane-2⁴-yl)carbamate | 636 | >875 |

Example 25

Methyl (9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,4)-pyridina-2(1,2)-benzenacyclononaphane-2⁴-yl)carbamate (EX-25)

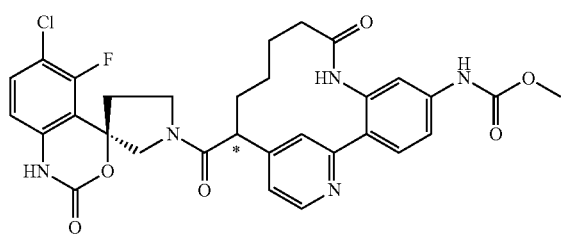
EX-25a and 25b

Synthetic Scheme for Example 25

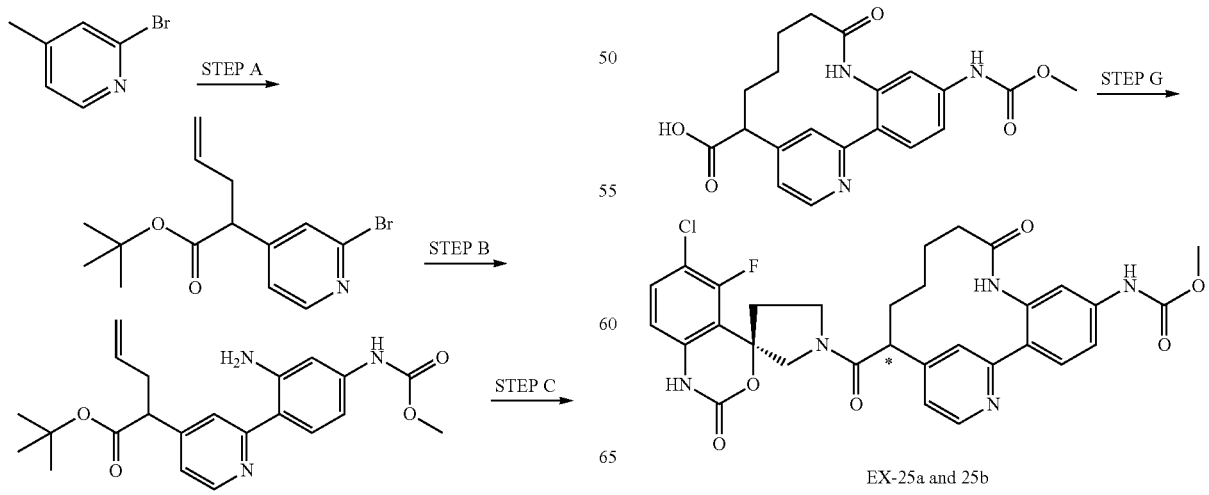

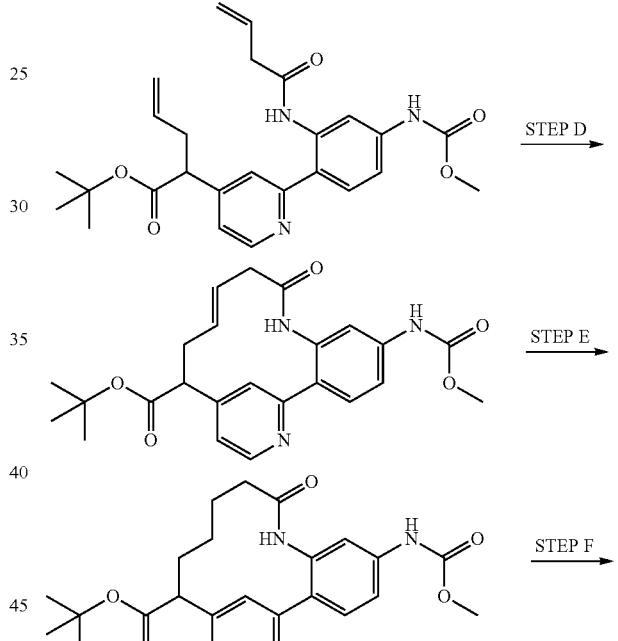

EX-25a and 25b

Step A: tert-Butyl 2-(2-bromopyridin-4-yl)pent-4-enoate

To a solution of 2-bromo-6-methylpyridine (1.72 g, 10.00 mmol) in THF (25 mL) was added LDA (12.5 mL, 25 mmol, 2M in THF) at −78° C. under $N_2$ protection. The mixture was stirred at −78° C. for 3 h. Then $(BOC)_2O$ (2.321 mL, 10.00 mmol) was added and the reaction was stirred at −78° C. for 2 h. Then 3-bromoprop-1-ene (1.814 g, 15.00 mmol) was added to the reaction mixture at −78° C. and stirred at 25° C. for 16 h. The reaction mixture was quenched with aq. sat. $NH_4Cl$ (100 mL) and extracted with EtOAc (100 mL). The organic layer was dried over $Na_2SO_4$, filtered and concentrated. The residue was purified by prep-HPLC to give the title compound. LC/MS (ESI) m/z 312.1 & 314.1 (M+H)

Step B: tert-Butyl 2-(2-(2-amino-4-((methoxycarbonyl)amino)phenyl)pyridin-4-yl)pent-4-enoate A mixture of tert-butyl 2-(2-bromopyridin-4-yl)pent-4-enoate (1 g, 3.20 mmol), methyl (3-amino-4-(4,4,5,5-tetramethyl-1,3,2-dioxaborolan-2-yl)phenyl)carbamate (0.936 g, 3.20 mmol), $PdCl_2(dppf)$ (100 mg, 0.137 mmol) and $K_3PO_4$ (1.5 g, 7.07 mmol) in dioxane (75 mL) and water (15 mL) was stirred at 100° C. for 16 h under $N_2$ atmospere. After cooling to RT, the mixture was filtered through a thin pad of celite and the filtrate was concentrated to give the crude product as an oil. The crude product was purified by flash column chromatography on silica gel (0-30% EtOAc/PE) to give the title compound. MS (ESI) m/z 398.3 (M+H)

$^1H$ NMR ($CDCl_3$, 400 MHz): δ 8.50 (d, J=5.5 Hz, 1H), 7.54 (s, 1H), 7.46 (d, J=8.5 Hz, 1H), 7.07-7.11 (m, 1H), 6.99 (br. s., 1H), 6.66 (dd, J=2.0, 8.5 Hz, 1H), 6.60 (br. s., 1H), 5.94 (br. s., 2H), 5.73 (tdd, J=6.7, 10.3, 17.1 Hz, 1H), 5.01-5.13 (m, 2H), 3.76-3.81 (m, 4H), 3.56 (t, J=7.8 Hz, 1H), 2.72-2.87 (m, 1H), 2.49 (td, J=7.0, 14.1 Hz, 1H), 1.42 (s, 9H).

Step C: tert-Butyl 2-(2-(2-(but-3-enamido)-4-((methoxycarbonyl)amino)phenyl)pyridin-4-yl)pent-4-enoate To a solution of tert-butyl 2-(2-(2-amino-4-((methoxycarbonyl)amino)phenyl)pyridin-4-yl)pent-4-enoate (200 mg, 0.503 mmol), but-3-enoic acid (43.3 mg, 0.503 mmol) in EtOAc (10 mL) was added DIPEA (0.264 mL, 1.510 mmol). The mixture was cooled to −78° C. under $N_2$ and then T3P (640 mg, 1.006 mmol, 50% in EtOAc) was added and the resulting mixture was stirred at −78° C. for 3 h. Solvent was then evaporated under reduced pressure to give the crude product as an oil. The crude product was purified by flash column chromatography on silica gel (0-20% EtOAc/PE) to give the title compound. MS (ESI) m/z 466.1 (M+1)

$^1H$ NMR ($CDCl_3$, 400 MHz): δ 8.48 (d, J=5.1 Hz, 1H), 8.38 (s, 1H), 7.65 (d, J=11.5 Hz, 2H), 7.45 (br. s., 1H), 7.19 (d, J=4.3 Hz, 1H), 5.97-6.11 (m, 1H), 5.66-5.82 (m, 1H), 5.26-5.36 (m, 2H), 5.02-5.16 (m, 2H), 3.78 (s, 3H), 3.56-3.66 (m, 1H), 3.22 (d, J=7.2 Hz, 2H), 2.75-2.88 (m, 1H), 2.45-2.57 (m, 1H), 1.43 (s, 9H).

Step D: tert-Butyl (E)-$2^4$-((methoxycarbonyl)amino)-4-oxo-3-aza-1(2,4)-pyridina-2(1,2)-benzenacyclononaphan-6-ene-9-carboxylate A mixture of tert-butyl 2-(2-(2-(but-3-enamido)-4-((methoxycarbonyl)amino)phenyl)pyridin-4-yl)pent-4-enoate (300 mg, 0.644 mmol) and p-TSA (135 mg, 0.784 mmol) in DCM (340 mL) was degassed with $N_2$ for 30 min and then refluxed for one hour. Then a solution of Grubbs II catalyst (300 mg, 0.353 mmol) in DCM (10 mL) was added dropwise to the reaction mixture and the reaction mixture was stirred at 40° C. for 24 h. LCMS showed the starting material was almost completely consumed. The mixture was washed with aqueous $NaHCO_3$ (200 mL) and the aqueous layer was extracted with DCM (2×200 mL). The combined organic fractions were washed with brine (300 mL), dried ($Na_2SO_4$), filtered and concentrated. The residue was purified by prep-TLC ($SiO_2$, PE:EtOAc=1:7) to give the title compound. LC/MS (ESI) m/z 438.1 (M+1).

$^1H$ NMR (400 MHz, DMSO-$d_6$): 12.46 (br. s., 1H), 8.24 (s, 1H), 7.96 (d, J=8.5 Hz, 1H), 7.25-7.56 (m, 2H), 6.87 (s, 1H).

Step E: tert-Butyl $2^4$-((methoxycarbonyl)amino)-4-oxo-3-aza-1(2,4)-pyridina-2(1,2)-benzenacyclononaphane-9-carboxylate A suspension of tert-butyl (E)-$2^4$-((methoxycarbonyl)amino)-4-oxo-3-aza-1(2,4)-pyridina-2(1,2)-benzenacyclononaphan-6-ene-9-carboxylate (100 mg, 0.229 mmol) and palladium on carbon (24.33 mg, 0.023 mmol) in MeOH (5 mL) was stirred under $H_2$ atmosphere (15 psi) at 25° C. for 5 hrs. LCMS showed the reactant was consumed. The mixture was filtered through a thin pad of celite and the filtrate was concentrated to give the title compound, which was used in the next step without further purification. LC/MS (ESI) m/z 440.3 (M+1).

Step F: $2^4$-((Methoxycarbonyl)amino)-4-oxo-3-aza-1(2,4)-pyridina-2(1,2)-benzenacyclononaphane-9-carboxylic Acid A solution of tert-butyl $2^4$-((methoxycarbonyl)amino)-4-oxo-3-aza-1(2,4)-pyridina-2(1,2)-benzenacyclononaphane-9-carboxylate (90 mg, 0.205 mmol) in HCl/dioxane (5 mL, 4M) was stirred at 25° C. for 12 hrs. The reaction mixture was concentrated to give the crude product as a solid. The crude product was suspended in $CH_3CN$ and filtered to give the title compound. LC/MS (ESI) m/z 384.0 (M+1).

Step G: Methyl (9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,4)-pyridina-2(1,2)-benzenacyclononaphane-$2^4$-yl)carbamate (EX-25)

To a solution of $2^4$-((methoxycarbonyl)amino)-4-oxo-3-aza-1(2,4)-pyridina-2(1,2)-benzenacyclononaphane-9-carboxylic acid (5 mg, 0.196 mmol) in DMF (2 mL) was added HATU (74.4 mg, 0.196 mmol), (R)-6-chloro-5-fluorospiro[benzo[d][1,3]oxazine-4,3'-pyrrolidin]-2(1H)-one hydrochloride (57.3 mg, 0.196 mmol) and DIPEA (0.068 mL, 0.391 mmol). The mixture was then stirred at 25° C. for 5 h. LCMS showed the reactant was consumed. The mixture was diluted with DMF (2 mL) and purified by prep-HPLC to give the title compound. MS (ESI) m/z 622.1 (M+1).

Two diastereomers were resolved by SFC (Column: OD, 10 um), Mobile phase: 50% EtOH, Flow rate: 80 mL/min Wavelength: 220 nm) to give Example 25a (fast-eluting isomer) as a solid and Example 25b (slow-eluting isomer).

EX-25a $^1H$ NMR: ($CD_3OD$, 400 MHz): δ 8.56 (dd, J=5.3, 9.7 Hz, 1H), 7.74-7.33 (m, 5H), 7.21 (dd, J=4.6, 13.2 Hz, 1H), 6.70 (dd, J=8.6, 18.7 Hz, 1H), 4.19 (d, J=12.6 Hz, 1H), 4.08-3.86 (m, 3H), 3.82-3.68 (m, 4H), 3.54-3.43 (m, 1H), 2.81-2.66 (m, 1H), 2.56-2.36 (m, 3H), 2.12-1.73 (m, 4H), 1.29 (br. s., 1H), 0.99-0.86 (m, 1H). LC/MS (ESI) m/z 622.2 (M+H).

EX-25b $^1H$ NMR: ($CD_3OD$, 400 MHz): δ 8.56 (dd, J=5.3, 11.9 Hz, 1H), 7.73-7.63 (m, 1H), 7.57 (s, 1H), 7.52-7.36 (m, 3H), 7.25 (dd, J=4.4, 13.2 Hz, 1H), 6.74 (d, J=8.6 Hz, 1H), 6.67 (d, J=8.6 Hz, 1H), 4.21-4.06 (m, 1H), 4.04-3.81 (m, 3H), 3.75 (d, J=4.6 Hz, 3H), 3.71-3.57 (m, 1H), 2.73-2.36 (m, 3H), 2.11-1.98 (m, 2H), 1.93-1.74 (m, 2H), 0.89 (d, J=7.5 Hz, 3H). MS (ESI) m/z 622.2 (M+1).

| Example | Structure | LCMS [M + 1] | Hu FXIa Ki (nM) |
|---|---|---|---|
| 25a | methyl ((R)-9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,4)-pyridina-2(1,2)-benzenacyclononaphane-2⁴-yl)carbamate | 622 | 1.30 |
| 25b | methyl ((S)-9-((R)-6-chloro-5-fluoro-2-oxo-1,2-dihydrospiro[benzo[d][1,3]oxazine-4,3'-pyrrolidine]-1'-carbonyl)-4-oxo-3-aza-1(2,4)-pyridina-2(1,2)-benzenacyclononaphane-2⁴-yl)carbamate | 622 | >875 |

Example 27

3-((R)-6-Chloro-5-fluoro-2-oxo-1,2-dihydrospiro[benzo[d][1,3]oxazine-4,3'-piperidine]-1'-carbonyl)-1¹,1²-dihydro-9-aza-1(6,7)-quinolina-2(4,2)-pyridinacyclononaphane-1²,8-dione (EX-27)

EX-27

Synthetic Scheme for Example 27

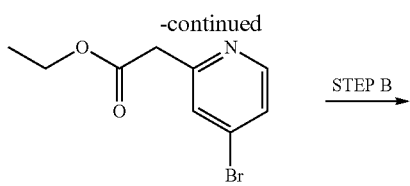

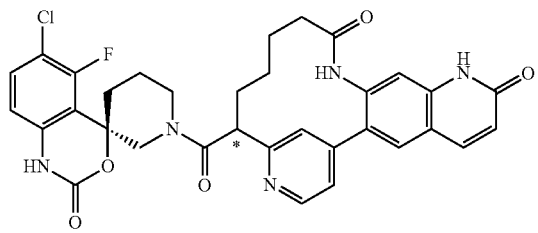 [SMILES: O=C1CCCCC(C(=O)N2CCC[C@@]3(C2)OC(=O)Nc2ccc(Cl)c(F)c23)c2cc(ccn2)-c2cc3ccc(=O)[nH]c3cc2N1]

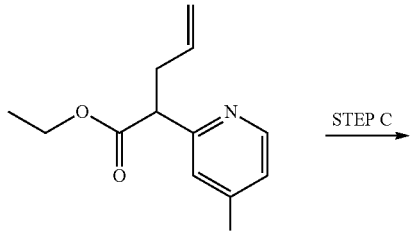

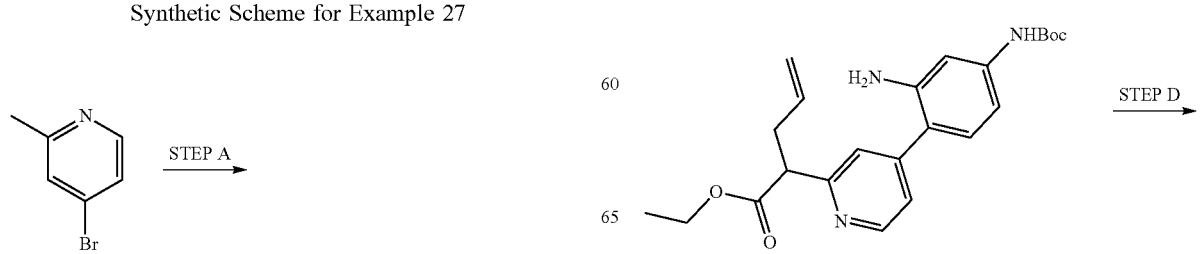

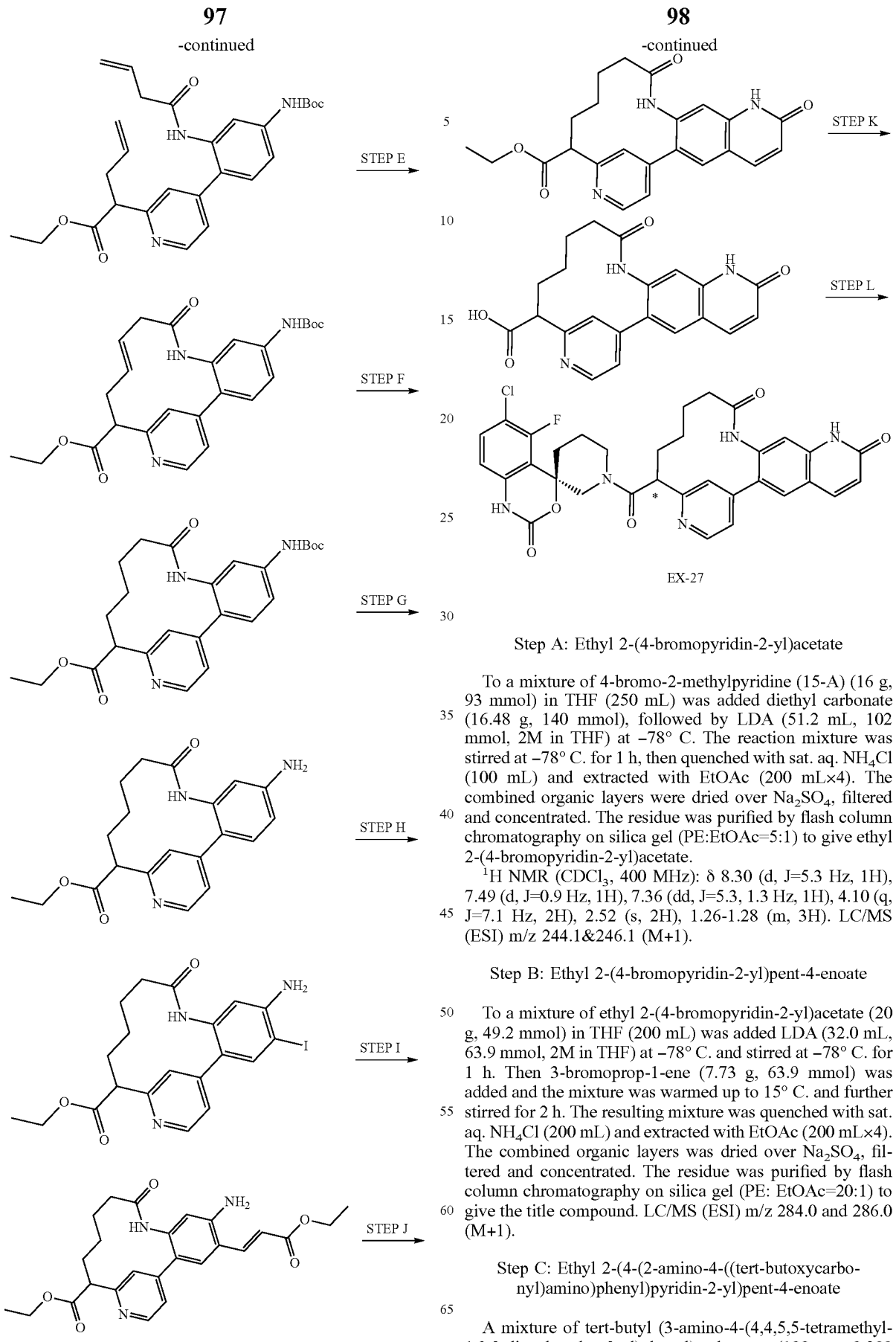

EX-27

Step A: Ethyl 2-(4-bromopyridin-2-yl)acetate

To a mixture of 4-bromo-2-methylpyridine (15-A) (16 g, 93 mmol) in THF (250 mL) was added diethyl carbonate (16.48 g, 140 mmol), followed by LDA (51.2 mL, 102 mmol, 2M in THF) at −78° C. The reaction mixture was stirred at −78° C. for 1 h, then quenched with sat. aq. NH$_4$Cl (100 mL) and extracted with EtOAc (200 mL×4). The combined organic layers were dried over Na$_2$SO$_4$, filtered and concentrated. The residue was purified by flash column chromatography on silica gel (PE:EtOAc=5:1) to give ethyl 2-(4-bromopyridin-2-yl)acetate.

$^1$H NMR (CDCl$_3$, 400 MHz): δ 8.30 (d, J=5.3 Hz, 1H), 7.49 (d, J=0.9 Hz, 1H), 7.36 (dd, J=5.3, 1.3 Hz, 1H), 4.10 (q, J=7.1 Hz, 2H), 2.52 (s, 2H), 1.26-1.28 (m, 3H). LC/MS (ESI) m/z 244.1&246.1 (M+1).

Step B: Ethyl 2-(4-bromopyridin-2-yl)pent-4-enoate

To a mixture of ethyl 2-(4-bromopyridin-2-yl)acetate (20 g, 49.2 mmol) in THF (200 mL) was added LDA (32.0 mL, 63.9 mmol, 2M in THF) at −78° C. and stirred at −78° C. for 1 h. Then 3-bromoprop-1-ene (7.73 g, 63.9 mmol) was added and the mixture was warmed up to 15° C. and further stirred for 2 h. The resulting mixture was quenched with sat. aq. NH$_4$Cl (200 mL) and extracted with EtOAc (200 mL×4). The combined organic layers was dried over Na$_2$SO$_4$, filtered and concentrated. The residue was purified by flash column chromatography on silica gel (PE: EtOAc=20:1) to give the title compound. LC/MS (ESI) m/z 284.0 and 286.0 (M+1).

Step C: Ethyl 2-(4-(2-amino-4-((tert-butoxycarbonyl)amino)phenyl)pyridin-2-yl)pent-4-enoate A mixture of tert-butyl (3-amino-4-(4,4,5,5-tetramethyl-1,3,2-dioxaborolan-2-yl)phenyl)carbamate (100 mg, 0.299 mmol), ethyl 2-(4-bromopyridin-2-yl)pent-4-enoate (111 mg, 0.389 mmol), $K_3PO_4$ (191 mg, 0.898 mmol) and 2nd generation x-phos precatalyst (30 mg, 0.038 mmol) in THF (3 mL) was stirred at 60° C. for 4 h under $N_2$. After cooling, the reaction mixture was diluted with water (10 mL) and extracted with EtOAc (20 mL×4). The combined organic layers were dried over $Na_2SO_4$, filtered and concentrated. The residue was purified by prep-TLC ($SiO_2$, PE:EtOAc=1:1) to give the title compound. LC/MS (ESI) m/z 412.2 (M+1).

Step D: Ethyl 2-(4-(2-(but-3-enamido)-4-((tert-butoxycarbonyl)amino)phenyl)pyridin-2-yl)pent-4-enoate To a solution of ethyl 2-(4-(2-amino-4-((tert-butoxycarbonyl)amino)phenyl)pyridin-2-yl)pent-4-enoate (60 mg, 0.146 mmol), but-3-enoic acid (18.83 mg, 0.219 mmol) in EtOAc (5 mL) was added DIPEA (0.127 mL, 0.729 mmol), T3P (186 mg, 0.292 mmol) at −78° C. Then the reaction mixture was warmed to 15° C. and stirred overnight for 18 h. The mixture was cooled, diluted with aqueous $NaHCO_3$ (10 mL) and extracted with EtOAc (2×20 mL). The combined organic fractions were washed with brine (20 mL), dried ($Na_2SO_4$), filtered and concentrated. The residue was purified by prep-TLC ($SiO_2$, PE:EtOAc=1:1) to give the title compound. MS (ESI) m/z 480.3 (M+1).

$^1$H NMR (CDCl$_3$, 400 MHz): δ 8.59 (d, J=4.9 Hz, 1H), 8.10 (br. s., 1H), 7.52 (d, J=7.1 Hz, 1H), 7.39 (br. s., 1H), 7.27-7.31 (m, 1H), 7.12-7.18 (m, 2H), 7.06 (br. s., 1H), 5.67-5.89 (m, 2H), 4.98-5.14 (m, 4H), 4.13-4.22 (m, 2H), 3.91 (t, J=7.6 Hz, 1H), 3.06 (d, J=7.1 Hz, 2H), 2.81-2.92 (m, 1H), 2.69 (dt, J=14.0, 6.9 Hz, 1H), 1.50 (s, 9H) 1.20 (br. s., 3H).

Step E: Ethyl (E)-2$^4$-((tert-butoxycarbonyl)amino)-4-oxo-3-aza-1(4,2)-pyridina-2(1,2)-benzenacyclononaphan-6-ene-9-carboxylate A mixture of ethyl-2-(4-(2-(but-3-enamido)-4-((tert-butoxycarbonyl)amino)phenyl)pyridin-2-yl)pent-4-enoate (20 mg, 0.042 mmol) and Zhan Catalyst-1B (20 mg, 0.027 mmol) in 1,2-dichloroethane (5 mL) was degassed by bubbling nitrogen for 15 min and stirred at 120° C. under nitrogen for 16 h. LCMS showed starting material was consumed completely. The mixture was cooled to RT and concentrated. The residue was diluted with EtOAc (20 mL), washed with aqueous $NaHCO_3$ (20 mL), brine (10 mL), dried over $Na_2SO_4$, filtered and concentrated. The residue was purified by flash silica gel chromatography (0~50% EtOAc/PE) to give the title compound. LC/MS (ESI) m/z 452.2 (M+1).

$^1$H NMR (CDCl$_3$, 400 MHz): δ 8.68 (d, J=4.9 Hz, 1H), 8.27 (br. s., 1H), 8.16 (s, 1H), 7.33 (d, J=8.4 Hz, 1H), 7.13-7.21 (m, 2H), 6.99 (s, 1H), 6.85 (s, 1H), 5.86-6.03 (m, 1H), 5.22-5.35 (m, 1H), 4.18-4.32 (m, 2H), 4.09 (br. s., 1H), 3.12 (d, J=7.7 Hz, 2H), 2.62-2.85 (m, 2H), 1.54 (s, 9H), 1.27 (s, 3H).

Step F: Ethyl 2$^4$-((tert-butoxycarbonyl)amino)-4-oxo-3-aza-1(4,2)-pyridina-2(1,2)-benzenacyclononaphane-9-carboxylate A mixture of ethyl (E)-2$^1$-((tert-butoxycarbonyl)amino)-4-oxo-3-aza-1(4,2)-pyridina-2(1,2)-benzenacyclononaphan-6-ene-9-carboxylate (10 mg, 0.022 mmol) and Pd—C(23.57 mg, 0.022 mmol, 10%) in MeOH (5 mL) was stirred under 15 psi of $H_2$ at 20° C. for 4 h. The mixture was filtered through Celite and washed with MeOH (60 mL). The combined filtrates were concentrated to give the title compound, which was used in the next step without further purification. LC/MS (ESI) m/z 454.1 (M+1).

$^1$H NMR (CDCl$_3$, 400 MHz): δ 8.64 (d, J=4.9 Hz, 1H), 7.46 (s, 1H), 7.37 (br. s., 1H), 7.31 (br. s., 1H), 7.16 (d, J=4.2 Hz, 1H), 7.09 (s, 1H), 6.99 (s, 1H), 6.77 (s, 1H), 4.13-4.27 (m, 2H), 3.85 (dd, J=11.5, 4.6 Hz, 1H), 2.26-2.36 (m, 2H), 1.91-2.16 (m, 4H), 1.58-1.72 (m, 2H), 1.52 (s, 9H), 1.23 (t, J=7.1 Hz, 3H).

Step G: Ethyl 2$^4$-amino-4-oxo-3-aza-1(4,2)-pyridina-2(1,2)-benzenacyclononaphane-9-carboxylate To a mixture of ethyl 2$^4$-((tert-butoxycarbonyl)amino)-4-oxo-3-aza-1(4,2)-pyridina-2(1,2)-benzenacyclononaphane-9-carboxylate (10 mg, 0.021 mmol) in DCM (1.5 mL) was added TFA (0.3 mL, 3.89 mmol) and the reaction mixture was stirred at 20° C. for 1 h. The reaction mixture was evaporated under reduced pressure to give the title compound, which was used for the next step without further purification. MS (ESI) m/z 354.1 (M+1).

$^1$H NMR (CDCl$_3$, 400 MHz): δ 8.62 (d, J=4.9 Hz, 1H), 7.36 (s, 1H), 7.25 (s, 1H), 7.16 (d, J=4.4 Hz, 1H), 6.86 (s, 1H), 6.74 (s, 1H), 6.64-6.70 (m, 1H), 4.12-4.28 (m, 2H), 3.86 (dd, J=11.1, 4.3 Hz, 1H), 2.23-2.40 (m, 2H), 1.86-2.19 (m, 3H), 1.67 (d, J=11.7 Hz, 1H), 1.24 (d, J=7.3 Hz, 3H).

Step H: Ethyl 2$^4$-amino-2$^5$-iodo-4-oxo-3-aza-1(4,2)-pyridina-2(1,2)-benzenacyclononaphane-9-carboxylate A mixture of ethyl 2$^4$-amino-4-oxo-3-aza-1(4,2)-pyridina-2(1,2)-benzenacyclononaphane-9-carboxylate (400 mg, 1.132 mmol) in MeOH (1 mL) was added a solution of ICl (0.085 mL, 1.698 mmol) in DCM (0.5 mL) and the reaction mixture was stirred at 20° C. for 1 h. The mixture was evaporated under reduced pressure. The residue was diluted with sat. aq. $NaHCO_3$ (3 mL) and extracted with DCM: MeOH (10:1) (5 mL×4). The combined organic layers were dried over $Na_2SO_4$, filtered and concentrated to give the title comopund, which was used in the next step without further purification. MS (ESI) m/z 480.1 (M+1).

$^1$H NMR (CDCl$_3$, 400 MHz): δ 8.47 (d, J=5.3 Hz, 1H), 7.82 (s, 1H), 7.47 (s, 1H), 7.28 (d, J=4.0 Hz, 1H), 6.64 (s, 1H), 4.11-4.24 (m, 2H), 3.93 (dd, J=11.7, 5.1 Hz, 1H), 2.36-2.45 (m, 1H), 1.90-2.09 (m, 4H), 1.69-1.82 (m, 1H), 1.51-1.64 (m, 1H), 1.20-1.26 (m, 3H), 0.70 (d, J=10.8 Hz, 1H).

Step I: Ethyl (E)-2$^4$-amino-2$^5$-(3-ethoxy-3-oxoprop-1-en-1-yl)-4-oxo-3-aza-1(4,2)-pyridina-2(1,2)-benzenacyclononaphane-9-carboxylate To a mixture of ethyl 2$^4$-amino-2$^5$-iodo-4-oxo-3-aza-1(4,2)-pyridina-2(1,2)-benzenacyclononaphane-9-carboxylate (60 mg, 0.125 mmol) in DMF (1.0 mL) was added $K_2CO_3$ (17.30 mg, 0.125 mmol), (E)-ethyl3-(4,4,5,5-tetramethyl-1,3,2-dioxaborolan-2-yl)acrylate (28.3 mg, 0.125 mmol), PdCl$_2$(dppf) (92 mg, 0.125 mmol). The mixture was then stirred at 80° C. for 12 h under $N_2$. The reaction mixture was concentrated and the residue was purified by prep-TLC ($SiO_2$, DCM:MeOH=8:1) to give the title compound. LC/MS (ESI) m/z 452.2 (M+1).

Step J: Ethyl 1²,8-dioxo-1¹,1²-dihydro-9-aza-1(6,7)-quinolina-2(4,2)-pyridinacyclononaphane-3-carboxylate A mixture of ethyl (E)-2⁴-amino-2⁵-(3-ethoxy-3-oxo-prop-1-en-1-yl)-4-oxo-3-aza-1(4,2)-pyridina-2(1,2)-benzenacyclononaphane-9-carboxylate (120 mg, 0.186 mmol) in CH₃CN (10 mL) was stirred at 70° C. for 10 h under N₂ and simultaneously irradiated with a high pressure mercury lamp. The reaction mixture was concentrated and the residue was purified by prep-TLC (SiO₂, EtOAc:MeOH=8:1) to give the title compound. LC/MS (ESI) m/z 406.2 (M+1).

Step K: 1²,8-Dioxo-1¹,1²-dihydro-9-aza-1(6,7)-quinolina-2(4,2)-pyridinacyclononaphane-3-carboxylic Acid To a mixture of ethyl 1²,8-dioxo-1¹,1²-dihydro-9-aza-1(6,7)-quinolina-2(4,2)-pyridinacyclononaphane-3-carboxylate (50 mg, 0.123 mmol) in MeOH (3 mL) and water (1 mL) was added NaOH (19.73 mg, 0.493 mmol) and the mixture was stirred at 60° C. for 4 h under N₂. The reaction mixture was concentrated. The residue was diluted with water (2.0 mL), acidified by HCl to pH 4-5, and purified by prep-HPLC to give the title compound. LC/MS (ESI) m/z 378.2 (M+H).

Step L: 3-((R)-6-Chloro-5-fluoro-2-oxo-1,2-dihydrospiro[benzo[d][1,3]oxazine-4,3'-piperidine]-1'-carbonyl)-1¹,1²-dihydro-9-aza-1(6,7)-quinolina-2(4,2)-pyridinacyclononaphane-1²,8-dione (EX-27)

To a mixture of 1²,8-dioxo-1¹,1²-dihydro-9-aza-1(6,7)-quinolina-2(4,2)-pyridinacyclononaphane-3-carboxylic acid (30 mg, 0.079 mmol) in DMF (1 mL) was added (R)-6-chloro-5-fluorospiro[benzo[d][1,3]oxazine-4,3'-piperidin]-2(1H)-one hydrochloride (29.3 mg, 0.095 mmol), HATU (39.3 mg, 0.103 mmol) and DIPEA (0.042 mL, 0.238 mmol) at 0° C., then the mixture was stirred at 20° C. for 3 h under N₂. The reaction mixture was directly purified by prep-HPLC to give Example 27. MS (ESI) m/z 630.2 (M+1).

¹H NMR (400 MHz, CD₃OD): 8.71-8.88 (m, 1H), 7.87-8.36 (m, 4H), 7.36-7.48 (m, 1H), 7.18-7.28 (m, 1H), 6.55-6.80 (m, 2H), 4.48-4.79 (m, 2H), 4.14-4.34 (m, 1H), 3.33-3.49 (m, 1H), 2.71-3.05 (m, 1H), 2.42-2.61 (m, 2H), 1.64-2.25 (m, 8H), 1.38 (d, J=10.6 Hz, 1H), 0.68 (d, J=10.1 Hz, 1H).

By using procedures similar to those described above, the following compounds were synthesized and characterized.

| Example | Structure | LCMS [M + 1] | Hu FXIa Ki (nM) |
| --- | --- | --- | --- |
| 26 (mixture of two diastereomers) 3-((R)-6-chloro-5-fluoro-2-oxo-1,2-dihydrospiro[benzo[d][1,3]oxazine-4,3'-pyrrolidine]-1'-carbonyl)-1¹,1²-dihydro-9-aza-1(6,7)-quinolina-2(4,2)-pyridinacyclononaphane-1²,8-dione | | 616 | 3.93 |
| 27 (mixture of two diastereomers) 3-((R)-6-chloro-5-fluoro-2-oxo-1,2-dihydrospiro[benzo[d][1,3]oxazine-4,3'-piperidine]-1'-carbonyl)-1¹,1²-dihydro-9-aza-1(6,7)-quinolina-2(4,2)-pyridinacyclononaphane-1²,8-dione | | 630 | 12.99 |

Example 28
Methyl (9-((R)-6-chloro-2-oxo-1,2-dihydrospiro[benzo[d][1,3]oxazine-4,3'-pyrrolidine]-1'-carbonyl)-1⁵-fluoro-4-oxo-3-aza-1(1,3),2(1,2)-dibenzenacyclononaphane-2⁴-yl)carbamate (EX-28)
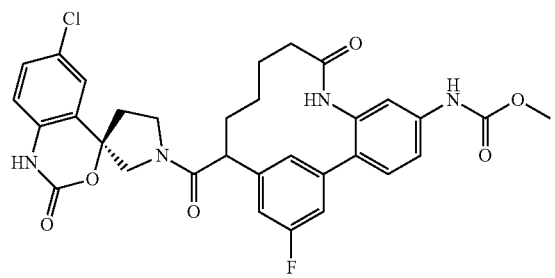 [SMILES: COC(=O)Nc1ccc2c(c1)NC(=O)CCCCC(C(=O)N1CC[C@@]3(C1)OC(=O)Nc1ccc(Cl)cc13)c1cc(F)cc-2c1]
Synthetic Scheme for Example 28
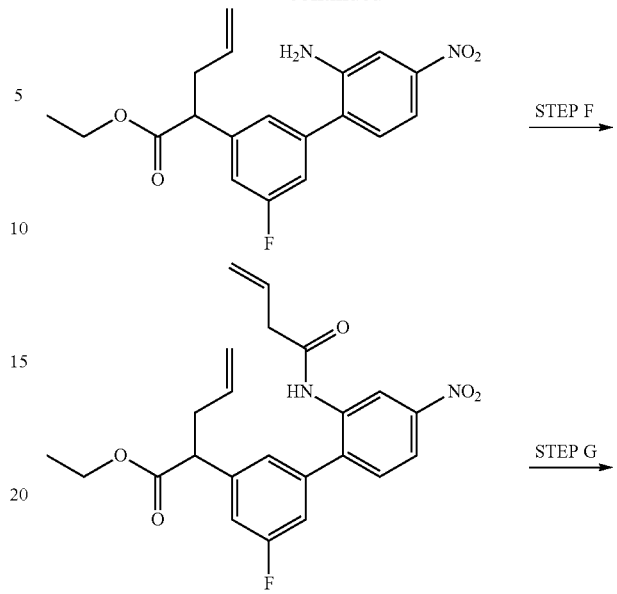
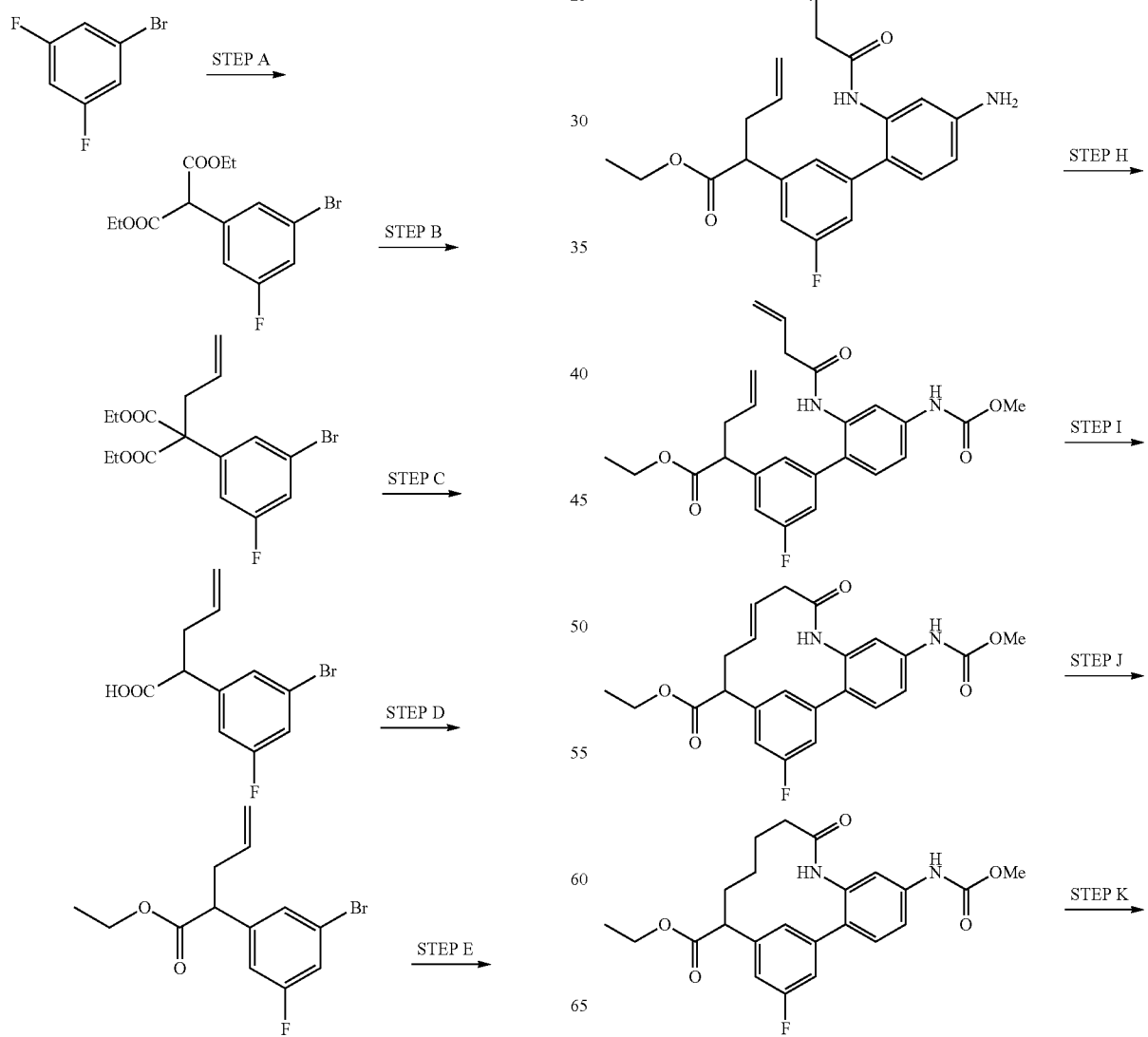

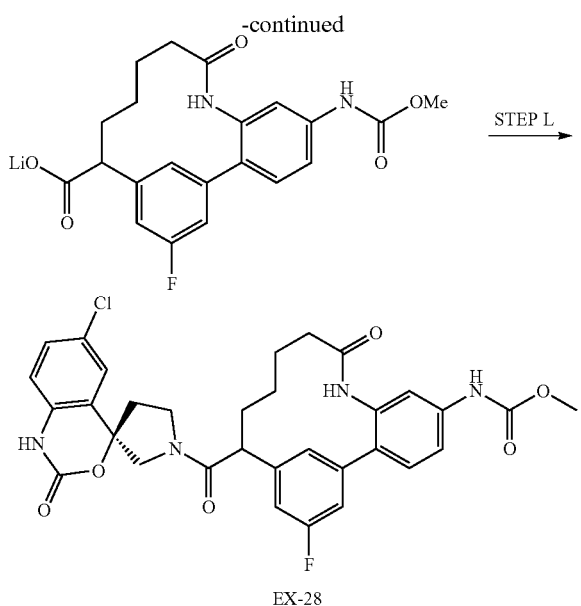

EX-28

Step A: Diethyl 2-(3-bromo-5-fluorophenyl)malonate

To a stirred solution of NaH (60%, 2.072 g, 51.8 mmol) in NMP (100 ml) was dropwise added diethyl malonate (7.83 ml, 51.8 mmol) at RT under nitrogen and stirred for 15 min. Then 1-bromo-3,5-difluorobenzene (10.0 g, 51.8 mmol) was added, the reaction vessel was caped and heated to 115° C. for 18 hrs. The reaction mixture was cooled to 5° C., then added to cold water (500 ml), and stirred for 5 min. The aqueous mixture was acidified with 1 N HCl to pH 3, then extracted with MTBE (3×200 ml). The combined organics washed with water (4×100 ml), brine 100 ml), dried over sodium sulphate, filtered and evaporated under reduced pressure. The residue was purified by flash column chromatography on silica gel (0-5% EtOAc/hexanes) to give diethyl 2-(3-bromo-5-fluorophenyl)malonate. $^1$H NMR (400 MHz, CDCl$_3$): 7.34 (s, 1H), 7.22 (m, 1H), 7.12 (m, 1H), 5.29 (s, 1H), 4.23 (m, 4H), 1.27 (t, 6H).

Step B: Diethyl 2-allyl-2-(3-bromo-5-fluorophenyl)malonate

To a stirred solution of diethyl 2-(3-bromo-5-fluorophenyl)malonate (3.87 g, 11.62 mmol) in ethanol (10 ml) was added NaOEt (0.790 g, 11.62 mmol), allyl bromide (1.005 ml, 11.62 mmol) at room temperature under nitrogen atmosphere. The resulting mixture was stirred at reflux for 4 h. The reaction mixture was evaporated under reduced pressure and diluted with water (100 ml), acidified with 2 N HCl to pH 3, then extracted with EtOAc (2×100 ml). The combined organics dried over sodium sulphate, filtered and concentrated. The residue was purified by flash column chromatography on silica gel (0-3% EtOAc/hexanes) to give the title compound. LC/MS=375 [M+2]

Step C: 2-(3-Bromo-5-fluorophenyl)pent-4-enoic Acid

To a stirred solution of diethyl 2-allyl-2-(3-bromo-5-fluorophenyl)malonate (3.28 g, 8.79 mmol) in EtOH (10 ml)/water (20 ml) was added NaOH (0.808 g, 20.21 mmol) at RT. The resulting mixture was refluxed for 3 hrs. The reaction mixture was evaporated under reduced pressure, then diluted with water (100 ml), acidified with 2 N HCl to pH 2, extracted with EtOAc (3×75 ml). The combined organics washed with brine (70 ml), dried over sodium sulphate, filtered, concentrated to dryness to obtain the title compound. LC/MS=274 [M+1]

Step D: Ethyl 2-(3-bromo-5-fluorophenyl)pent-4-enoate

To a stirred solution of 2-(3-bromo-5-fluorophenyl)pent-4-enoic acid (3.36 g, 12.30 mmol) in DCM (40 ml) was added DMF (0.047 ml), oxalyl chloride (1.185 ml, 13.53 mmol) at 0° C. under nitrogen. The resulting mixture was stirred at 0° C. to RT for 2 hrs. Then, quenched with EtOH (21.55 ml, 369 mmol) at RT and stirred for 10 min. The reaction mixture was concentrated. The residue was purified by flash column chromatography on silica gel (0-3% EtOAc/hexanes) to give the title compound. LC/MS=303 [M+2]

Step E: Ethyl 2-(2'-amino-5-fluoro-4'-nitro-[1,1'-biphenyl]-3-yl)pent-4-enoate Ethyl 2-(3-bromo-5-fluorophenyl)pent-4-enoate (2.00 g, 6.64 mmol), 5-nitro-2-(4,4,5,5-tetramethyl-1,3,2-dioxaborolan-2-yl)aniline (2.63 g, 9.96 mmol), K$_3$PO$_4$ (2.82 g, 13.28 mmol) were mixed in a pressure tube and added 1,4-dioxane (36 ml)/water (4.00 ml) (degassed with N$_2$ for 10 min) followed by tetrakis(triphenylphosphine)palladium(0) (1.535 g, 1.328 mmol). The reactione mixture was again degassed with N$_2$ for 5 min. The vial was caped and heated at 85° C. for 3 hrs. The mixture was cooled and the solvent was evaporated under reduced pressure. The residue was purified by flash column chromatography on silica gel (0-10% EtOAc/hexanes) to give the title compound. LC/MS=359.4 [M+1]

Step F: Ehyl 2-(2'-(but-3-enamido)-5-fluoro-4'-nitro-[1,1'-biphenyl]-3-yl)pent-4-enoate To a stirred solution of ethyl 2-(2'-amino-5-fluoro-4'-nitro-[1,1'-biphenyl]-3-yl)pent-4-enoate (722 mg, 2.015 mmol) in DMF (14 ml) was added vinylacetic acid (260 mg, 3.02 mmol), DIPEA (0.880 ml, 5.04 mmol), T3P (2.399 ml, 4.03 mmol) at 0° C. under nitrogen. The resulting mixture was stirred at 0° C. to RT for 18 hrs. The reaction mixture was diluted EtOAc (100 ml), washed with water (2×50 ml), brine (50 ml) and dried over sodium sulphate, filtered and concentrated. The residue was purified by flash column chromatography on silica gel (0-15% EtOAc/hexanes) to give the title compound. LC/MS=427 [M+1]

Step G: Ethyl 2-(4'-amino-2'-(but-3-enamido)-5-fluoro-[1,1'-biphenyl]-3-yl)pent-4-enoate To a stirred solution of ethyl 2-(2'-(but-3-enamido)-5-fluoro-4'-nitro-[1,1'-biphenyl]-3-yl)pent-4-enoate (634 mg, 1.487 mmol) in EtOH (10.6 ml)/water (2.65 ml) was added iron (913 mg, 16.35 mmol), NH$_4$Cl (795 mg, 14.87 mmol) at RT. The resulting mixture was stirred at 60° C. for 1 h. The reaction mixture was filtered through a pad of Celite and the filtrate was evaporated. The residue was basified with sat. NaHCO$_3$ (50 ml), extracted with EtOAc (2×100 ml). The combined organics washed with brine and dried over sodium sulphate, filtered and concentrated to obtain the title compound. LC/MS=397 [M+1]

Step H: Ethyl 2-(2'-(but-3-enamido)-5-fluoro-4'-((methoxycarbonyl)amino)-[1,1'-biphenyl]-3-yl)pent-4-enoate To a stirred solution of ethyl 2-(4'-amino-2'-(but-3-enamido)-5-fluoro-[1,1'-biphenyl]-3-yl)pent-4-enoate (576 mg, 1.453 mmol) in 1,4-dioxane (10.5 ml)/water (2.63 ml) was added NaHCO₃ (183 mg, 2.179 mmol), methyl chloroformate (0.225 ml, 2.91 mmol) at 0° C. under nitrogen. The resulting mixture was stirred at 0° C. to RT for 2 hrs. The reaction mixture was diluted with water (50 ml), extracted with EtOAc (2×80 ml). The combined organics washed with brine, dried over Na₂SO₄, filtered and concentrated undere reduced pressure. The residue was purified by flash column chromatography on silica gel (0-20% EtOAc/hexanes) to give the title compound. LC/MS=455 [M+1]

Step I: Ethyl (E)-1⁵-fluoro-2⁴-((methoxycarbonyl)amino)-4-oxo-3-aza-1(1,3),2(1,2)-dibenzenacyclononaphan-6-ene-9-carboxylate Ethyl 2-(2'-(but-3-enamido)-5-fluoro-4'-((methoxycarbonyl)amino)[1,1'-biphenyl]-3-yl)pent-4-enoate (556 mg, 1.223 mmol) was dissolved in toluene (102 ml) and degassed with N₂ (5 min), then Zhan Catalyst-1B (117 mg, 0.159 mmol) was added. The reaction mixture was caped and heated to 50° C. for 21 hrs. After cooling down to RT, the reaction mixture was evaporated and the residue was purified by flash column chromatography on silica gel (0-50% EtOAc/hexanes) to give the title compound. LC/MS=427.4 [M+1]

Step J: Ethyl 15-fluoro-2⁴-((methoxycarbonyl)amino)-4-oxo-3-aza-1(1,3),2(1,2)-dibenzenacyclononaphane-9-carboxylate To a stirred solution of ethyl (E)-1⁵-fluoro-2⁴-((methoxycarbonyl)amino)-4-oxo-3-aza-1(1,3),2(1,2)-dibenzenacyclononaphan-6-ene-9-carboxylate (374 mg, 0.877 mmol) in EtOAc (22.0 ml) MeOH (22.0 ml) was added Pd/C (10%, 280 mg, 0.263 mmol) at RT under nitrogen. Then, N₂ was replaced by H₂ balloon and the resulting mixture was stirred at RT for 16 hrs. The reaction mixture was filtered through a syringe filter and the filtrate was evaporated under reduced pressure. The residue was purified by flash column chromatography on silica gel (0-50% EtOAc/DCM) to give the title compound. LC/MS=429.4 [M+1]

Step K: Lithium 1⁵-fluoro-2⁴-((methoxycarbonyl)amino)-4-oxo-3-aza-1(1,3),2(1,2)-dibenzenacyclononaphane-9-carboxylate To a stirred solution of ethyl 15-fluoro-2⁴-((methoxycarbonyl)amino)-4-oxo-3-aza-1(1,3),2(1,2)-dibenzenacyclononaphane-9-carboxylate (82.0 mg, 0.191 mmol) in MeOH (0.5 ml)/THF (0.500 ml)/water (0.500 ml) was added LiOH.H₂O (8.83 mg, 0.211 mmol) at RT. The resulting mixture was stirred at RT for 4 hrs. The reaction mixture was concentrated and azeotroped with toluene thrice. This crude was used directly without further purification. LC/MS=401.1 [M-5]

Step L: Methyl (9-((R)-6-chloro-2-oxo-1,2-dihydrospiro[benzo[d][1,3]oxazine-4,3'-pyrrolidine]-1'-carbonyl)-1⁵-fluoro-4-oxo-3-aza-1(1,3),2(1,2)-dibenzenacyclononaphane-2⁴-yl)carbamate (EX-28)

To a stirred solution of lithium 1⁵-fluoro-2⁴-((methoxycarbonyl)amino)-4-oxo-3-aza-1(1,3),2(1,2)-dibenzenacyclononaphane-9-carboxylate (78.0 mg, 0.192 mmol) in DMF (1.24 ml) was added (R)-6-chlorospiro[benzo[d][1,3]oxazine-4,3'-pyrrolidin]-2(1H)-one hydrochloride (79 mg, 0.288 mmol), HATU (109 mg, 0.288 mmol), DIPEA (0.101 ml, 0.576 mmol) at RT under nitrogen. The resulting mixture was stirred at RT for 16 hrs. The reaction mixture was diluted with EtOAc (75 ml), washed with sat. NaHCO₃ (2×20 ml), brine (30 ml), dried over sodium sulphate, filtered and evaporated. The crude product was purified by Reverse Phase-HPLC (C18, 0-60% Acetonitrile/Water) to give the title compound. LC/MS=621.0 [M+1]

By using procedures similar to those described above, the following compounds were synthesized and characterized. Chiral columns for Examples 29/30.

| Example | Structure | LCMS [M + 1] | Hu FXIa Ki (nM) |
|---|---|---|---|
| 28 | 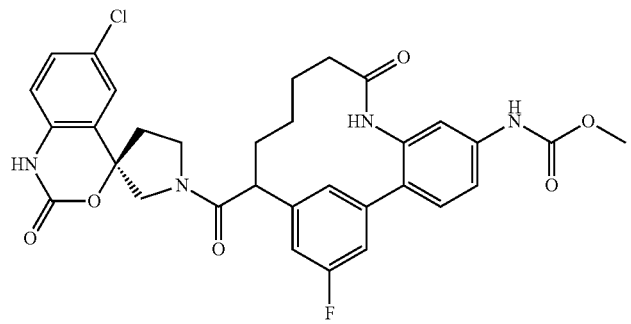 [SMILES: COC(=O)Nc1ccc2c(c1)NC(=O)CCCCC(C(=O)N1CC[C@@]3(C1)OC(=O)Nc1ccc(Cl)cc13)c1cc(F)cc-2c1] | 621 | 45.2 | methyl (9-((R)-6-chloro-2-oxo-1,2-dihydrospiro[benzo[d][1,3]oxazine-4,3'-pyrrolidine]-1'-carbonyl)-1⁵-fluoro-4-oxo-3-aza-1(1,3),2(1,2)-dibenzenacyclononaphane-2⁴-yl)carbamate

| Example | Structure | LCMS [M + 1] | Hu FXIa Ki (nM) |
|---|---|---|---|
| 29a | methyl ((R)-9-((R)-6-chloro-2-oxo-1,2-dihydrospiro[benzo[d][1,3]oxazine-4,3'-piperidine]-1'-carbonyl)-1$^5$-fluoro-4-oxo-3-aza-1(1,3),2(1,2)-dibenzenacyclononaphane-2$^4$-yl)carbamate | 635 | 222 |
| 29b | methyl ((S)-9-((R)-6-chloro-2-oxo-1,2-dihydrospiro[benzo[d][1,3]oxazine-4,3'-piperidine]-1'-carbonyl)-1$^5$-fluoro-4-oxo-3-aza-1(1,3),2(1,2)-dibenzenacyclononaphane-2$^4$-yl)carbamate | 635 | >8750 |
| 30a | methyl ((S)-9-((R)-6-chloro-5-fluoro-2-oxo-1,2-dihydrospiro[benzo[d][1,3]oxazine-4,3'-piperidine]-1'-carbonyl)-1$^5$-fluoro-4-oxo-3-aza-1(1,3),2(1,2)-dibenzenacyclononaphane-2$^4$-yl)carbamate | 653 | >8750 |
| 30b | methyl ((R)-9-((R)-6-chloro-5-fluoro-2-oxo-1,2-dihydrospiro[benzo[d][1,3]oxazine-4,3'-piperidine]-1'-carbonyl)-1$^5$-fluoro-4-oxo-3-aza-1(1,3),2(1,2)-dibenzenacyclononaphane-2$^4$-yl)carbamate | 653 | 68.8 |

Example 31

Ethyl (1²Z,6E)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphan-6-ene-4-carboxylate (EX-31)

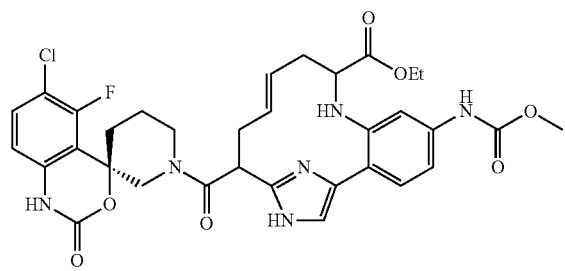

Synthetic Scheme for Example 31

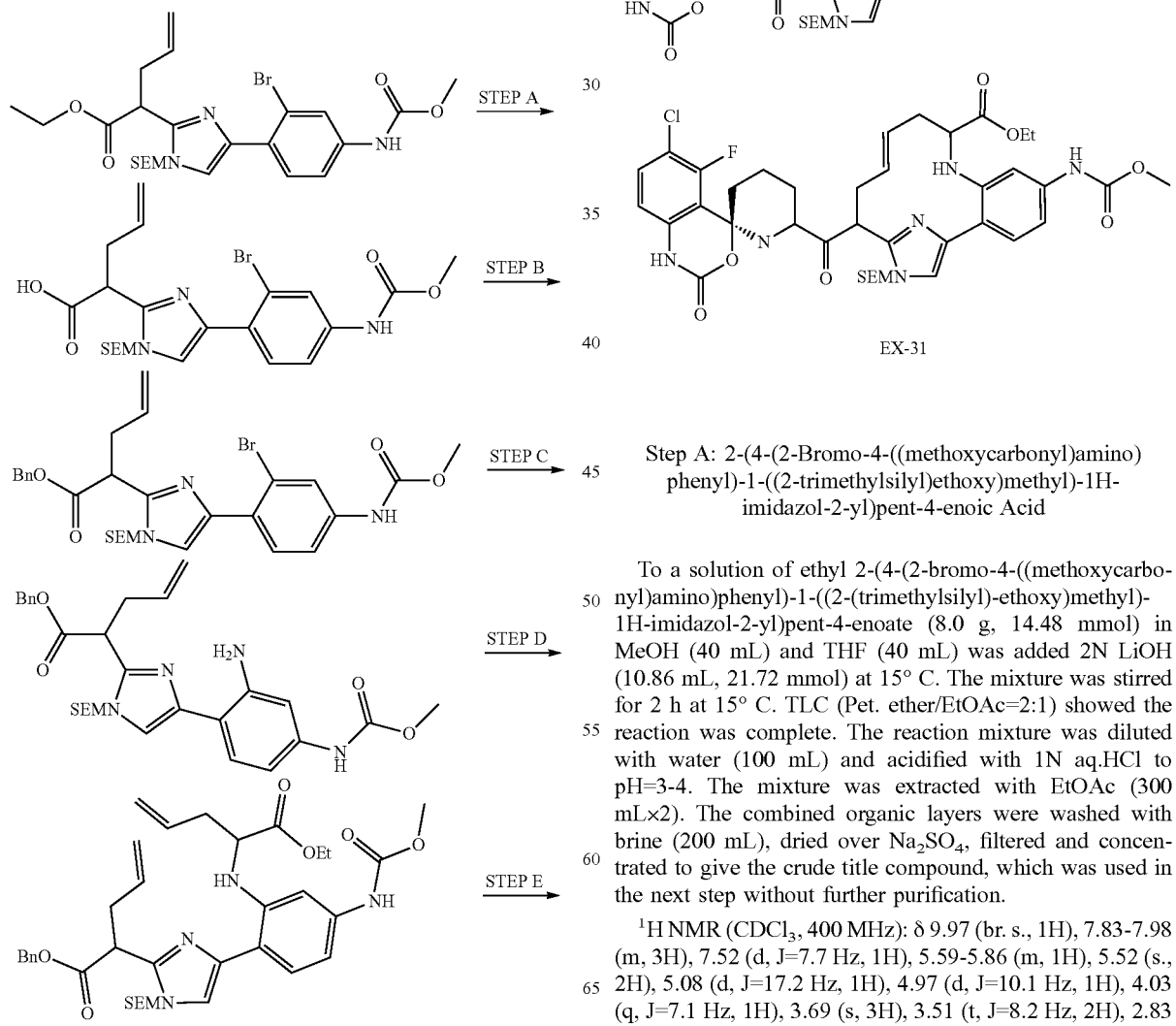

Step A: 2-(4-(2-Bromo-4-((methoxycarbonyl)amino)phenyl)-1-((2-trimethylsilyl)ethoxy)methyl)-1H-imidazol-2-yl)pent-4-enoic Acid To a solution of ethyl 2-(4-(2-bromo-4-((methoxycarbonyl)amino)phenyl)-1-((2-(trimethylsilyl)-ethoxy)methyl)-1H-imidazol-2-yl)pent-4-enoate (8.0 g, 14.48 mmol) in MeOH (40 mL) and THF (40 mL) was added 2N LiOH (10.86 mL, 21.72 mmol) at 15° C. The mixture was stirred for 2 h at 15° C. TLC (Pet. ether/EtOAc=2:1) showed the reaction was complete. The reaction mixture was diluted with water (100 mL) and acidified with 1N aq.HCl to pH=3-4. The mixture was extracted with EtOAc (300 mL×2). The combined organic layers were washed with brine (200 mL), dried over $Na_2SO_4$, filtered and concentrated to give the crude title compound, which was used in the next step without further purification.

¹H NMR ($CDCl_3$, 400 MHz): δ 9.97 (br. s., 1H), 7.83-7.98 (m, 3H), 7.52 (d, J=7.7 Hz, 1H), 5.59-5.86 (m, 1H), 5.52 (s., 2H), 5.08 (d, J=17.2 Hz, 1H), 4.97 (d, J=10.1 Hz, 1H), 4.03 (q, J=7.1 Hz, 1H), 3.69 (s, 3H), 3.51 (t, J=8.2 Hz, 2H), 2.83 (d, J=5.5 Hz, 2H), 0.80-0.96 (m, 2H), 0.03 (s, 9H).

Step B: Benzyl 2-(4-(2-bromo-4-((methoxycarbonyl)amino)phenyl)-1-((2-(trimethylsilyl)ethoxy)-methyl)-1H-imidazol-2-yl)pent-4-enoate To a solution of 2-(4-(2-bromo-4-((methoxycarbonyl)amino)phenyl)-1-((2-(trimethylsilyl)eth-oxy)methyl)-1H-imidazol-2-yl)pent-4-enoic acid (7.3 g, 13.92 mmol) in DMF (60 mL) was added (bromomethyl)benzene (2.86 g, 16.70 mmol) and $Cs_2CO_3$ (5.44 g, 16.70 mmol) at 15° C. The mixture was stirred for 5 h at 15° C. The reaction mixture was quenched with water (200 mL) and extracted with EtOAc (200 mL×2). The combined organic layers were washed with brine (200 mL), dried over $Na_2SO_4$, filtered and concentrated. The residue was purified by flash column chromatography on silica gel (pet. ether/EtOAc=6:1-4:1) to give the title compound.

$^1$H NMR ($CDCl_3$, 400 MHz): δ 8.04 (d, J=8.6 Hz, 1H), 7.84 (br. s., 1H), 7.66 (s, 1H), 7.22-7.38 (m, 5H), 6.70 (br. s., 1H), 5.78-5.92 (m, 1H), 5.40 (d, J=11.2 Hz, 1H), 5.11-5.24 (m, 4H), 5.04 (d, J=10.1 Hz, 1H), 4.04-4.12 (m, 1H), 3.82 (s, 3H), 3.50 (t, J=8.3 Hz, 2H), 2.92-3.10 (m, 2H), 0.85-0.96 (m, 2H), 0.00 (s, 9H).

Step C: Benzyl2-(4-(2-amino-4-((methoxycarbonyl)amino)phenyl)-1-((2-(trimethylsilyl)ethoxy)-methyl)-1H-imidazol-2-yl)pent-4-enoate To a solution of benzyl 2-(4-(2-bromo-4-((methoxycarbonyl)amino)phenyl)-1-((2-(trimethyl-silyl)ethoxy)methyl)-1H-imidazol-2-yl)pent-4-enoate (5.82 g, 9.47 mmol) in DMSO (45 mL) in a clean and dry sealed tube, was added $K_2CO_3$ (3.93 g, 28.4 mmol), CuI (0.180 g, 0.947 mmol) and L-proline (0.327 g, 2.84 mmol). A stream of nitrogen was bubbled through the mixture for 2 min. To the mixture was added ammonium hydroxide (1.473 g, 10.51 mmol). The tube was sealed and stirred at 85° C. for 18 h. The reaction mixture was quenched with water (200 mL) and extracted with EtOAc (100 mL×3). The combined organic layers were washed with brine (100 mL), dried over $Na_2SO_4$, filtered and concentrated. The residue was purified by flash column chromatography on silica gel (PE/EtOAc=4:1-3:1) to give the title compound as an oil. LC/MS (ESI) m/z 551.4 (M+1).

$^1$H NMR ($CDCl_3$, 400 MHz): δ 7.31 (d, J=15.4 Hz, 5H), 7.13 (d, J=3.7 Hz, 1H), 6.90 (br. s., 1H), 6.51-6.70 (m, 2H), 5.62 (br. s., 1H), 5.39 (br. s., 1H), 5.16 (br. s., 4H), 5.03 (br. s., 1H), 4.06 (br. s., 1H), 3.80 (s, 3H), 3.49 (d, J=4.0 Hz, 2H), 2.99 (br. s., 2H), 0.91 (br. s., 2H), 0.01 (s, 9H).

Step D: Benzyl 2-(4-(2-((1-ethoxy-1-oxopent-4-en-2-yl)amino)-4-((methoxycarbonyl)amino) phenyl)-1-((2-(trimethylsilyl)ethoxy)methyl)-1H-imidazol-2-yl)pent-4-enoate To a solution of benzyl 2-(4-(2-amino-4-((methoxycarbonyl)amino)phenyl)-1-((2-(trimethyl-silyl)ethoxy)methyl)-1H-imidazol-2-yl)pent-4-enoate (2.32 g, 4.21 mmol) in acetonitrile (20 mL) was added ethyl 2-oxoacetate (1.286 mL, 6.32 mmol), followed by maleic acid (0.489 g, 4.21 mmol). Then allyltributylstannane (2.351 mL, 7.58 mmol) was added. The mixture was stirred at 15° C. for 18 h. The reaction was quenched with sat. aq. KF (100 mL) and stirred for 10 min. Then the mixture was extracted with EtOAc (50 mL×3). The combined organic layers were washed with brine (50 mL), dried over $Na_2SO_4$, filtered and concentrated. The residue was purified by flash column chromatography on silica gel (PE/EtOAc=6:1-4:1) to afford the title compound. LC/MS (ESI) m/z 677.4 (M+1).

$^1$H NMR ($CDCl_3$, 400 MHz): δ 7.31 (d, J=12.6 Hz, 5H), 7.15 (br. s., 1H), 6.71 (br. s., 2H), 6.54 (br. s., 1H), 5.76-6.00 (m, 2H), 5.41 (d, J=10.8 Hz, 1H), 5.06-5.24 (m, 6H), 5.02 (br. s., 1H), 4.11-4.30 (m, 3H), 4.05 (d, J=6.8 Hz, 1H), 3.80 (s., 3H), 3.48 (t, J=7.7 Hz, 2H), 2.95-3.08 (m, 2H), 2.67 (br. s., 2H), 1.21-1.35 (m, 3H), 0.90 (t, J=6.8 Hz, 2H), 0.04-0.06 (m, 9H).

Step E: 9-Benzyl 4-ethyl ($1^2Z,6E$)-$2^4$-((methoxycarbonyl)amino)-$1^1$-((2-(trimethylsilyl)ethoxy)methyl)-$1^1$H-3-aza-1(4,2)-imidazola-2(1,2)-benzenacyclononaphan-6-ene-4,9-dicarboxylate To a solution of benzyl 2-(4-(2-((1-ethoxy-1-oxopent-4-en-2-yl)amino)-4-((methoxycarbon-yl)amino)phenyl)-1-((2-(trimethylsilyl)ethoxy)methyl)-1H-imidazol-2-yl)pent-4-enoate (2.35 g, 3.47 mmol) in DCE (200 mL) was added Grubbs II catalyst (0.884 g, 1.042 mmol). The resulting mixture was bubbled with $N_2$ for 5 min and then stirred at 120° C. for 30 min under microwave irritation. Solvent was removed and the residue was purified by flash column chromatography on silica gel (PE/EtOAc=4:1) to give the title compound. LC/MS (ESI) m/z 649.4 (M+1).

Step F: ($1^2Z,6E$)-4-(Ethoxycarbonyl)-$2^4$-((methoxycarbonyl)amino)-$1^1$-((2-(trimethylsilyl)ethoxy)methyl)-$1^1$H-3-aza-1(4,2)-imidazola-2(1,2)-benzenacyclononaphan-6-ene-9-carboxylic Acid To a solution of 9-benzyl 4-ethyl ($1^2Z,6E$)-$2^4$-((methoxycarbonyl)amino)-$1^1$-((2-(trimethylsilyl)ethoxy)methyl)-$1^1$H-3-aza-1(4,2)-imidazola-2(1,2)-benzenacyclononaphan-6-ene-4,9-dicarboxylate (150 mg, 0.231 mmol) in MeOH (2.0 mL) was added Pd—C(10%, 49.2 mg, 0.046 mmol). The mixture was stirred for 1 h at 15° C. under $H_2$ atmosphere. The reaction mixture was filtered and the filtrate was concentrated to give the title compound, which was used in the next step without further purification. LC/MS (ESI) m/z 559.3 (M+1).

Step G: Ethyl ($1^2Z,6E$)-9-((R)-6-chloro-5-fluoro-2-oxo-1,2-dihydrospiro[benzo[d][1,3]oxazine-4,3'-piperidine]-1'-carbonyl)-$2^4$-((methoxycarbonyl)amino)-$1^1$-((2-(trimethylsilyl)ethoxy)methyl)-$1^1$H-3-aza-1(4,2)-imidazola-2(1,2)-benzenacyclononaphan-6-ene-4-carboxylate To a solution of ($1^2Z,6E$)-4-(ethoxycarbonyl)-$2^4$-((methoxycarbonyl)amino)-$1^1$-((2-(trimethylsilyl)ethoxy)methyl)-$1^1$H-3-aza-1(4,2)-imidazola-2(1,2)-benzenacyclononaphan-6-ene-9-carboxylic acid (100 mg, 0.179 mmol) in DCM (6.0 mL) was added HATU (82 mg, 0.215 mmol) at 15° C. The mixture was stirred for 10 min. Then (R)-6-chloro-5-fluorospiro[benzo[d][1,3]oxazine-4,3'-piperidin]-2 (1H)-one. HCl (55.0 mg, 0.179 mmol) and DIPEA (0.125 mL, 0.716 mmol) were added. The mixture was stirred for 1.5 h. The reaction mixture was quenched with water (20 mL) and extracted with EtOAc (20 mL×3). The combined organic layers were washed with brine (20 mL), dried over $Na_2SO_4$, filtered and concentrated to give the title compound, which was used in the next step without further purification. LC/MS (ESI) m/z 811.4 (M+H)

Step H: Ethyl (1²Z,6E)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphan-6-ene-4-carboxylate (EX-31)

To a solution of ethyl (1²Z,6E)-9-((R)-6-chloro-5-fluoro-2-oxo-1,2-dihydrospiro[benzo[d][1,3]oxazine-4,3'-piperidine]-1'-carbonyl)-24-((methoxycarbonyl)amino)-1¹-((2-(trimethylsilyl)ethoxy)methyl)-1¹H-3-aza-1(4,2)-imidazola-2(1,2)-benzenacyclononaphan-6-ene-4-carboxylate (120 mg, 0.148 mmol) in DCM (2.0 mL) was added TFA (2.0 mL, 26.0 mmol) at 15° C. and the mixture was stirred for 4 h. The reaction mixture was quenched with sat. aq. NaHCO₃ (30 mL) and extracted with EtOAc (30 mL×2). The combined organic layers were washed with brine (30 mL), dried over Na₂SO₄, filtered and concentrated. The residue was purified by prep-HPLC to give Example 31. LC/MS (ESI) m/z 681.0 (M+H)

¹H NMR (CD₃OD, 400 MHz): δ 7.38-7.58 (m, 2H), 7.08-7.38 (m, 2H), 6.65-6.84 (m, 1H), 5.41-5.67 (m, 2H), 4.95 (d, J=8.6 Hz, 2H), 4.04-4.27 (m, 3H), 3.73 (d, J=2.0 Hz, 3H), 3.31-3.52 (m, 4H), 3.08-3.29 (m, 2H), 2.48-3.00 (m, 1H), 2.04-2.47 (m, 2H), 1.16-1.33 (m, 3H).

Example 32 and 33

Ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylate (EX-32) and (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylic acid (EX-33)

Synthetic Scheme for Example 32 and 33

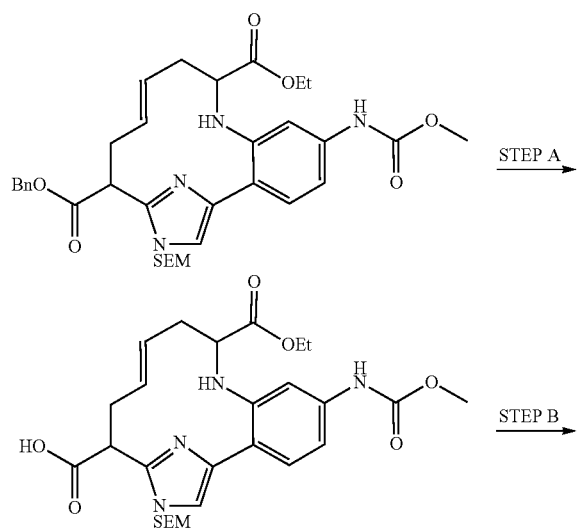

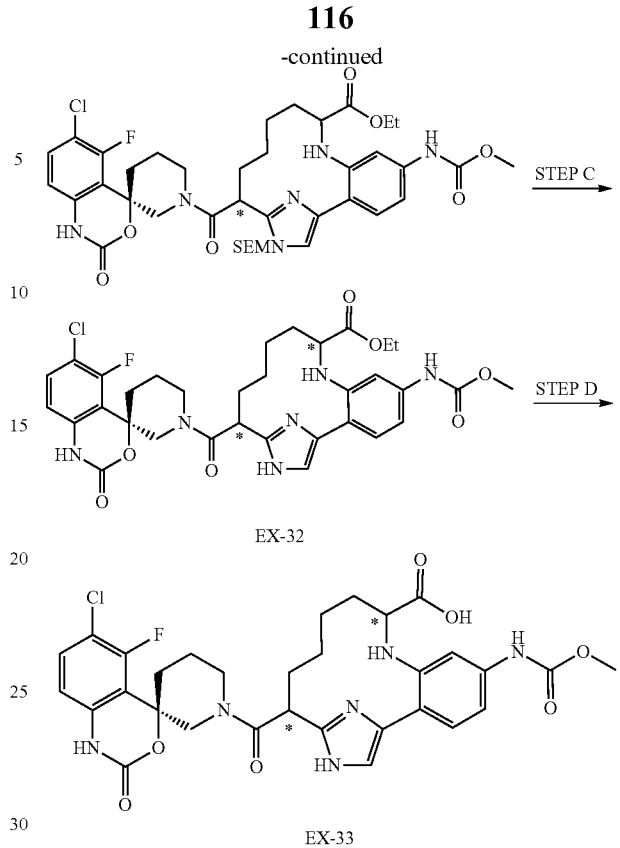

Step A: (1²Z,6E)-4-(Ethoxycarbonyl)-2⁴-((methoxycarbonyl)amino)-1¹-((2-(trimethylsilyl)ethoxy)methyl)-1¹H-3-aza-1(4,2)-imidazola-2(1,2)-benzenacyclononaphan-6-ene-9-carboxylic Acid To a solution of 9-benzyl 4-ethyl (1²Z,6E)-2⁴-((methoxycarbonyl)amino)-1¹-((2-(trimethylsilyl)ethoxy)methyl)-1¹H-3-aza-1(4,2)-imidazola-2(1,2)-benzenacyclononaphan-6-ene-4,9-dicarboxylate (710 mg, 1.094 mmol) in MeOH (15 mL) was added Pd—C(10%, 2329 mg, 2.189 mmol). The mixture was stirred for 18 h at 15° C. under H₂ (15 psi). The reaction mixture was filtered and the filtrate was concentrated to give the title compound, which was used in the next step without further purification. LC/MS (ESI) m/z 561.3 (M+1).

Step B: Ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹-((2-(trimethylsilyl)ethoxy)methyl)-1¹H-3-aza-1(4,2)-imidazola-2(1,2)-benzenacyclononaphane-4-carboxylate To a solution of (1²Z,6E)-4-(ethoxycarbonyl)-2⁴-((methoxycarbonyl)amino)-1¹-((2-(trimethylsilyl)ethoxy)methyl)-1¹H-3-aza-1(4,2)-imidazola-2(1,2)-benzenacyclononaphan-6-ene-9-carboxylic acid (366 mg, 0.653 mmol) in DCM (15 mL) was added HATU (298 mg, 0.783 mmol) at 15° C. The mixture was stirred for 10 min. Then (R)-6-chloro-5-fluorospiro[benzo[d][1,3]oxazine-4,3'-piperidin]-2(1H)-one HCl (200 mg, 0.653 mmol) and DIPEA (0.456 mL, 2.61 mmol) were added. The mixture was stirred for 1.5 h. The reaction mixture was quenched with water (50 mL) and extracted with EtOAc (40 mL×3). The combined organic layers were washed with brine (40 mL), dried over Na₂SO₄, filtered and concentrated to give the title compound, which was used in the next step without further purification. LC/MS (ESI) m/z 813.3 (M+1).

Four diastereomers were separated by SFC (Column: Chiralpak AD-3 100×4.6 mm I.D., 3 um; Mobile phase: 40% ethanol (0.05% DEA) in $CO_2$; Flow rate: 2.8 mL/min) to give isomer A, isomer B, isomer C and isomer D in the order they were eluted, all as solids. LC/MS (ESI) m/z 813.0 (M+1⁻).

Step C: Ethyl (Z)-9-((R)-6-chloro-5-fluoro-2-oxo-1, 2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylate (EX-32)

To a solution of ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹-((2-(trimethylsilyl)ethoxy)methyl)-1¹H-3-aza-1(4,2)-imidazola-2(1,2)-benzenacyclononaphane-4-carboxylate (100 mg, 0.123 mmol) in DCM (2.0 mL) was added TFA (2.0 mL, 26.0 mmol) at 15° C. The mixture was stirred for 4 h. The reaction mixture was quenched with sat. aq. NaHCO₃ (20 mL) and extracted with EtOAc (20 mL×3). The combined organic layers were washed with brine (20 mL), dried over Na₂SO₄, filtered and concentrated. The residue was purified by prep-HPLC to give EX-32. LC/MS (ESI) m/z 683.3 (M+1).

¹H NMR (CD₃OD, 400 MHz): δ 7.27-7.67 (m, 4H), 7.09-7.22 (m, 1H), 6.71-6.82 (m, 1H), 4.88-5.06 (m, 4H), 4.33-4.75 (m, 2H), 3.94-4.31 (m, 3H), 3.68-3.80 (s, 3H), 3.37-3.51 (m, 1H), 2.78-3.27 (m, 2H), 1.94-2.41 (m, 3H), 1.35-1.92 (m, 5H), 1.06-1.19 (m, 3H).

EX-32a

A solution of isomer A in step B (150 mg, 0.184 mmol) and (R)-2-amino-3-mercaptopropanoic acid (112 mg, 0.922 mmol) in HCl/dioxane (3.0 mL, 12.00 mmol) was stirred at 75° C. for 1 h under N₂ in a sealed tube. The reaction mixture was concentrated. The residue was purified by prep-HPLC to give the crude desired product, which was further purified by SFC (Column: Chiralcel OD-3 100×4.6 mm I.D., 3 um, Mobile phase: 40% iso-propanol (0.05% DEA) in $CO_2$, Flow rate: 2.8 mL/min) to give EX-32a. LC/MS (ESI) m/z 683.3 (M+1).

¹H NMR (CD₃OD, 400 MHz): δ 7.43 (t, J=8.2 Hz, 1H), 7.25 (d, J=8.2 Hz, 2H), 6.98-7.14 (m, 2H), 6.76 (d, J=8.4 Hz, 1H), 4.97 (d, J=13.9 Hz, 1H), 4.30-4.76 (m, 1H), 3.94-4.20 (m, 3H), 3.69-3.78 (m, 3H), 3.22 (d, J=10.8 Hz, 1H), 3.12 (d, J=13.9 Hz, 1H), 2.75-3.07 (m, 1H), 1.56-2.56 (m, 9H), 1.26-1.55 (m, 5H), 1.13 (t, J=7.1 Hz, 3H).

EX-32b

A solution of isomer B in step B (147 mg, 0.181 mmol) and (R)-2-amino-3-mercaptopropanoic acid (109 mg, 0.904 mmol) in HCl/dioxane (3.0 mL, 12.00 mmol) was sealed and stirred for 1 h at 75° C. under N₂. The reaction mixture was concentrated to give a residue, which was purified by prep-HPLC to give EX-32b. LC/MS (ESI) m/z 683.3 (M+H).

¹H NMR (CD₃OD, 400 MHz): δ 7.55-7.68 (m, 1H), 7.31-7.51 (m, 3H), 7.11-7.24 (m, 1H), 6.72-6.82 (m, 1H), 4.75 (d, J=9.0 Hz, 2H), 3.91-4.17 (m, 3H), 3.67-3.82 (m, 3H), 3.42 (t, J=12.3 Hz, 1H), 3.25 (s, 1H), 2.77-3.16 (m, 1H), 2.44-2.61 (m, 1H), 1.96-2.39 (m, 4H), 1.64-1.94 (m, 4H), 1.33-1.63 (m, 3H), 1.05-1.19 (m, 3H).

EX-32c

A solution of isomer C in step B (187 mg, 0.230 mmol) and (R)-2-amino-3-mercaptopropanoic acid (139 mg, 1.150 mmol) in HCl/dioxane (3.0 mL, 12.00 mmol) was sealed and stirred for 1 h at 75° C. under N₂. The reaction mixture was concentrated. The residue was purified by prep-HPLC to give a crude product, which was purified by SFC (Column: Chiralpak AD-3 50*4.6 mm I.D., 3 um, Mobile phase: 40% iso-propanol (0.05% DEA) in $CO_2$, Flow rate: 4 mL/min) to give EX-32c. LC/MS (ESI) m/z 683.3 (M+H).

¹H NMR (CD₃OD, 400 MHz): δ 7.41 (t, J=8.0 Hz, 1H), 7.13-7.29 (m, 2H), 6.89-7.07 (m, 2H), 6.74 (d, J=8.6 Hz, 1H), 4.91-5.03 (m, 1H), 4.52-4.76 (m, 1H), 4.19-4.46 (m, 2H), 4.04 (br. s., 2H), 3.72 (s, 3H), 3.25 (br. s., 1H), 3.13 (d, J=13.9 Hz, 1H), 2.82 (t, J=12.5 Hz, 1H), 2.46-2.62 (m, 1H), 1.88-2.36 (m, 4H), 1.61-1.87 (m, 2H), 1.24-1.60 (m, 4H), 1.14 (t, J=6.9 Hz, 3H).

EX-32d

A solution of isomer D in step B (133 mg, 0.164 mmol) and (R)-2-amino-3-mercaptopropanoic acid (99 mg, 0.818 mmol) in HCl/dioxane (3.0 mL, 12.00 mmol) was sealed and stirred for 1 h at 75° C. under N₂. LCMS showed desired product and the reaction was complete. The reaction mixture was concentrated to give a residue, which was purified by prep-HPLC to give EX-32d. MS (ESI) m/z 683.3 (M+H)

¹H NMR (CD₃OD, 400 MHz): δ 7.56 (s, 1H), 7.40-7.51 (m, 1H), 7.25-7.39 (m, 2H), 7.14 (d, J=6.7 Hz, 1H), 6.71-6.81 (m, 1H), 4.41-4.77 (m, 2H), 3.95-4.16 (m, 3H), 3.74 (s, 3H), 3.44 (t, J=12.5 Hz, 1H), 3.02-3.29 (m, 3H), 1.93-2.62 (m, 5H), 1.59-1.85 (m, 4H), 1.50 (br. s, 2H), 1.07-1.20 (m, 3H).

Step D: (Z)-9-((R)-6-Chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylic acid (EX-33)

To a solution of ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylate (10 mg, 0.015 mmol) in THF (0.8 mL) and MeOH (0.8 mL) was added 2N LiOH (0.8 mL, 1.600 mmol) at 30° C. and the mixture was stirred for 1 h. LCMS showed the reaction was complete. The reaction mixture was acidified with aq. 1N HCl to pH 3-4 and extracted with EtOAc (10 mL×2). The combined organic layers were washed with brine (10 mL), dried over Na₂SO₄, filtered and concentrated. The residue was purified by prep-HPLC (TFA) to give EX-33. MS (ESI) m/z 655.3 (M+H).

¹H NMR (CD₃OD, 400 MHz): δ 7.27-7.64 (m, 4H), 7.12-7.26 (m, 1H), 6.70-6.80 (m, 1H), 4.88-5.03 (m, 4H), 4.56-4.71 (m, 1H), 4.01-4.23 (m, 1H), 3.66-3.79 (s, 3H), 3.31-3.49 (m, 2H), 2.99-3.28 (m, 4H), 2.47-2.61 (m, 1H), 2.20-2.36 (m, 1H), 1.41-1.90 (m, 4H).

By using procedures similar to those described above, the following compounds were synthesized and characterized by LCMS.

| Example | Structure | LCMS [M + 1] | Hu FXIa Ki (nM) |
|---------|-----------|--------------|-----------------|
| 31 | ethyl (1²Z,6E)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphan-6-ene-4-carboxylate | 681 | 41.1 |
| 32 (mixture of two diastereomers) | ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylate | 683 | 4.94 |
| 32a | ethyl (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylate (isomer a) | 683 | 142.6 |

| Example | Structure | LCMS [M + 1] | Hu FXIa Ki (nM) |
|---|---|---|---|
| 32b | ethyl (Z)-9-((R)-6-chloro-5-fluoro-2-oxo-1,2-dihydrospiro[benzo[d][1,3]oxazine-4,3'-piperidine]-1'-carbonyl)-2[4]-((methoxycarbonyl)amino)-1[1]H-3-aza-1(4,2)-imidazola-2(1,2)-benzenacyclononaphane-4-carboxylate (isomer b) | 683 | 0.62 |
| 32c | ethyl (Z)-9-((R)-6-chloro-5-fluoro-2-oxo-1,2-dihydrospiro[benzo[d][1,3]oxazine-4,3'-piperidine]-1'-carbonyl)-2[4]-((methoxycarbonyl)amino)-1[1]H-3-aza-1(4,2)-imidazola-2(1,2)-benzenacyclononaphane-4-carboxylate (isomer c) | 683 | 535.8 |
| 32d | ethyl (Z)-9-((R)-6-chloro-5-fluoro-2-oxo-1,2-dihydrospiro[benzo[d][1,3]oxazine-4,3'-piperidine]-1'-carbonyl)-2[4]-((methoxycarbonyl)amino)-1[1]H-3-aza-1(4,2)-imidazola-2(1,2)-benzenacyclononaphane-4-carboxylate (isomer d) | 683 | >875 |

| Example | Structure | LCMS [M + 1] | Hu FXIa Ki (nM) |
|---|---|---|---|
| 33 | (Z)-9-((R)-6-chloro-5-fluoro-2-oxo-1,2-dihydrospiro[benzo[d][1,3]oxazine-4,3'-piperidine]-1'-carbonyl)-2⁴-((methoxycarbonyl)amino)-1¹H-3-aza-1(4,2)-imidazola-2(1,2)-benzenacyclononaphane-4-carboxylic acid | 655 | 135.5 |

Example 34 and 35

Ethyl 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylate (EX-34) and 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylic Acid (EX-35)

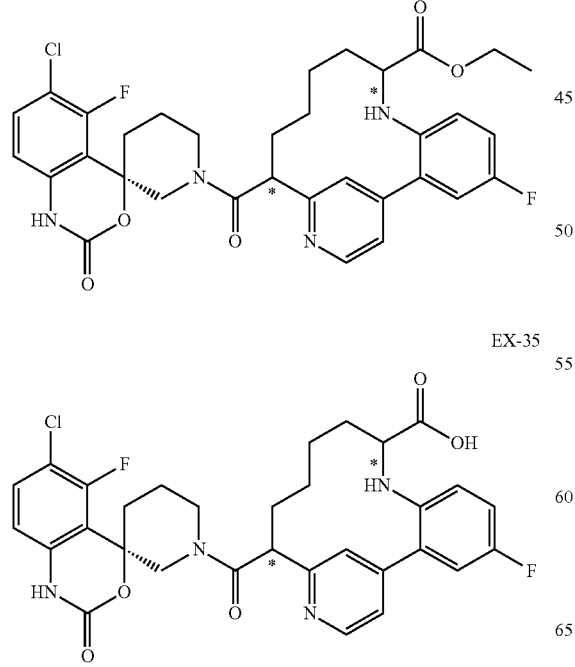

Synthetic Scheme for Example 34 and 35

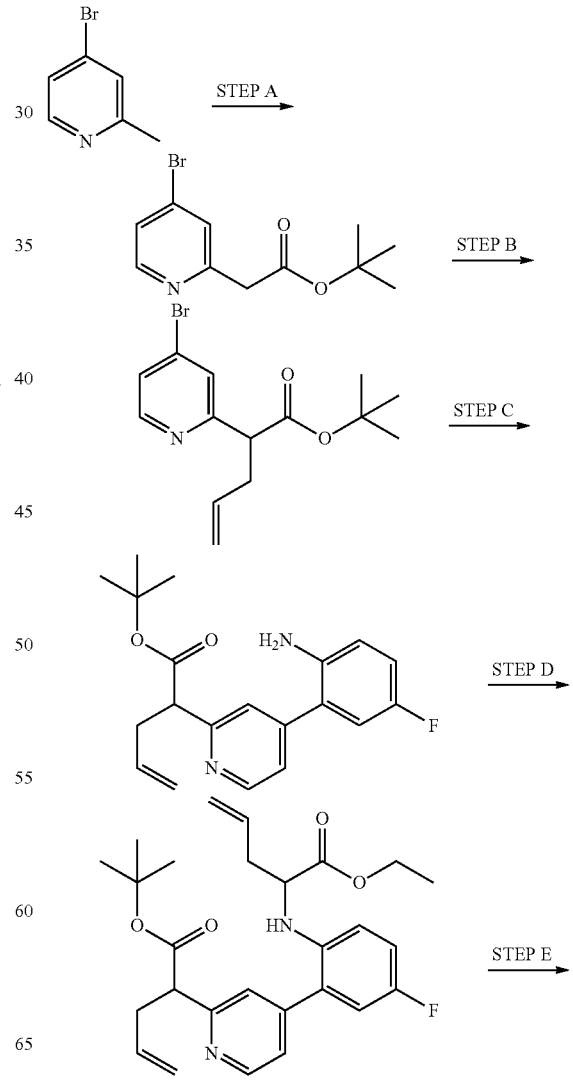

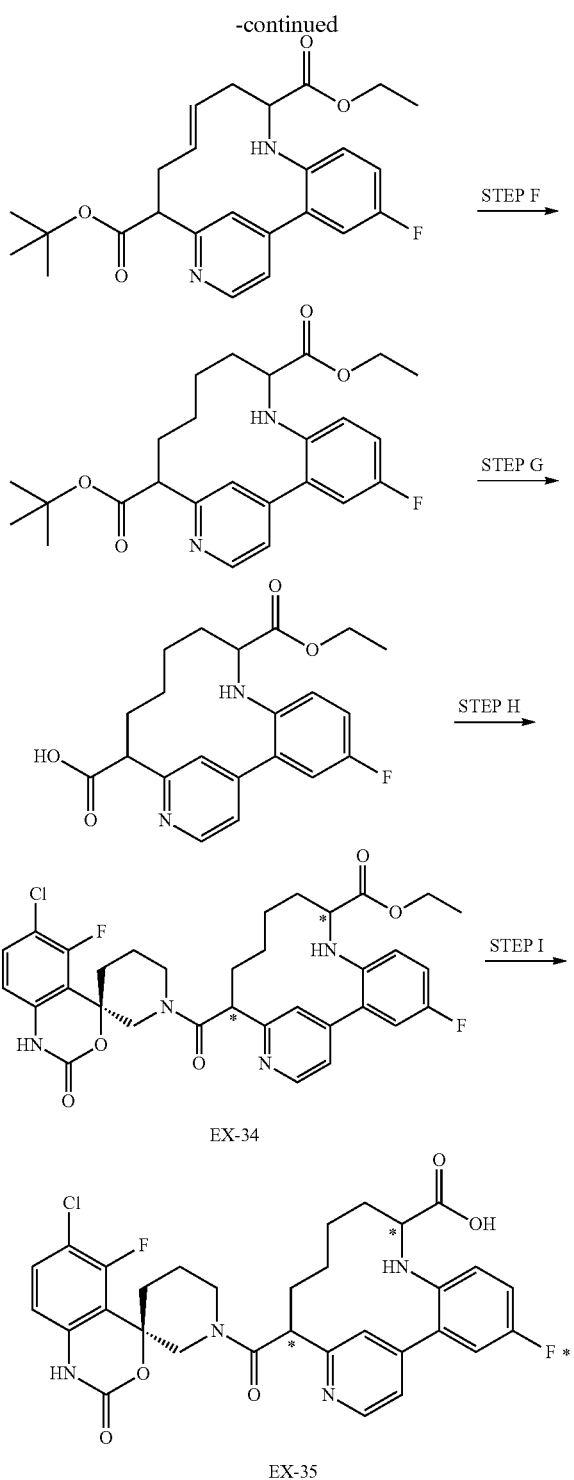

EX-34

EX-35

Step A: tert-Butyl 2-(4-bromopyridin-2-yl)acetate

LDA (43.6 mL, 87 mmol) was added dropwise to a stirred, −78° C. mixture of tert-butyl 2-(4-bromopyridin-2-yl)acetate (8.8 g, 32.3 mmol, 55.6% yield) in THF (291 mL) and the mixture was stirred at −78° C. for 1 h. Boc₂O (16.20 mL, 69.8 mmol) in THF (100 mL) was cannulated to the mixture. The mixture was stirred at −78° C. for 2 h. then slowly warmed to RT and stirred at RT overnight. LCMS showed that starting material had disappeared. The mixture was diluted with ethyl acetate (300 mL), washed with aqueous saturated ammonium chloride (100 mL), dried over MgSO₄, filtered and the solvent was evaporated under reduced pressure. The residue was purified by flash column chromatography on silica gel (15% OAc/isohexane) to give the title compound. LC/MS: m/z=273.9 [M+1].

Step B: tert-Butyl 2-(4-bromopyridin-2-yl)pent-4-enoate

LDA (14.15 mL, 28.3 mmol) was added to a stirred, −78° C. mixture of tert-butyl 2-(4-bromopyridin-2-yl)acetate (5.5 g, 20.21 mmol) in THF (101 mL) and the mixture was stirred at −78° C. for 1 h. Allyl bromide (2.448 mL, 28.3 mmol) was added to the cold mixture, the resultant mixture was kept stirring at −78° C. 3 h. Then it was slowly warmed up to RT and stirred at RT for 3 h. The mixture was diluted with ethyl acetate (200 mL), washed with aq. sat. ammonium chloride (1×150 mL), dried over MgSO₄, filtered and the solvent was evaporated under reduced pressure. the residue was purified by falsh column chromatography on silica gel (15% EtOAc/isohexane) to give the title compound. MS: m/z=313.9 [M+1].

Step C: tert-Butyl 2-(4-(2-amino-5-fluorophenyl)pyridin-2-yl)pent-4-enoate

4-Fluoro-2-(4,4,5,5-tetramethyl-1,3,2-dioxaborolan-2-yl)aniline (1.822 g, 7.69 mmol), tert-butyl 2-(4-bromopyridin-2-yl)pent-4-enoate (2 g, 6.41 mmol), chloro(2-dicyclohexylphosphino-2',4',6'-triisopropyl-1,1'-biphenyl)[2-(2-aminoethyl)phenyl]palladium(II) (0.473 g, 0.641 mmol) and K₃PO₄ (4.08 g, 19.22 mmol) were mixed in a pressure release vial, degassed and backfilled with N₂ (3×), THF (24.02 mL) and water (8.01 mL) were added subsequently, the resultant mixture was degassed and backfilled with N₂ (3×), heated to 80° C. for 1 h. The mixture was diluted with ethyl acetate (20 mL), washed with aq. sat. sodium bicarbonate (1x 10 mL), dried over MgSO₄, filtered and the solvent was evaporated under reduced pressure. The residue was purified by column chromatography on silica gel (20% EtOAc in isohexane) to give the title compound. MS: m/z=343.2 (M+1).

Step D: tert-Butyl 2-(4-(2-((1-ethoxy-1-oxopent-4-en-2-yl)amino)-5-fluorophenyl)pyridin-2-yl)pent-4-enoate Ethyl glyoxolate (1.694 mL, 8.32 mmol) was added to a stirred mixture of tert-butyl 2-(4-(2-amino-5-fluorophenyl)pyridin-2-yl)pent-4-enoate (1.9 g, 5.55 mmol) and Maleic acid (0.644 g, 5.55 mmol) in acetonitrile (25 mL) at RT, and the mixture was stirred at RT for 30 min. Allylbutyltin (3.10 mL, 9.99 mmol) was added to the mixture and the resultant mixture was kept stirring at RT overnight. The mixture was diluted with ethyl acetate (40 mL), washed with aqueous sodium hydroxide (0.5M, 1×10 mL), and brine (10 mL), dried over MgSO₄, filtered and the solvent was evaporated under reduced pressure. The residue was purified by flash column chromatography on silica gel (20% EtOAc in isohexane) to give the title compound. LC/MS: m/z=469.2 [M+1].

Step E: 9-(tert-Butyl) 4-ethyl (E)-2⁵-fluoro-3-aza-1(4,2)-pyridina-2(1,2)-benzenacyclononaphan-6-ene-4,9-dicarboxylate Zhan catalyst-1B (157 mg, 0.213 mmol) was added to a stirred mixture of tert-butyl 2-(4-(2-((1-ethoxy-1-oxopent- 4-en-2-yl)amino)-5-fluorophenyl)pyridin-2-yl)pent-4-enoate (500 mg, 1.067 mmol) and pTSA (162 mg, 0.854 mmol) in DCE (25 mL) at RT, the resultant mixture was degassed and backfilled with $N_2$ (3×), and the mixture was stirred at 50° C. overnight. The mixture was diluted with DCM (6 mL), washed with aq. sat. sodium bicarbonate (1×4 mL), dried over $MgSO_4$, filtered and the solvent was evaporated under reduced pressure. the residue was purified by flash column chromatography on silica gel (15-60% EtOAc in isohexane) to give the title compound. LC/MS: m/z=441.0 [M+1].

Step F: 9-(tert-Butyl) 4-ethyl $2^5$-fluoro-3-aza-1(4,2)-pyridina-2(1,2)-benzenacyclononaphane-4,9-dicarboxylate $Pd(OH)_2$ (20%, 4.78 mg, 6.81 μmol) was added to a stirred mixture of 9-(tert-butyl) 4-ethyl (E)-$2^5$-fluoro-3-aza-1(4,2)-pyridina-2(1,2)-benzenacyclononaphan-6-ene-4,9-dicarboxylate (30 mg, 0.068 mmol) in MeOH (2 mL) at RT and the mixture was stirred at RT overnight. The mixture was filtered off and washed with MeOH (3 mL), the filtrate was concentrated to give the title compound. LC/MS: m/z=442.9 [M+1].

Step G: 4-(Ethoxycarbonyl)-$2^5$-fluoro-3-aza-1(4,2)-pyridina-2(1,2)-benzenacyclononaphane-9-carboxylic Acid HCl (4M in dioxane) (1 mL, 4.00 mmol) was added to 9-(tert-butyl) 4-ethyl $2^5$-fluoro-3-aza-1(4,2)-pyridina-2(1,2)-benzenacyclononaphane-4,9-dicarboxylate (30 mg, 0.068 mmol), and the mixture was stirred at RT overnight. The reaction was monitor with LCMS over time. The mixture was concentrated to dryness to give the title compound. LC/MS: m/z=387.0 [M+1].

Step H: Ethyl 9-((R)-6-chloro-5-fluoro-2-oxo-1,2-dihydrospiro[benzo[d][1,3]oxazine-4,3'-piperidine]-1'-carbonyl)-$2^5$-fluoro-3-aza-1(4,2)-pyridina-2(1,2)-benzenacyclononaphane-4-carboxylate (EX-34)

HATU (40.5 mg, 0.106 mmol) was added to a stirred mixture of (R)-6-chloro-5-fluorospiro[benzo[d][1,3]oxazine-4,3'-piperidin]-2(1H)-one, HCl (26.1 mg, 0.085 mmol), 4-(ethoxycarbonyl)-$2^5$-fluoro-3-aza-1(4,2)-pyridina-2(1,2)-benzenacyclononaphane-9-carboxylic acid (30 mg, 0.071 mmol) and Hunig's Base (37.2 μL, 0.213 mmol) in DCM (1 mL) at RT, and the mixture was stirred at RT for 2 h. LCMS showed the reaction was completed. The mixture was diluted with DCM (4 mL), washed with aqueous saturated sodium bicarbonate (1×2 mL), dried over $MgSO_4$, filtered and the solvent was evaporated under reduced pressure. The residue was purified by flash column chromatography on silica gel (40% EtOAc-EtOH (3:1) in Hexane) to EX-34. MS: m/z=639.2 [M+1].

Four diastereomers were resolved by SFC (OD-H (2×25 cm) 20% methanol (0.1% DEA)/$CO_2$, 100 bar, 220 nM) to give isomer A (first peak), isomer B (second peak), isomer C (third peak), and isomer D (fourth peak). LC/MS: m/z=639.2 [M+1].

Step I: 9-((R)-6-chloro-5-fluoro-2-oxo-1,2-dihydrospiro[benzo[d][1,3]oxazine-4,3'-piperidine]-1'-carbonyl)-$2^5$-fluoro-3-aza-1(4,2)-pyridina-2(1,2)-benzenacyclononaphane-4-carboxylic Acid (EX-35)

Aq. NaOH (1M solution in water) (0.106 mL, 0.106 mmol) was added to a stirred, room temperature mixture of ethyl 9-((R)-6-chloro-5-fluoro-2-oxo-1,2-dihydrospiro[benzo[d][1,3]oxazine-4,3'-piperidine]-1'-carbonyl)-$2^5$-fluoro-3-aza-1(4,2)-pyridina-2(1,2)-benzenacyclononaphane-4-carboxylate (34 mg, 0.053 mmol) in methanol (2 mL) and the mixture was stirred at RT overnight. The mixture was concentrated and the residue was diluted with DMSO (1.5 mL), the insoluble was filtered off, the filtrate was evaporated. The crude product was resolved by SFC (AS-H (21×250 mm), 30% 2:1 MeOH:MeCN/$CO_2$, 100 bar, 35° C., 254 nm) to provide isomer A (first peak) and isomer B (second peak) as solids. LC/MS: m/z=611.1 [M+1].

By using procedures similar to those described above, the following compounds were synthesized and characterized

| Example | Structure | LCMS [M + 1] | Hu FXIa Ki (nM) |
|---|---|---|---|
| 34a | ethyl 9-((R)-6-chloro-5-fluoro-2-oxo-1,2-dihydrospiro[benzo[d][1,3]oxazine-4,3'-piperidine]-1'-carbonyl)-$2^5$-fluoro-3-aza-1(4,2)-pyridina-2(1,2)-benzenacyclononaphane-4-carboxylate (isomer a) | 639 | 628 |

| Example | Structure | LCMS [M + 1] | Hu FXIa Ki (nM) |
| --- | --- | --- | --- |
| 34b | ethyl 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylate (isomer b) | 639 | >875 |
| 34c | ethyl 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylate (isomer c) | 640 | 196 |
| 34d | ethyl 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylate (isomer d) | 639 | >875 |
| 35a | 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylic acid (isomer a) | 611 | >875 |

| Example | Structure | LCMS [M + 1] | Hu FXIa Ki (nM) |
|---|---|---|---|
| 35b | 9-((R)-6-chloro-5-fluoro-2-oxo-1,2-dihydrospiro[benzo[d][1,3]oxazine-4,3'-piperidine]-1'-carbonyl)-2⁵-fluoro-3-aza-1(4,2)-pyridina-2(1,2)-benzenacyclononaphane-4-carboxylic acid (isomer b) | 611 | >875 |
| 36a | ethyl 9-((R)-6-chloro-5-fluoro-2-oxo-1,2-dihydrospiro[benzo[d][1,3]oxazine-4,3'-pyrrolidine]-1'-carbonyl)-2⁵-fluoro-3-aza-1(4,2)-pyridina-2(1,2)-benzenacyclononaphane-4-carboxylate (isomer a) | 625 | >875 |
| 36b | ethyl 9-((R)-6-chloro-5-fluoro-2-oxo-1,2-dihydrospiro[benzo[d][1,3]oxazine-4,3'-pyrrolidine]-1'-carbonyl)-2⁵-fluoro-3-aza-1(4,2)-pyridina-2(1,2)-benzenacyclononaphane-4-carboxylate (isomer b) | 625 | >875 |
| 37a | 9-((R)-6-chloro-5-fluoro-2-oxo-1,2-dihydrospiro[benzo[d][1,3]oxazine-4,3'-pyrrolidine]-1'-carbonyl)-2⁵-fluoro-3-aza-1(4,2)-pyridina-2(1,2)-benzenacyclononaphane-4-carboxylic acid (isomer a) | 597 | >875 |

| Example | Structure | LCMS [M + 1] | Hu FXIa Ki (nM) |
|---|---|---|---|
| 37b | 9-((R)-6-chloro-5-fluoro-2-oxo-1,2-dihydrospiro[benzo[d][1,3]oxazine-4,3'-pyrrolidine]-1'-carbonyl)-2⁵-fluoro-3-aza-1(4,2)-pyridina-2(1,2)-benzenacyclononaphane-4-carboxylic acid (isomer b) | 598 | >875 |
Example 38
Methyl (4-(((2S)-1-(6-chloro-2-oxo-1,2-dihydrospiro[pyrido[2,3-d][1,3]oxazine-4,3'-pyrrolidin]-1'-yl)-1-oxo-3-phenylpropan-2-yl)carbamoyl)phenyl)carbamate (EX-38)
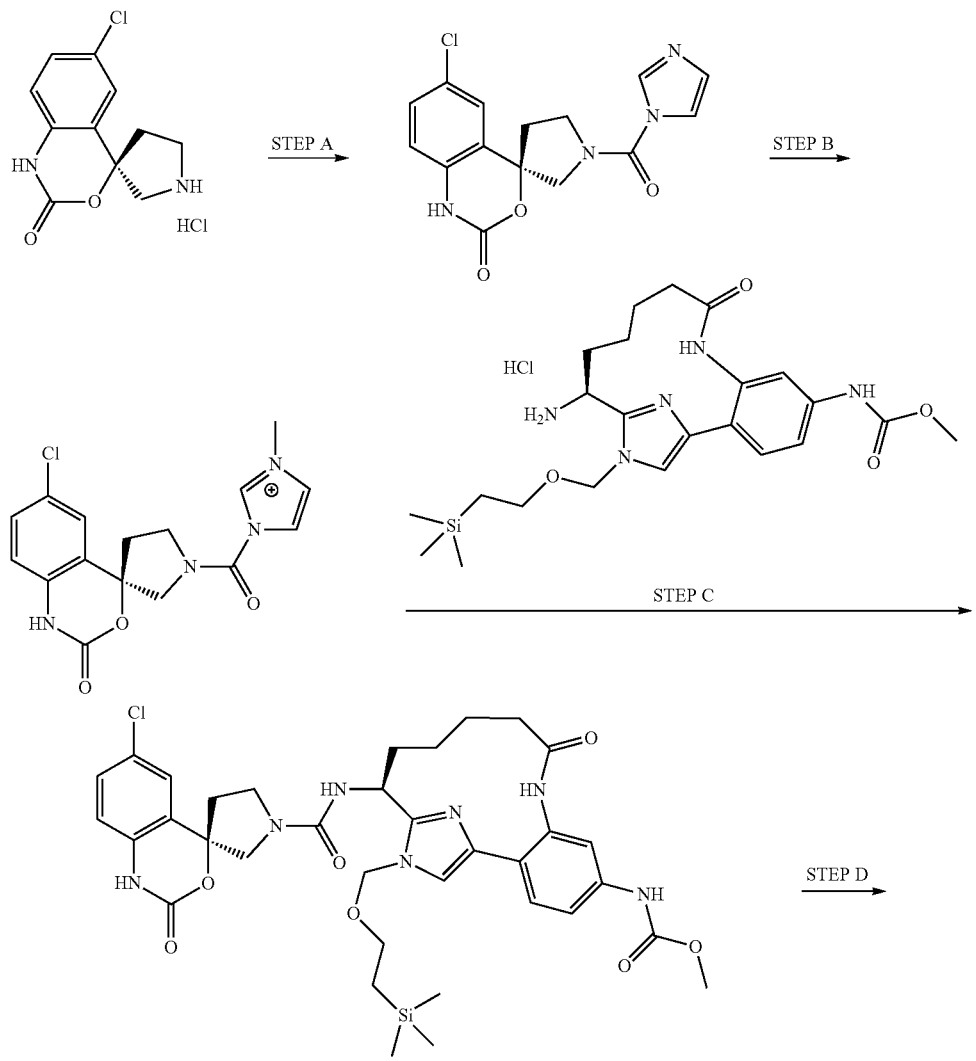

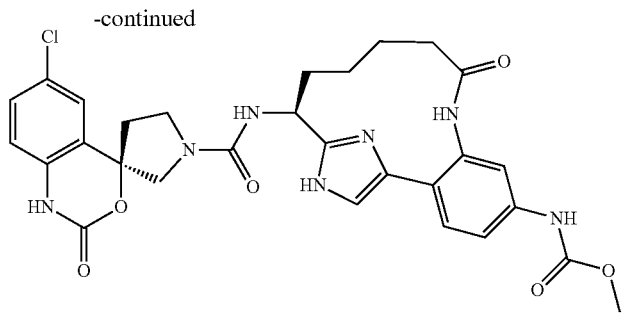

EX-38

Step A: (R)-6-Chloro-1'-(1H-imidazole-1-carbonyl) spiro[benzo[d][1,3]oxazine-4,3'-pyrrolidin]-2(1H)-one To a stirred solution of (R)-6-chlorospiro[benzo[d][1,3]oxazine-4,3'-pyrrolidin]-2(1H)-one hydrochloride (200 mg, 0.727 mmol) in THF (1322 µl) was added DIPEA (127 µl, 0.727 mmol) and di(1H-imidazol-1-yl)methanone (128 mg, 0.792 mmol) at RT. The reaction mixture was heated to 60° C. overnight. After cooling down to RT, sat. NaHCO$_3$ (30 mL) was added. The reaction mixture was extracted with EtOAc (100 mL). The organic layer was washed with brine, dried over MgSO4, filtered and concentrated. The crude product was purfied by flash silica gel column chromatography (EtOAc/Hex=1/1 to 10% MeOH in DCM) to afford the title compound. LC/MS=333 [M+1].

Step D: (R)-1-(6-chloro-2-oxo-1,2-dihydrospiro[benzo[d][1,3]oxazine-4,3'-pyrrolidine]-1'-carbonyl)-3-methyl-1H-imidazol-3-ium To a stirred solution of (R)-6-chloro-1$^1$-(1H-imidazole-1-carbonyl)spiro[benzo[d][1,3]oxazine-4,3'-pyrrolidin]-2(1H)-on (151 mg, 0.454 mmol) in acetonitrile (4538 µl) was added iodomethane (114 µl, 1.815 mmol) at RT. The reaction mixture was stirred at RT overnight. The solvent was evaporated and the crude product was used in the the next step without aq. work up or further purification. LC/MS=347 [M+1].

Step C: Methyl ((S,Z)-9-((R)-6-chloro-2-oxo-1,2-dihydrospiro[benzo[d][1,3]oxazine-4,3'-pyrrolidine]-1'-carboxamido)-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate To a stirred solution of (R)-1-(6-chloro-2-oxo-1,2-dihydrospiro[benzo[d][1,3]oxazine-4,3'-pyrrolidine]-1'-carbonyl)-3-methyl-1H-imidazol-3-ium (158 mg, 0.454 mmol) in DMF (4 ml) was added methyl (S,Z)-(9-amino-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate hydrochloride (synthesized as described in the publication WO2011/100401, 232 mg, 0.454 mmol) and TEA (0.127 ml, 0.909 mmol) at RT. The reaction mixture was stirred at RT overnight. Sat. NaHCO$_3$ (30 mL) was added and the reaction mixture was diluted with EtOAc (100 mL). The organic layer was washed with brine, dried over MgSO$_4$, filtered and concentrated. The crude product was purified by flash silica gel column chromatography (1/1EtOAc/Hex to 100% EtOAc) to give the title compound. LC/MS=739 [M+1].

Step D: Methyl ((S,Z)-9-((R)-6-chloro-2-oxo-1,2-dihydrospiro[benzo[d][1,3]oxazine-4,3'-pyrrolidine]-1'-carboxamido)-4-oxo-1$^1$H-3-aza-1(4,2)-imidazola-2(1,2)-benzenacyclononaphane-2$^4$-yl)carbamate (EX-38)

To a sealed tube with methyl ((S,Z)-9-((R)-6-chloro-2-oxo-1,2-dihydrospiro[benzo[d][1,3]oxazine-4,3'-pyrrolidine]-1'-carboxamido)-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate (220.5 mg, 0.299 mmol)) was added HCl (747 µl, 2.99 mmol) (4M in dioxane) and 1,4-dioxane (1493 µl) at RT. The tube was sealed and heated to 50° C. overnight. The solvent was evaporated and sat. NaHCO$_3$ (aq) and DCM were added. A PPT was generated. The PPT was filtered and washed with 10% MeOH/DCM and dried in a vac. oven to afford EX-38. LC/MS=609 [M+1].

The following intermediates (Int-6 and Int-7) were synthesized as described in the publication WO2014/022767.

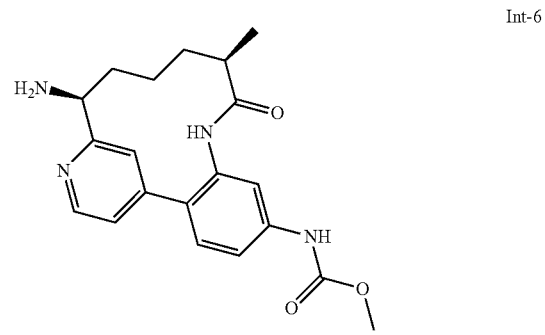

Int-6

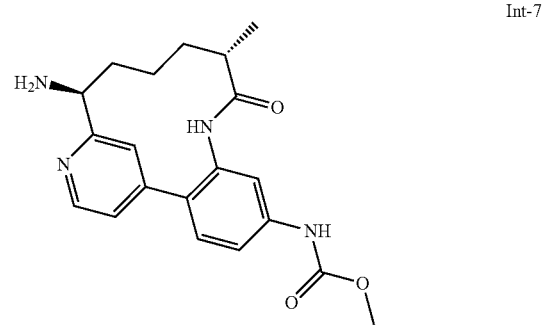

Int-7

By using procedures similar to those described above, the following compounds were synthesized and characterized

| Example | Structure | LCMS [M + 1] | Hu FXIa Ki (nM) |
|---|---|---|---|
| 38 | methyl ((S,Z)-9-((R)-6-chloro-2-oxo-1,2-dihydrospiro[benzo[d][1,3]oxazine-4,3'-pyrrolidine]-1'-carboxamido)-4-oxo-11H-3-aza-1(4,2)-imidazola-2(1,2)-benzenacyclononaphane-2⁴-yl)carbamate | 609 | 16.1 |
| 39 | methyl ((5S,9S)-9-((R)-6-chloro-2-oxo-1,2-dihydrospiro[benzo[d][1,3]oxazine-4,3'-piperidine]-1'-carboxamido)-5-methyl-4-oxo-3-aza-1(4,2)-pyridina-2(1,2)-benzenacyclononaphane-2⁴-yl)carbamate | 648 | 455 |
| 40 | methyl ((5R,9S)-9-((R)-6-chloro-2-oxo-1,2-dihydrospiro[benzo[d][1,3]oxazine-4,3'-piperidine]-1'-carboxamido)-5-methyl-4-oxo-3-aza-1(4,2)-pyridina-2(1,2)-benzenacyclononaphane-2⁴-yl)carbamate | 648 | >5000 |

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM $CaCl_2$, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 100 µM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, $[I]/e$, and $[I]/e$ (where $[S]$, $[I]$, and e respectively represent the total concentrations, of substrate, inhibitor and enzyme), the equilibrium constant ($K_i$) for dissociation of the inhibitor from the enzyme can be obtained from the dependence of $V_o/V_i$ on $[I]$ shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels. The Ki values measured for each of the example compounds of the invention using this assay are reported in the tables above (as "Hu FXIa Ki (nM)").

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at room temperature or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM $CaCl_2$, and 0.1% PEG 8000 (polyethylene glycol; Fisher Scientific). Determinations were made using purified Human plasma kallikrein at a final concentration of 0.5 nM (Enzyme Research Laboratories) and the synthetic substrate, Acetyl-K—P-R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). $IC_{50}$ was determined by inflection point from a four parameter logistic curve fit. Ki was calculated using the Cheng Prusoff equation, $Ki=IC_{50}/(1+([S]/Km))$.

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels. The Ki values measured for each of the example compounds of the invention using this assay are reported in the tables below (as "Hu P. Kallikrein (nM)").

Human Plasma Kallikrein Data:

| Example | Hu P. Kallikrein (nM) |
|---------|----------------------|
| 1a | 1.99 |
| 3a | 0.82 |
| 4 | 1.24 |
| 6a | 0.69 |
| 6b | 32.0 |
| 7a | 0.39 |
| 8 | 0.56 |
| 9 | 0.57 |
| 10 | 0.96 |
| 11 | 1.32 |
| 12 | 1.28 |
| 12b | 1.29 |
| 13b | 1.11 |
| 14a | 5.5 |
| 15a | 1.70 |

| Example | Hu P. Kallikrein (nM) |
|---------|----------------------|
| 17a | 3.8 |
| 18a | 3.65 |
| 21a | 17 |
| 22a | 0.77 |
| 23b | 8.5 |
| 25a | 0.75 |
| 26 | 1.22 |
| 27 | 0.6 |
| 28 | 12.66 |
| 30b | 1.52 |
| 31 | 63.7 |

-continued

| Example | Hu P. Kallikrein (nM) |
|---------|----------------------|
| 32      | 15.5                 |
| 32b     | 1.42                 |
| 38      | 4.5                  |

What is claimed is:
1. A compound of the Formula (I):

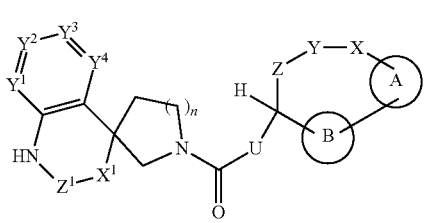

or a pharmaceutically acceptable salt thereof, wherein:
$Y^1$ is $CR^3$ or N;
$Y^2$ is $CR^3$ or N;
$Y^3$ is $CR^3$ or N;
$Y^4$ is $CR^3$ or N,
such that three of $Y^1$, $Y^2$, $Y^3$ and $Y^4$ are not simultaneously N, and all four of $Y^1$, $Y^2$, $Y^3$ and $Y^4$ are not simultaneously N;
each $R^3$ is independently hydrogen, $C_{1-3}$ alkyl, $C_{3-6}$ cycloalkyl, halo, cyano or hydroxy, wherein said $C_{1-3}$ alkyl and said $C_{3-6}$ cycloalkyl groups are optionally independently substituted with one to three groups independently selected from halo or hydroxyl;
U is a bond or NH;
—$Z^1$—$X^1$— is selected from the group consisting of: —C(O)O—, —C(O)CH$_2$—, —C(O)NH—, —S(O)$_2$O—, —S(O)$_2$CH$_2$—, —S(O)$_2$NH—, —S(O)CH$_2$—, —S(O)NH—, —C(O)—, and —S(O)$_2$—;
n is 1, 2, or 3;
Ⓐ is aryl or heteroaryl, each of which is optionally substituted with one to three groups independently selected from the group consisting of halo, cyano, $R^6$, $OR^6$, $C(O)OR^6$, $NR^6R^7$, NHC(O)O(C$_1$-C$_6$)alkyl, NHC(O)OC$_{3-6}$cycloalkyl, —NHSO$_2$(C$_1$-C$_6$)alkyl, CONR$^7$R$^8$, and —CH$_2$CONR$^7$R$^8$;
Ⓑ is aryl or heteroaryl, each of which is optionally substituted with one to three groups independently selected from the group consisting of halo, cyano, oxo, $R^6$, $OR^6$, $C(O)OR^6$, $C_{1-3}$ alkyl-C(O)OR$^6$, C(O)NR$^6$R$^7$ and NR$^6$R$^7$;
—Y—X— is selected from the group consisting of —C(O)—NR$^6$—, —CH(OC(O)—NR$^6$—, —CH(C(O)OR$^7$)—NR$^6$—, —C(O)—O—, —NR$^6$—C(O)—, —CH(C(O)N(R$^6$R$^7$))—NR$^6$—, —CH(CR$^6$R$^7$OR$^8$)—NR$^6$—, —CH(CR$^6$R$^7$NR$^6$R$^7$)—NR$^6$—, —OC(O)—NR$^6$—, —NR$^6$—C(O)O—, —NR$^6$—C(O)NR$^6$—, and —S(O)$_2$—NR$^6$—;
$R^5$ is fluoro or $C_{1-6}$ alkyl;
Z is $C_{3-8}$ alkylene or $C_{3-8}$ alkenylene, wherein one of the carbon atoms in said alkylene and alkenylene, where chemically permitted, may be replaced with O, NR$^6$, C(O), C(O)NR$^6$, NR$^6$C(O), S, SO or SO$_2$;
each $R^6$ is independently hydrogen or $C_{1-6}$ alkyl, which is optionally substituted with one to three groups independently selected from the group consisting of halo, hydroxyl, (C$_1$-C$_3$)alkoxyl, C(O)OH, and C(O)O(C$_1$-C$_3$)alkyl;
each $R^7$ is independently hydrogen, $C_{1-6}$ alkyl, heteroaryl or heterocyclyl, wherein said alkyl group is optionally substituted with one to three groups independently selected from the group consisting of halo and hydroxy; and
each $R^8$ is independently hydrogen or $C_{1-6}$ alkyl.

2. A compound having a structural Formula (III):

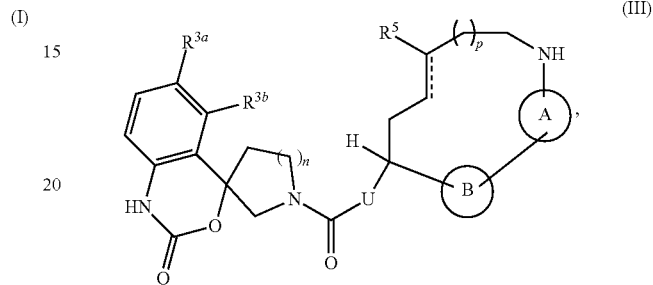

or a pharmaceutically acceptable salt thereof, wherein:
Ⓐ is aryl or heteroaryl, each of which is optionally substituted with one to three groups independently selected from the group consisting of halo, cyano, $R^6$, $OR^6$, $C(O)OR^6$, $NR^6R^7$, NHC(O)O(C$_1$-C$_6$)alkyl, NHC(O)OC$_{3-6}$cycloalkyl, —NHSO$_2$(C$_1$-C$_6$)alkyl, CONR$^7$R$^8$, and —CH$_2$CONR$^7$R$^8$,
Ⓑ is aryl or heteroaryl, each of which is optionally substituted with one to three groups independently selected from the group consisting of halo, cyano, oxo, $R^6$, $OR^6$, $C(O)OR^6$, $C_{1-3}$ alkyl-C(O)OR$^6$, C(O)NR$^6$R$^7$ and NR$^6$R$^7$,
each $R^6$ is independently hydrogen or $C_{1-6}$ alkyl, which is optionally substituted with one to three groups independently selected from the group consisting of halo, hydroxyl, (C$_1$-C$_3$)alkoxyl, C(O)OH, and C(O)O(C$_1$-C$_3$)alkyl,
each $R^7$ is independently hydrogen, $C_{1-6}$ alkyl, heteroaryl or heterocyclyl, wherein said alkyl group is optionally substituted with one to three groups independently selected from the group consisting of halo and hydroxy;
each $R^8$ is independently hydrogen or $C_{1-6}$ alkyl;
Y is selected from the group consisting of —C(O), —CH(R$^5$)C(O) and —CH(C(O)OR$^7$);
U is a bond or NH;
$R^5$ is fluoro or $C_{1-6}$ alkyl;
n is 1, 2, or 3;
p is 0, 1 or 2;
the dotted line represents a single or double bond;
$R^{3a}$ is halo; and
$R^{3b}$ is selected from the group consisting of H and halo.

3. The compound according to claim 1, or a pharmaceutically acceptable salt thereof, wherein:
n is 1.

4. The compound according to claim 1, or a pharmaceutically acceptable salt thereof, wherein:
n is 2.

5. The compound according to claim 2, or a pharmaceutically acceptable salt thereof, wherein:
$R^{3a}$ is chloro and $R^{3b}$ is selected from the group consisting of H, chloro and fluoro.

6. The compound according to claim 1, or a pharmaceutically acceptable salt thereof, wherein:

—Y—X— is —C(O)—NR⁶—.

7. The compound according to claim 1, or a pharmaceutically acceptable salt thereof, wherein:

—Y—X— is —CH(R⁵)C(O)—NR⁶—.

8. The compound according to claim 1, or a pharmaceutically acceptable salt thereof, wherein:

—Y—X— is —CH(C(O)OR⁷)—NR⁶—.

9. The compound according to claim 1, or a pharmaceutically acceptable salt thereof, wherein:

Ⓐ is

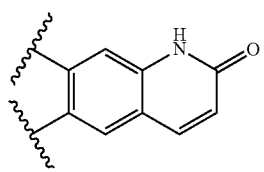

or phenyl which is optionally substituted with one to three groups independently selected from the group consisting of halo, cyano, R⁶, OR⁶, C(O)OR⁶, NR⁶R⁷, NHC(O)O(C₁-C₆)alkyl, NHC(O)OC₃₋₆cycloalkyl, —NHSO₂(C₁-C₆)alkyl, CONR⁷R⁸, and —CH₂CONR⁷R⁸.

10. The compound according to claim 1, or a pharmaceutically acceptable salt thereof, wherein:

Ⓑ is selected from the group consisting of phenyl, pyridinyl, oxazolyl, and imidazoyl, wherein each said phenyl, pyridinyl, and imidazoyl, is unsubstituted or substituted with one to three groups independently selected from the group consisting of halo, cyano, oxo, R⁶, OR⁶, C(O)OR⁶, C₁₋₃ alkyl-C(O)OR⁶, C(O)NR⁶R⁷ and NR⁶R⁷.

11. The compound of claim 1, or a pharmaceutically acceptable salt thereof, said compound having a structure selected from the group consisting of:

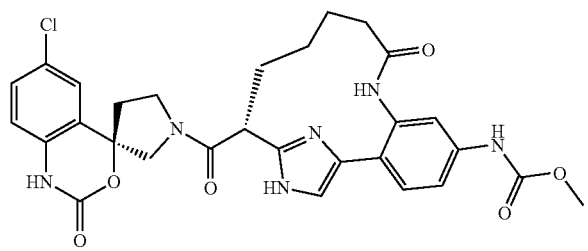

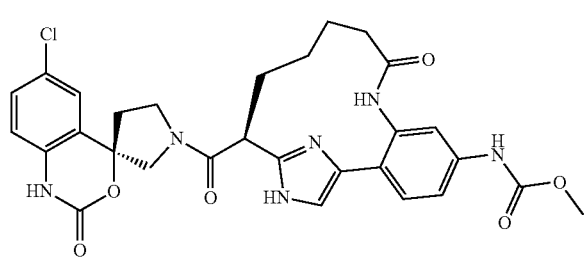

-continued

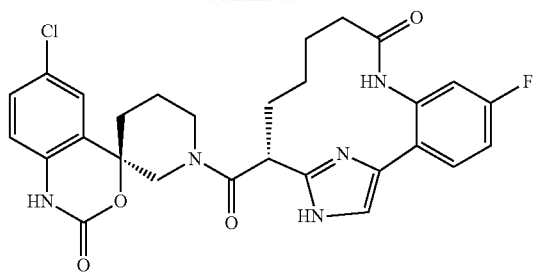

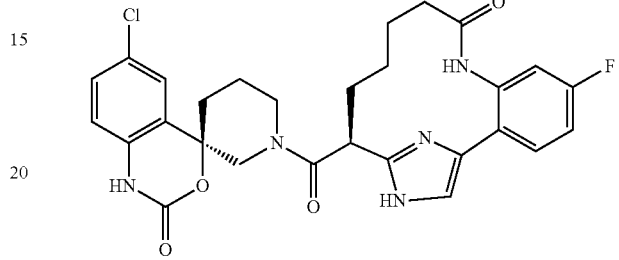

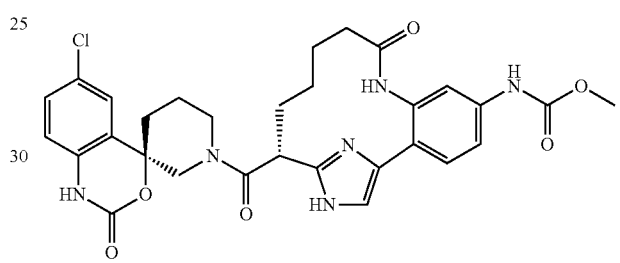

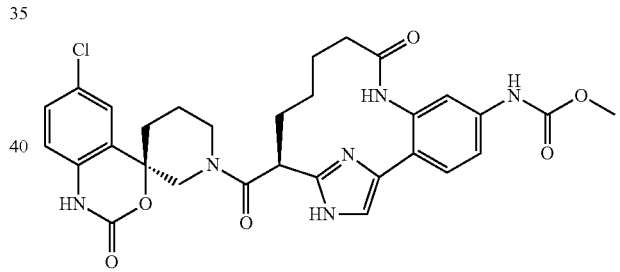

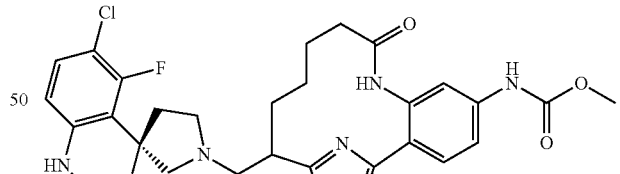

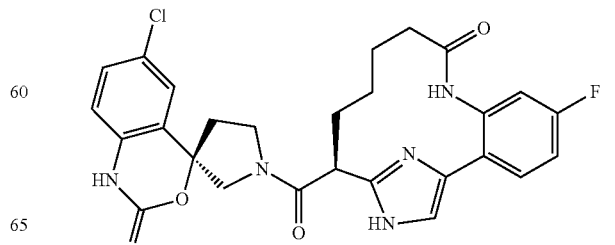

145
-continued
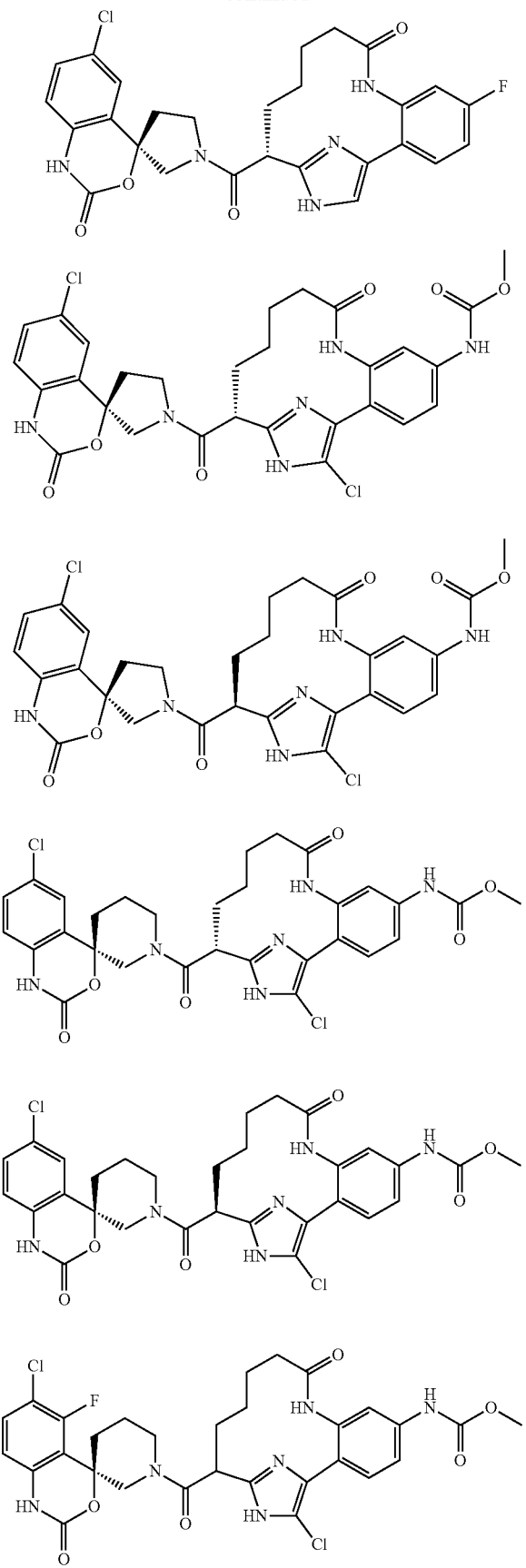
146
-continued
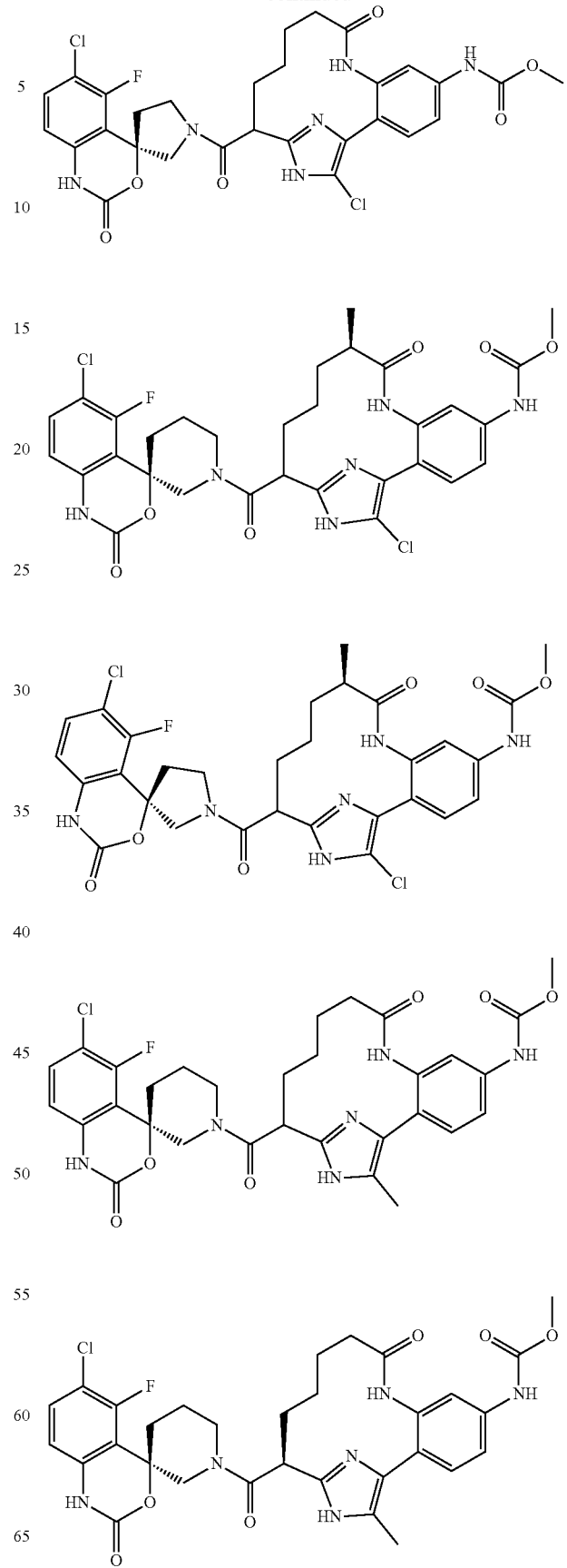

147
-continued
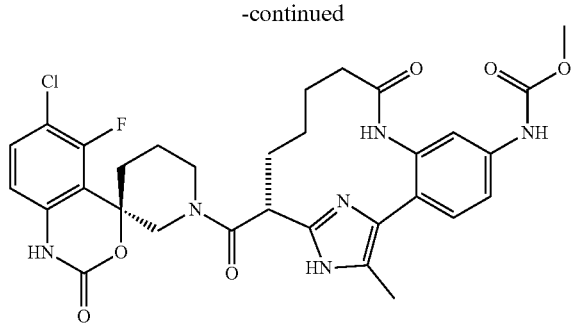
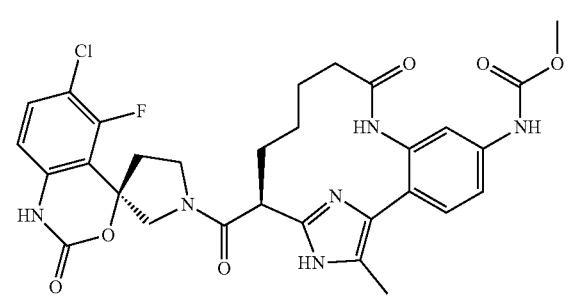
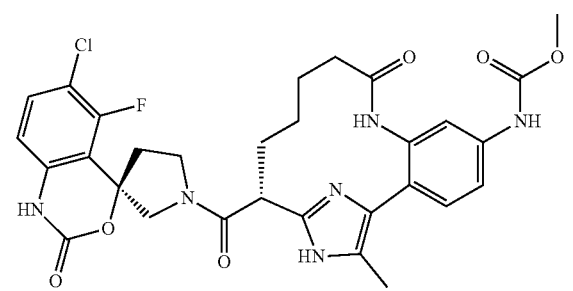
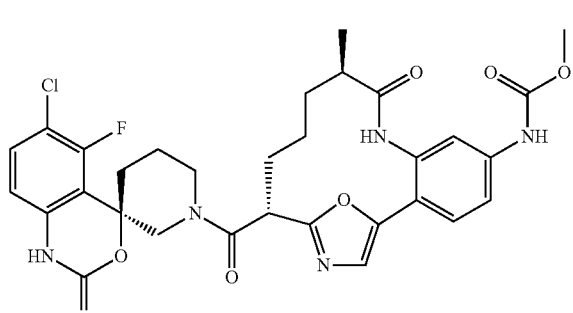
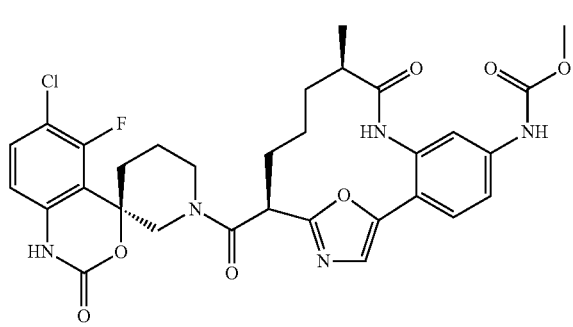
148
-continued
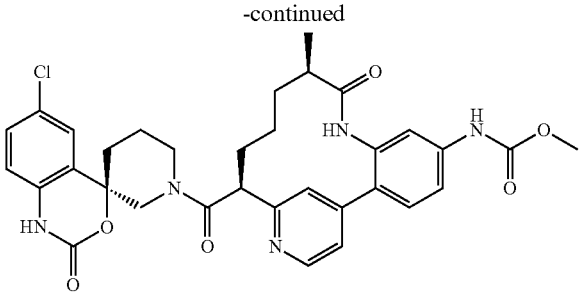

149
-continued

150
-continued

151
-continued
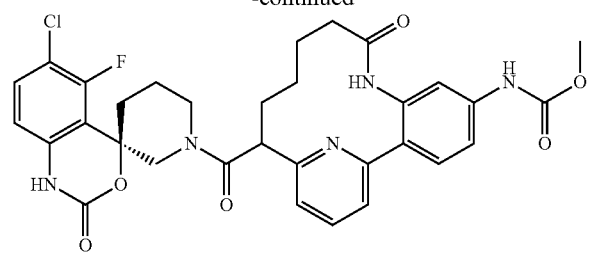
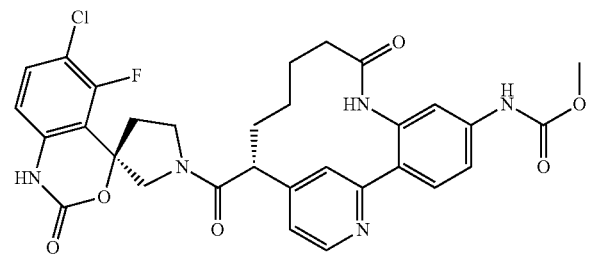
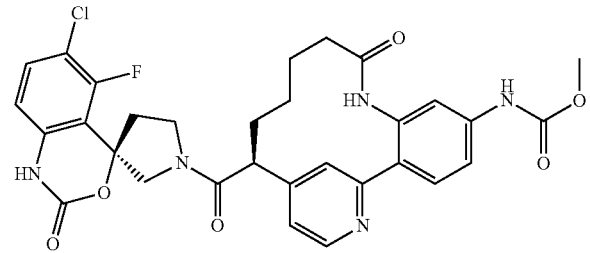
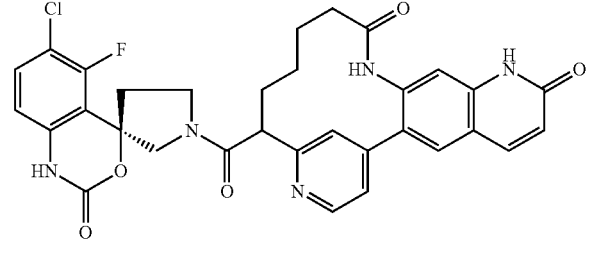
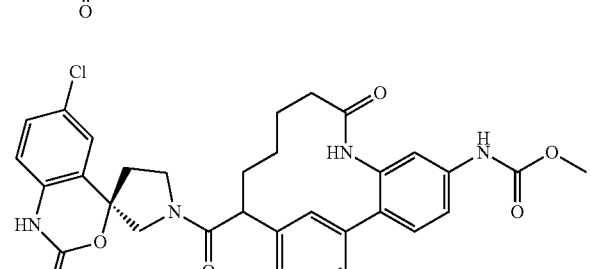
152
-continued
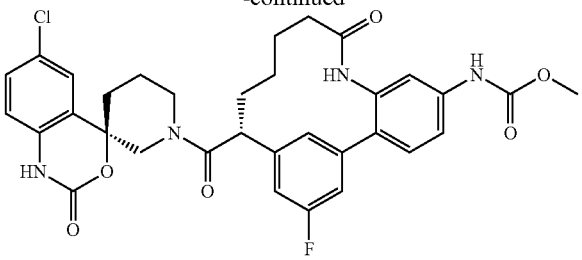
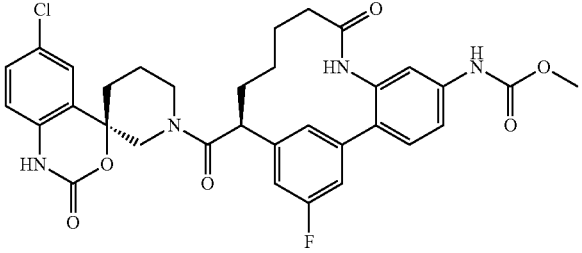 [SMILES: COC(=O)Nc1ccc2c(c1)NC(=O)CCCC[C@H](C(=O)N1CCC[C@@]3(C1)OC(=O)Nc1ccc(Cl)cc13)c1cc(F)cc-2c1]
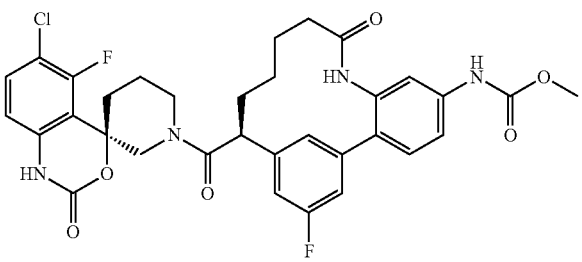 [SMILES: COC(=O)Nc1ccc2c(c1)NC(=O)CCCC[C@H](C(=O)N1CCC[C@@]3(C1)OC(=O)Nc1ccc(Cl)c(F)c13)c1cc(F)cc-2c1]
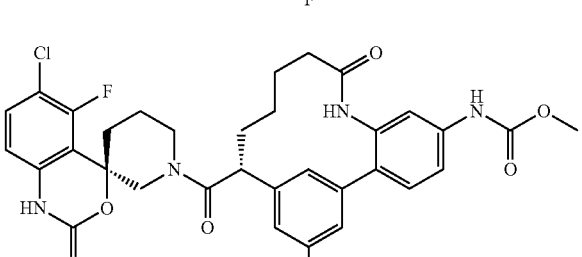
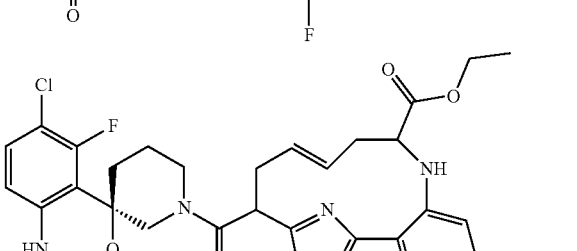
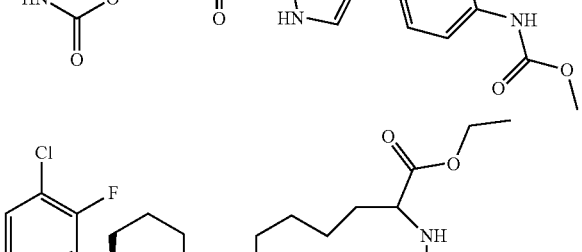
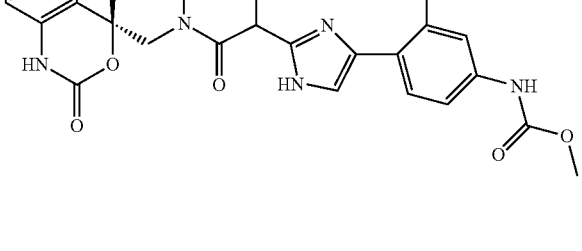

153
-continued
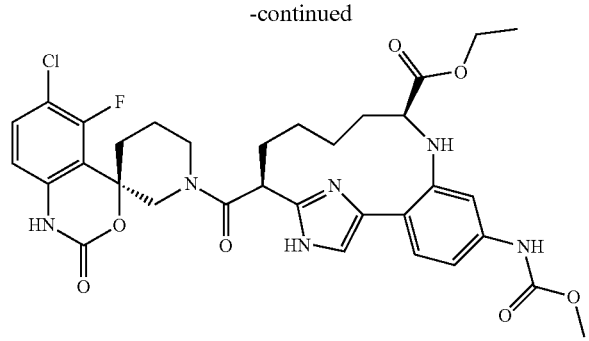
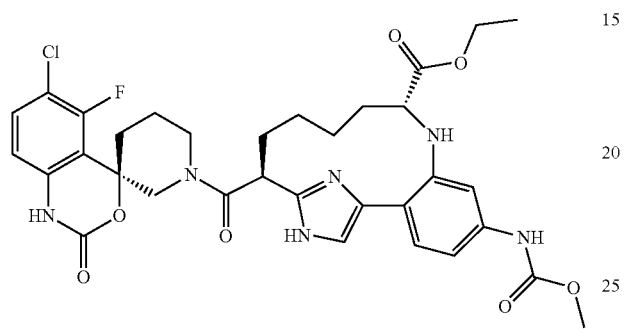
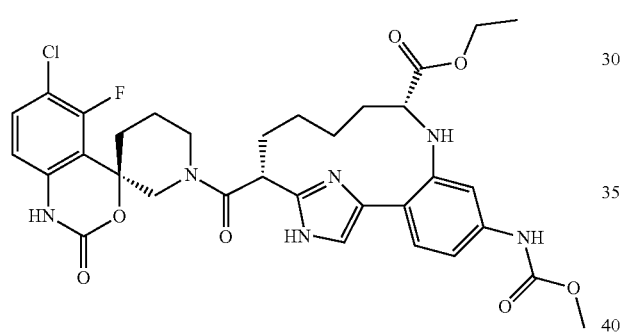
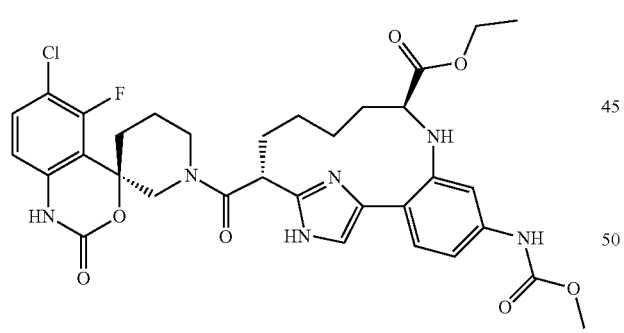
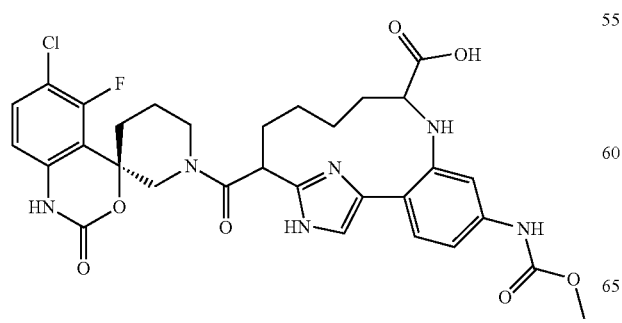
154
-continued
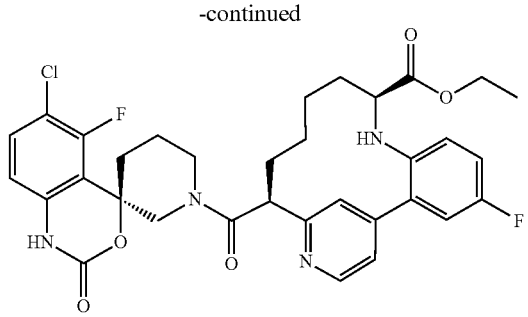
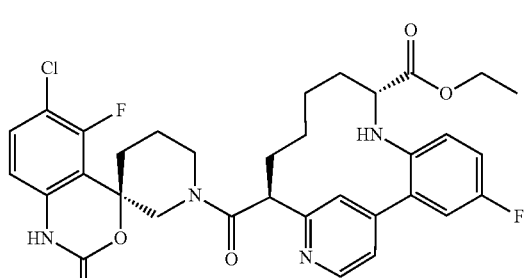
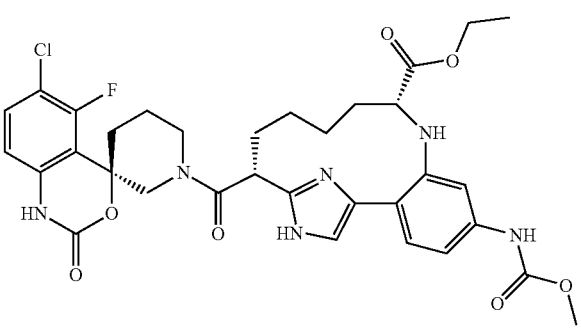
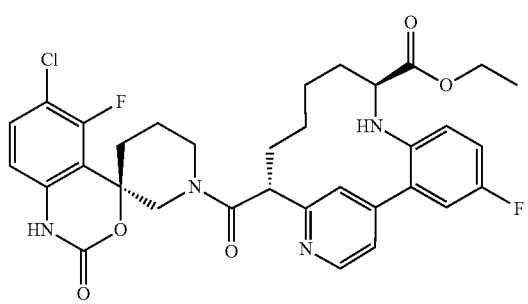
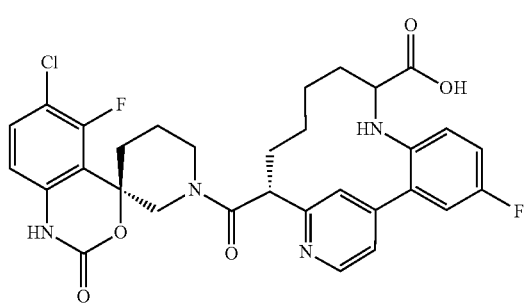

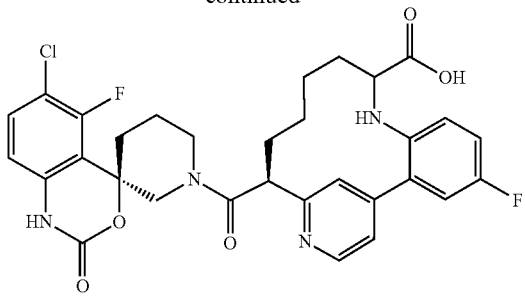
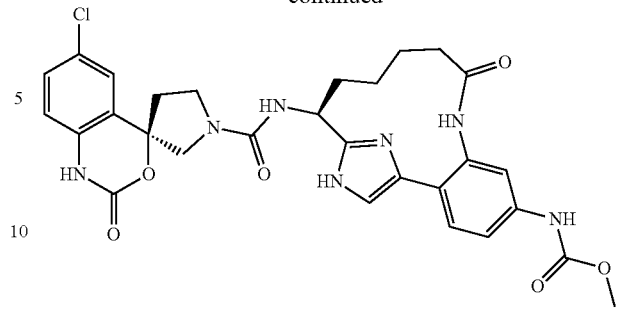
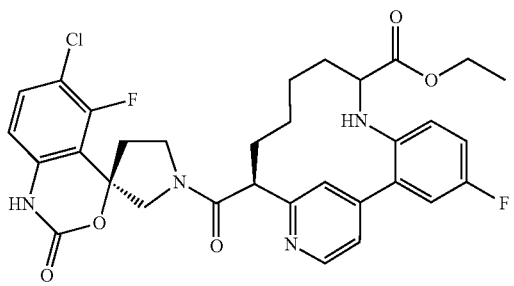
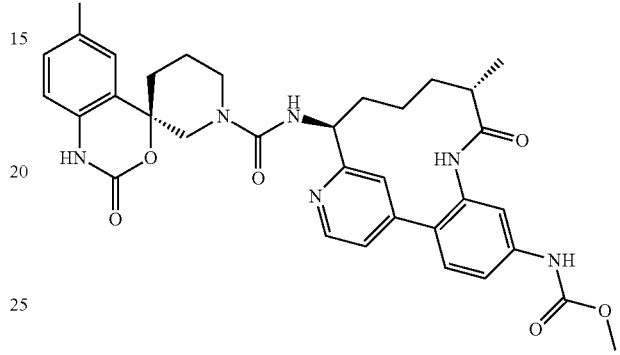
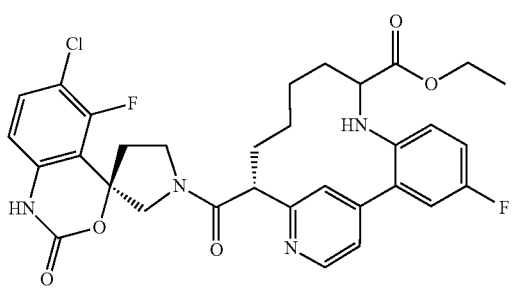
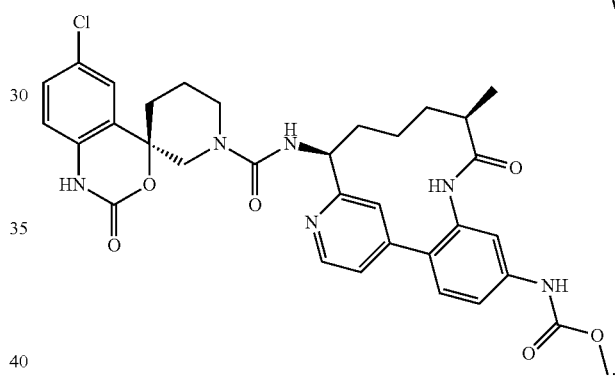
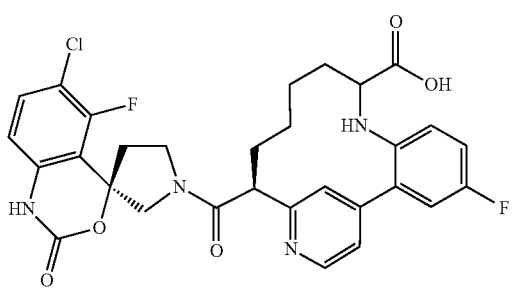
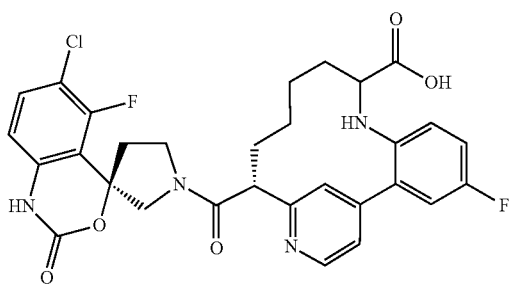

12. A pharmaceutically acceptable composition comprising a compound according to claim 1, or a pharmaceutically acceptable salt thereof, and a pharmaceutically acceptable carrier.

13. A method for inhibiting thrombus formation in blood or treating thrombus formation in blood comprising administering a composition of claim 12 to a mammal in need of thereof.

14. A method for preventing thrombus formation in blood comprising administering a composition of claim 12 to a mammal in need thereof.

15. A method of treating venous thromboembolism and or pulmonary embolism in a mammal comprising administering a composition of claim 12 to a mammal in need thereof.

16. A method of treating deep vein thrombosis in a mammal comprising administering a composition of claim 12 to a mammal in need thereof.

17. A method of treating thromboembolic stroke in a human comprising administering a composition of claim 12 to a mammal in need thereof.

* * * * *